United States Patent
O'Reilly et al.

(10) Patent No.: US 10,857,182 B2
(45) Date of Patent: Dec. 8, 2020

(54) GENERATION AND USE IN ADOPTIVE IMMUNOTHERAPY OF STEM CELL-LIKE MEMORY T CELLS

(71) Applicant: Memorial Sloan Kettering Cancer Center, New York, NY (US)

(72) Inventors: Richard John O'Reilly, Roxbury, CT (US); Aisha Nasreen Hasan, Blue Bell, PA (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 16/333,651

(22) PCT Filed: Sep. 22, 2017

(86) PCT No.: PCT/US2017/052846
§ 371 (c)(1),
(2) Date: Mar. 15, 2019

(87) PCT Pub. No.: WO2018/057823
PCT Pub. Date: Mar. 29, 2018

(65) Prior Publication Data
US 2020/0009189 A1 Jan. 9, 2020

Related U.S. Application Data

(60) Provisional application No. 62/399,311, filed on Sep. 23, 2016.

(51) Int. Cl.
| | |
|---|---|
| A61K 35/17 | (2015.01) |
| A61P 31/20 | (2006.01) |
| A61K 9/00 | (2006.01) |
| A61K 39/245 | (2006.01) |
| C07K 14/725 | (2006.01) |
| C12N 5/0783 | (2010.01) |
| C12N 7/00 | (2006.01) |
| A61K 39/00 | (2006.01) |

(52) U.S. Cl.
CPC ............ *A61K 35/17* (2013.01); *A61K 9/0019* (2013.01); *A61K 39/245* (2013.01); *A61P 31/20* (2018.01); *C07K 14/7051* (2013.01); *C12N 5/0637* (2013.01); *C12N 7/00* (2013.01); *A61K 2039/5158* (2013.01); *A61K 2039/54* (2013.01); *A61K 2039/545* (2013.01); *C12N 2510/00* (2013.01); *C12N 2710/16134* (2013.01)

(58) Field of Classification Search
CPC .... A61K 35/17; A61K 45/06; A61K 2121/00; A61K 9/0019; A61K 39/245; A61K 2039/5158; A61K 2039/54; A61K 2039/545; A61P 31/20; A61P 35/02; A61P 35/00; A61P 33/10; A61P 31/22; A61P 31/18; A61P 31/16; A61P 31/14; A61P 31/12; A61P 31/10; A61P 31/04; C07K 14/7051; Y02A 50/30; C12N 5/0637; C12N 7/00; C12N 2510/00; C12N 2710/16134; C12N 2710/16111

See application file for complete search history.

(56) References Cited

U.S. PATENT DOCUMENTS

| | | |
|---|---|---|
| 3,753,357 A | 8/1973 | Schwartz et al. |
| 4,199,022 A | 4/1980 | Senkan et al. |
| 6,723,695 B1 | 4/2004 | Burrows et al. |
| 8,425,898 B2 | 4/2013 | Sampson et al. |
| 9,011,835 B2 | 4/2015 | Sampson et al. |
| 2004/0265325 A1 | 12/2004 | Diamond et al. |
| 2014/0086888 A1 | 3/2014 | Heslop et al. |

FOREIGN PATENT DOCUMENTS

| | | | |
|---|---|---|---|
| WO | WO 2014/039044 | 3/2014 | |
| WO | WO 2015/127190 | 8/2015 | |
| WO | WO 2016/073550 | 5/2016 | |
| WO | WO-2017072251 A1 * | 5/2017 | ........... C12N 5/0637 |
| WO | WO 2018/057823 | 3/2018 | |

OTHER PUBLICATIONS

Sadelain M. Chimeric antigen receptors: driving immunology towards synthetic biology. Curr Opin Immunol. Aug. 2016;41:68-76. doi: 10.1016/j.coi.2016.06.004. Epub Jun. 30, 2016.*

Busch DH, Fräßle SP, Sommermeyer D, Buchholz VR, Riddell SR. Role of memory T cell subsets for adoptive immunotherapy. Semin Immunol. Feb. 2016;28(1):28-34. Epub Mar. 11, 2016.*

Hasan AN, Selvakumar A, O'Reilly RJ. Artificial Antigen Presenting Cells: An Off the Shelf Approach for Generation of Desirable T-Cell Populations for Broad Application of Adoptive Immunotherapy. Adv Genet Eng. 2015;4(3):130. Epub Oct. 5, 2015.*

International Search Report and Written Opinion dated Mar. 29, 2018 for International Application No. PCT/US2017/052846; 17 pages.

"Biological therapy in treating patients at high-risk or with lymphoma, lymphoproliferative disease, or malignancies", ClinicalTrials. gov, accessed at https://clinicaltrials.gov/ct2/show/NCT00002663?term=NCT00002663&rank=1, first received on Nov. 1, 1999, accessed on Oct. 21, 2014, 5 pages.

(Continued)

*Primary Examiner* — Rachel B Gill

(74) *Attorney, Agent, or Firm* — Jones Day

(57) ABSTRACT

Provided herein are methods of generating antigen-specific T cells for therapeutic administration to a human patient having or suspected of having a pathogen or cancer, utilizing stem cell-like memory T cells ($T_{SCM}$ cells). Also disclosed are antigen-specific T cells generated by such methods, and methods of treating a human patient using such antigen-specific T cells.

35 Claims, 24 Drawing Sheets

Figure 1:
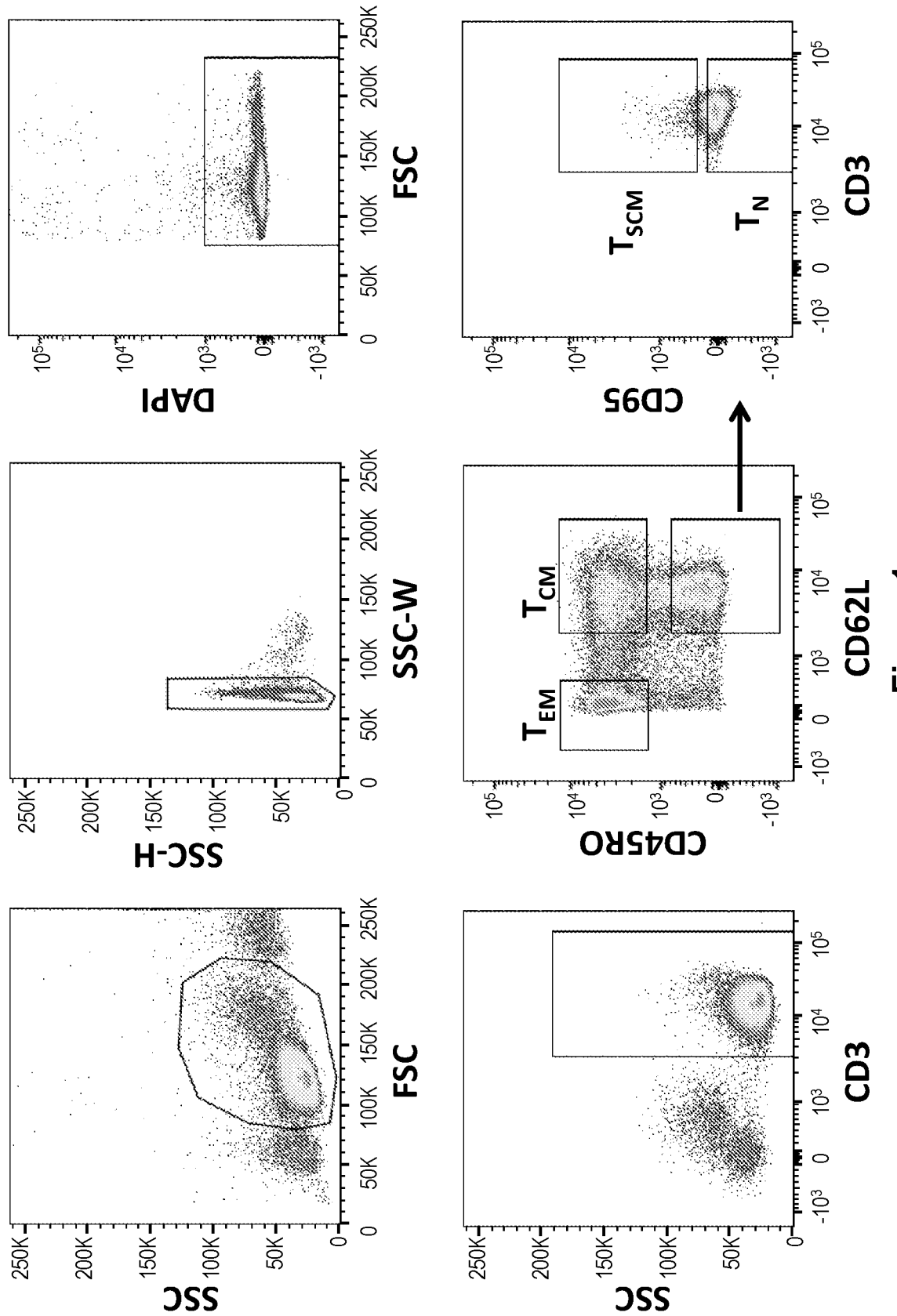

Specification includes a Sequence Listing.

(56) References Cited

OTHER PUBLICATIONS

"Form S-1 Registration Statement", filed with the United States Securities and Exchange Commission by Atara Biotherapeutics, Inc., dated Jun. 29, 2015, 203 pages.

"Therapeutic effects of Epstein-Barr virus immune T-lymphocytes derived from a normal HLA-compatible or partially-matched third-party donor in the treatment of EBV lymphoproliferative disorders and EBV-associated malignancies", ClinicalTrials.gov, accessed at http://www.clinicaltrials.gov/ct2/show/NCT01498484?term=NCT01498484&rank=1, first received on Dec. 21, 2011, accessed on Oct. 21, 2014, 5 pages.

"Primary transplant donor derived CMVpp65 specific T-cells for the treatment of CMV infection or persistent CMV viremia after allogeneic hematopoietic stem cell transplantation", ClinicalTrials.gov, accessed at http://www.clinicaltrials.gov/ct2/show/NCT01646645?term=NCT01646645&rank=1, first received on Jul. 18, 2012, accessed on Oct. 21, 2014, 4 pages.

"Trial of third party donor derived CMVpp65 specific T-cells for the treatment of CMV infection or persistent CMV viremia after allogeneic hematopoietic stem cell transplantation", ClinicalTrials.gov, accessed at ?https://clinicaltrials.gov/ct2/show/NCT02136797?term=NCT02136797&rank=1, first received on May 9, 2014, accessed on Nov. 10, 2014, 4 pages.

"Dose escalation trial of WT1-sensitized T cells for residual or relapsed leukemia after allogeneic hematopoietic progenitor cell transplantation", ClinicalTrials.gov, accessed at https://clinicaltrials.gov/ct2/show/NCT00620633?term=NCT00620633&rank=1, first received on Feb. 11, 2008, accessed on Oct. 3, 2016, 4 pages.

"Busulfan, melphalan, fludarabine and T-cell depleted allogeneic hematopoietic stem cell transplantation followed by post transplantation donor lymphocyte infusions", ClinicalTrials.gov, accessed at https://www.clinicaltrials.gov/ct2/show/NCT01131169?term=NCT01131169&rank=1, first received on May 25, 2010, accessed on Jan. 5, 2015, 5 pages.

"Dose escalation trial of WT-specific donor-derived T cells following-cell depleted allogeneic hematopoietic stem cell transplantation for patients with relapsed/refractory multiple myeloma", ClinicalTrials.gov, accessed at https://clinicaltrials.gov/ct2/show/NCT01758328?term=NCT01758328&rank=1, first received on Dec. 24, 2012, accessed on Oct. 3, 2016, 4 pages.

Amarnath and Fowler, Jan. 2012, "Harnessing autophagy for adoptive T cell therapy," Immunotherapy, 4(1):1-4.

American Association for Cancer Research (AACR) Press Release entitled "New T cell-based immunotherapy shows promise for lethal stem cell transplant complication," dated Apr. 19, 2015, 3 pages.

Argaet et al., 1994, "Dominant selection of an invariant T cell antigen receptor in reponse to persistent infection by Epstein-Barr virus", J Exp Med, 180:2335-2340.

Balduzzi et al., Jul. 2011, "Polyomavirus JC-targeted T-cell therapy for progressive multiple leukoencephalopathy in a hematopoietic cell transplantation recipient," Bone Marrow Transplantation, 46(7):987-992.

Bao et al., Apr. 2012, "Adoptive immunotherapy with CMV specific cytotoxic T lymphocytes for stem cell transplant patients with refractory CMV infections," Journal of Immunotherapy, 35(3):293-298.

Barker et al., Dec. 2010, "Successful treatment of EBV-associated posttransplantation lymphoma after cord blood transplantation using third-party EBV-specific cytotoxic T lymphocytes," Blood, 116(23):5045-5049 (Published online Sep. 8, 2010).

Berger et al., 2008, "Adoptive transfer of effector CD8+ T cells derived from central memory cells establishes persistent T cell memory in primates", J Clin Invest, 118:294-305.

Biasco et al., 2015, "In vivo tracking of T cells in humans unveils decade-long survival and activity of genetically modified T memory stem cells", Transplantation, 7(273):1-12 and supplementary materials (25 pages).

Bleakley et al., 2015, "Outcomes of acute leukemia patients transplanted with naive T cell-depleted stem cell grafts", J of Clinical Investigation, 125(7):2677-2689.

Blyth et al., Nov. 2011, "BK virus-specific T cells for use in cellular therapy show specificity to multiple antigens and polyfunctional cytokine responses," Transplantation, 92(10):1077-1084.

Bontadini, 2012, "HLA techniques: typing and antibody detection in the laboratory of immunogenetics", Methods, 56(4):471-476.

Brenchley et al., 2003, "Expression of CD57 defines replicative senescence and antigen-induced apoptotic death of CD8+ T cells", Blood, 101:2711-2720.

Burns and Crawford, Sep. 2004, "Epstein-Barr virus-specific cytotoxic T-lymphocytes for adoptive immunotherapy of post-transplant lymphoproliferative disease," Blood Reviews, 18(3):193-209.

Cheng et al., 2012, "Multifactorial heterogeneity of virus-specific T cells and association with the progression of human chronic hepatitis B infection", Science Translational Medicine, 3:128ra142.

Cieri et al., 2013, "IL-7 and IL-15 instruct the generation of human memory stem T cells from naive precursors", Blood, 121(4):573-584.

Cieri et al., 2015, "Generation of human memory stem T cells after haploidentical T-replete hematopoietic stem cell transplantation", Blood, 125(18):2865-2874.

Cobbold et al., Aug. 2005, "Adoptive transfer of cytomegalovirus-specific CTL to stem cell transplant patients after selection by HLA-peptide tetramers," The Journal of Experimental Medicine, 202(3):379-386.

Comoli et al., Apr. 2002, "Infusion of autologous Epstein-Barr virus (EBV)-specific cytotoxic T cells for prevention of EBV-related lymphoproliferative disorder in solid organ transplant recipients with evidence of active virus replication," Blood, 99(7):2592-2598.

Cornberg et al., 2006, "Narrowed TCR repertoire and viral escape as a consequence of heterologous immunity", J Clin Invest, 116(5):1443-1456.

Cortivo et al., Nov. 2012, "Anti CMV and/or anti adenovirus IFN-g-positive CD4+ CD8+ T lymphocytes for treatment of viral infections after allogeneic HSC transplantation: first results," Blood, 120(21):1906.

Doubrovina et al., Nov. 2007, "Leukemia-reactive cytotoxic CD8+ and CD4+ T-cells specific for novel WT-1 epitopes are generated in vitro by sensitization with overlapping pentadecapeptides (15-mers) spanning the wilms tumor protein," Blood, 110 (11).

Doubrovina et al., Mar. 2012, "Adoptive immunotherapy with unselected or EBV-specific T cells for biopsy-proven EBV+ lymphomas after allogeneic hematopoietic cell transplantation," Blood, 119(11):2644-2656 (Published online Dec. 2, 2011).

Doubrovina et al., Aug. 2012, "Mapping of novel peptides of WT-1 and presenting HLA alleles that induce epitope-specific HLA-restricted T cells with cytotoxic activity against WT-1(+) leukemias," Blood, 120(8):1633-1646 (Published online May 23, 2012).

Doubrovina et al., Nov. 2004, "In vitro stimulation with WT1 peptide-loaded Epstein-Barr virus-positive B cells elicits high frequencies of WT1 peptide-specific T cells with in vitro and in vivo tumoricidal activity," Clinical Cancer Research, 10(21):7207-7219.

Dunn, 2011, "Human leucocyte antigen typing: techniques and technology, a critical appraisal", Int J Immunogenet, 38(6):463-473.

Einsele et al., Jun. 2002, "Infusion of cytomegalovirus (CMV)-specific T cells for the treatment of CMV infection not responding to antiviral chemotherapy," Blood, 99(11):3916-3922.

Eiz-Vesper et al., Jan. 2013, "Adoptive T-cell immunotherapy from third-party donors: characterization of donors and set up of a T-cell donor registry," Frontiers in Immunology, 3:410.

Erlich, 2012, "HLA DNA typing: past, present, and future", Tissue Antigens, 80:1-11.

Feuchtinger et al., Nov. 2010, "Adoptive transfer of pp65-specific T cells for the treatment of chemorefractory cytomegalovirus disease or reactivation after haploidentical and matched unrelated stem cell transplantation," Blood, 116(20):4360-4367 (Published online Jul. 12, 2010).

Flomenberg et al., 2004, "Impact of HLA class I and class II high-resolution matching on outcomes of unrelated donor bone

(56) References Cited

OTHER PUBLICATIONS marrow transplantation: HLA-C mismatching is associated with a strong adverse effect on transplantation outcome", Blood, 104(7):1923-1930.
Gabriel et al., 2014, "HLA typing by next-generation sequencing—getting closer to reality", Tissue Antigens, 83(2):65-75.
Gahn et al., Jan. 2002, "Immunotherapy to reconstitute immunity to DNA viruses," Seminars in Hematology, 39(1):41-47.
Gandhi et al., May 2007, "Immunity, homing and efficacy of allogeneic adoptive immunotherapy for posttransplant lymphoproliferative disorders," American Journal of Transplantation, 7(5):1293-1299 (Published online Apr. 8, 2007).
Gattinoni et al., 2011, "A human memory T-cell subset with stem cell-like properties", Nature Medicine, 17(10):1290-1298.
Gattinoni et al., 2013, "Moving T memory stem cells to the clinic", Blood Journal, 121(4):567-568.
Gerdemann et al., Jan. 2013, "Immunotherapeutic strategies to prevent and treat human herpesvirus 6 reactivation after allogeneic stem cell transplantation," Blood, 121(1):207-218.
Gottschalk et al., Jan. 2015, "Adoptive T-cell immunotherapy," Current Topics in Microbiology and Immunology, 391:427-454.
Hanley et al., 2015, "CMV-specific T cells generated from naïve T cells recognize atypical epitopes and may be protective in vivo", Science Translation Medicine, Supplemental Materials 7(285):26 pages.
Haque et al., Oct. 2001, "Complete regression of posttransplant lymphoproliferative disease using partially HLA-matched Epstein Barr virus-specific cytotoxic T cells," Transplantation,72(8): 1399-1402.
Haque et al., Aug. 2007, "Allogeneic cytotoxic T-cell therapy for EBV-positive posttransplantation lymphoproliferative disease: results of a phase 2 multicenter clinical trial," Blood, 110(4):1123-1131 (Published online Apr. 27, 2007).
Haque et al., Aug. 2002, "Treatment of Epstein-Barr-virus-positive post-transplantation lymphoproliferative disease with partly HLA-matched allogeneic cytotoxic T cells," Lancet, 360(9331):436-442.
Holmes-Liew et al., Mar. 2015, "Adoptive T-cell immunotherapy for ganciclovir-resistant CMV disease after lung transplantation," Clinical & Translational Immunology, 4(3):e35.
Hasan et al., Dec. 2014, "Banked, GMP grade third party T-cell lines specific for CMVpp65 epitopes presented by certain prevalent HLA alleles more consistently clear CMV infections in a genetically heterogeneous population of HSCT recipients," Blood, 124(21):309.
Hasan et al., 2014, "Banked, GMP grade third party T-cell lines specific for CMVpp65 epitopes presented by certain prevalent HLA alleles more consistently clear CMV infections in a genetically heterogeneous population of HSCT recipients," meeting abstract for the 56th American Society of Hematology (ASH) Annual Meeting and Exposition held in San Francisco, California, Dec. 6-9, 2014, first published online on Nov. 6, 2014.
Hasan et al., Feb. 2014, "Generation and characterization of a third party GMP grade bank of CMV specific T-cells for adoptive immunotherapy of CMV infections in recipients of HSCT from cord blood or seronegative donors," Biology of Blood and Marrow Transplantation, 20(2):S131-S132.
Hasan, "Banked, GMP grade third party T-cell lines specific for CMVpp65 epitopes presented by certain prevalent HLA alleles more consistently clear CMV infections in a genetically heterogeneous population of HSCT recipients," slide presentation on Dec. 8, 2014 at the 56th ASH Annual Meeting held Dec. 6-9, 2014, San Francisco, California, United States, 22 pages.
Hasan et al., Nov. 15, 2013, "Generation and characterization of a third party GMP grade bank of CMV specific T-cells for adoptive immunotherapy of CMV infections in recipients of HSCT from cord blood or seronegative donors," Blood, 122(21):2021.
Hasan et al., Aug. 2009, "A panel of artificial APCs expressing prevalent HLA alleles permits generation of cytotoxic T cells specific for both dominant and subdominant viral epitopes for adoptive therapy," The Journal of Immunology, 183(4):2837-2850 (Published online Jul. 27, 2009).

Heslop et al., Feb. 2010, "Long-term outcome of EBV-specific T-cell infusions to prevent or treat EBV-related lymphoproliferative disease in transplant recipients," Blood, 115(5):925-935 (Published online Oct. 30, 2009).
Hintzen et al., 1993, "Regulation of CD27 expression on subsets of mature T-lymphocytes", J Immunol, 151(5):2426-2435.
Humar et al., Dec. 2009, "Cytomegalovirus in solid organ transplant recipients," American Journal of Transplantation, 9(Suppl 4):S78-S86.
Kaech et al., 2003, "Selective expression of the interleukin 7 receptor identifies effector CD8 T cells that give rise to long-lived memory cells", Nat Immunol 4: 1191-1198.
Kawakami et al., Oct. 2005, "A case of immune recovery vitritis induced by donor leukocyte infusion for the treatment of cytomegalovirus retinitis," European Journal of Haematology, 75(4):352-354.
Khan et al., 2007, "T cell recognition patterns of immunodominant cytomegalovirus antigens in primary and persistent infection", J Immunol, 178:4455-4465.
Khanna et al., Aug. 1999, "Activation and adoptive transfer of Epstein-Barr virus-specific cytotoxic T cells in solid organ transplant patients with posttransplant lymphoproliferative disease," Proceedings of the National Academy of Sciences of the United States of America, 96(18):10391-10396.
Koehne et al., Jul. 2000, "Rapid selection of antigen-specific T lymphocytes by retroviral transduction," Blood, 96(1):109-117.
Koehne et al., Mar. 2002, "Quantitation, selection, and functional characterization of Epstein-Barr virus-specific and alloreactive T cells detected by intracellular interferon-gamma production and growth of cytotoxic precursors," Blood, 99(5):1730-1740.
Koehne et al., Sep. 2015, "Immunotherapy with donor T cells sensitized with overlapping pentadecapeptides for treatment of persistent cytomegalovirus infection or viremia," Biology of Blood and Marrow Transplantation, 21(9):1663-1678 (Published online May 29, 2015).
Kogler et al., 2005, "High-resolution HLA typing by sequencing for HLA-A, -B, -C, -DR, -DQ in 122 unrelated cord blood/patient pair transplants hardly improves long-term clinical outcome", Bone Marrow Transplant, 36(12):1033-1041.
Kunert et al., 2013, "TCR-Engineered T Cells Meet New Challenges to Treat Solid Tumors: Choice of Antigen, T Cell Fitness, and Sensitization of Tumor Milieu", Front Immunol., 192:5039-5049.
Lange et al., 2014, "Cost-efficient high-throughput HLA typing by MiSeq amplicon sequencing", BMC Genomics, 15:63.
Lank et al., 2012, "Ultra-high resolution HLA genotyping and allele discovery by highly multiplexed cDNA amplicon pyrosequencing", BMC Genomics, 13:378.
Lee et al., 2007, "High-resolution donor-recipient HLA matching contributes to the success of unrelated donor marrow transplantation", Blood, 110:4576-4583.
Leen et al, Jun. 2013, "Multicenter study of banked third-party virus-specific T cells to treat severe viral infections after hematopoietic stem cell transplantation," Blood, 121(26):5113-5123 (Published online Apr. 22, 2013).
Leen et al., Oct. 2006, "Monoculture-derived T lymphocytes specific for multiple viruses expand and produce clinically relevant effects in immunocompromised individuals," Nature Medicine, 12(10):1160-1166 (Published online Sep. 24, 2006).
Lewis et al., 1967, "The effect of cooling regimens on the transplantation potential of marrow", Transfusion, 7(1):17-32.
Li et al., 2012, "Determinants of public T cell responses", Cell Res, 22:33-42.
Lidehall et al., 2005, "T cell control of primary and latent cytomegalovirus infections in healthy subjects", J Clin Immunol 25:473-481.
Linner et al., 1986, "A new technique for removal of amorphous phase tissue water without ice crystal damage: a preparative method for ultrastructural analysis and immunoelectron microscopy", J Histochem Cytochem, 34:1123-1135.
Livesey and Linner, 1987, "Cryofixation taking on a new look", Nature, 327:255-256.

(56) References Cited

OTHER PUBLICATIONS

Louis et al., Nov.-Dec. 2010, "Adoptive transfer of EBV-specific T cells results in sustained clinical responses in patients with locoregional nasopharyngeal carcinoma," Journal of Immunotherapy, 33(9):983-990.

Lucas et al., Mar. 1996, "The development of cellular immunity to Epstein-Barr virus after allogeneic bone marrow transplantation," Blood, 87(6):2594-2603.

Lugli et al., 2013, "Identification, isolation and in vitro expansion of human and nonhuman primate T stem cell memory cells", Nature Protocols, 8(1):1750-2799.

Macesic et al., Mar. 2015, "Adoptive T cell immunotherapy for treatment of ganciclovir-resistant cytomegalovirus disease in a renal transplant recipient," American Journal of Transplantation, 15(3):827-832 (Published online Feb. 3, 2015).

Mahnke et al., 2013, "The who's who of T-cell differentiation: human memory Tcell subsets", Eur. J. Immunol., 43:2797-2809.

Mazur et al., 1977, "The role of intracellular freezing in the death of cells cooled at supraoptimal rates", Cryobiology, 14:251-272.

Mazur et al., 1970, "Cryobiology: the freezing of biological systems", Science, 168:939-949.

Meyer-Olson et al., 2004, "Limited T cell receptor diversity of HCV-specific T cell responses is associated with CTL escape", J Exp Med, 200:307-319.

Micklethwaite et al., Jun. 2007, "Ex vivo expansion and prophylactic infusion of CMV-pp65 peptide-specific cytotoxic T-lymphocytes following allogeneic hematopoietic stem cell transplantation," Biology of Blood and Marrow Transplantation, 13(6):707-714 (Published Apr. 6, 2007).

Miles et al., 2011, "Bias in the αβ T-cell repertoire: implications for disease pathogenesis and vaccination", Immunol Cell Biol, 89(3):375-387.

Neller et al., 2015, "Naive CD8+ T-cell precursors display structured TCR repertoires and composite antigen-driven selection dynamics", Immunology and Cell Biology, 93(7):625-633.

Nguyen et al., 2014, "Recognition of distinct cross-reactive virus-specific CD8+ T cells reveals a unique TCR signature in a clinical setting", J Immunol, 192(11):5039-5049.

Papadopoulou et al., Jun. 2014, "Activity of broad-spectrum T cells as treatment for AdV, EBV, CMV, BKV, and HHV6 infections after HSCT," Science Translational Medicine, 6(242):242ra83.

Picker et al., Aug. 1995, "Direct demonstration of cytokine synthesis heterogeneity among human memory/effector T cells by flow cytometry," Blood, 86(4):1408-1419.

Prockop et al., Dec. 2014, "Third party donor derived CMV specific T cells for the treatment of refractory CMV viremia and disease after hematopoietic stem cell transplant," Blood, 124(21):184.

Prockop et al., 2014, "Third party donor derived CMV specific T cells for the treatment of refractory CMV viremia and disease after hematopoietic stem cell transplant," meeting abstract for the 56th American Society of Hematology (ASH) Annual Meeting and Exposition held in San Francisco, California, Dec. 6-9, 2014, first published online on Nov. 6, 2014.

Prockop et al., Feb. 2014, "Third party donor derived EBV specific T cells for the treatment of refractory EBV-related post-transplant lymphomas," Biology of Blood and Marrow Transplantation, 20(2):S49-S50.

Prockop et al., 2015, "Successful treatment of refractory CMV chorioretinitis and meningoencephalitis with adoptive transfer of third party CMVpp65 specific T-cell lines," meeting abstract for the 57th American Society of Hematology (ASH) Annual Meeting and Exposition held in Orlando, Florida, Dec. 5-8, 2015, first published online on Nov. 5, 2015.

Qasim et al., May 2013, "Interferon-? capture T cell therapy for persistent Adenoviraemia following allogeneic haematopoietic stem cell transplantation," British Journal of Haematology, 161(3):449-452 (Published online Feb. 22, 2013).

Ramos et al., Jan. 2013, "Human papillomavirus type 16 E6/E7-specific cytotoxic T lymphocytes for adoptive immunotherapy of HPV-associated malignancies," Journal of Immunotherapy, 36(1):66-76.

O'Reilly, 2014, meeting abstract for the oral presentation on Oct. 31, 2014 at the 76th Annual Meeting of the Japanese Society of Hematology, held Oct. 31-Nov. 2, 2014, Osaka, Japan.

O'Reilly et al., Sep. 2011, "Novel strategies for adoptive therapy following HLA disparate transplants," Best Practice & Research Clinical Haematology, 24(3):381-391.

O'Reilly et al., May 2007, "Adoptive transfer of antigen-specific T-cells of donor type for immunotherapy of viral infections following allogeneic hematopoietic cell transplants", Immunologic Research, 38(1-3):237-250.

O'Reilly et al., Jun. 2010, "Adoptive transfer of unselected or leukemia-reactive T-cells in the treatment of relapse following allogeneic hematopoietic cell transplantation," Seminars in Immunology, 22(3):162-172 (Published online May 26, 2010).

O'Reilly et al., Jun. 2015, "T-cell depleted allogeneic hematopoietic cell transplants as a platform for adoptive therapy with leukemia selective or virus-specific T-cells," Bone Marrow Transplant, 50(Suppl 2):S43-S50.

Park et al., 2011, "Treating cancer with genetically engineered T cells", Trends Biotechnol, 29(11):550-557.

Peggs et al., Oct. 2003, "Adoptive cellular therapy for early cytomegalovirus infection after allogeneic stem-cell transplantation with virus-specific T-cell lines," Lancet, 362(9393):1375-1377.

Prockop, "Third party donor derived EBV specific T cells for the treatment of refractory lymphoma in immunodeficient recipients," slide presentation on Mar. 1, 2014 at the ASBMT 2014 BMT Tandem Meetings held Feb. 26-Mar. 2, 2014, Grapevine, Texas, United States, 22 pages.

Prockop, "Adoptive immunotherapy with banked virus specific 3rd party donor T?cells for CMV infections and EBV LPD complicating hematopoietic cell transplants," slide presentation on Oct. 31, 2014 at the 76th Annual Meeting of the Japanese Society of Hematology, held Oct. 31-Nov. 2, 2014, Osaka, Japan, 43 pages.

Prockop, "Third party donor T cells for the treatment of CMV infection and EBV lymphoma in immunodeficient patients," slide presentation on May 22, 2014 at the 9th Meeting of the EBMT Pediatric Diseases WP, held May 21-23, 2014, Jerusalem, Israel, 47 pages.

Prockop, "3rd party CMV specific T cells for the treatment of refractory CMV viremia and disease after HSCT," slide presentation on Dec. 7, 2014 at the 56th ASH Annual Meeting held Dec. 6-9, 2014, San Francisco, California, United States, 27 pages.

Prockop et al., "Epstein-Barr virus-specific cytotoxic T lymphocytes for treatment of rituximab-refractory Epstein-Barr virus-associated lymphoproliferative disorder," meeting abstract for the 2015 AACR Anual Meeting held Apr. 18-22, 2015, Philadelphia, Pennsylvania, United States, published Mar. 18, 2015, 2 pages.

Prockop, "Epstein-Barr virus (EBV)-specific cytotoxic T lymphocytes (EBV-CTLs) for treatment of rituximab-refractory EBV-associated lymphoproliferative disorder (EBV-LPD)," slide presentation on Apr. 19, 2015 at the 2015 AACR Anual Meeting held Apr. 18-22, 2015, Philadelphia, Pennsylvania, United States, 25 pages.

Prockop et al., "Banked EBV-specific T-cells from HLA-partially matched normal donors induce durable remissions of rituximab refractory EBV+ B-cell lymphomas post hematopoietic and organ allografts," meeting abstract for the 2015 ASCO Anual Meeting held May 29-Jun. 2, 2015, Chicago, Illinois, United States, published May 20, 2015 (the same abstract was published online early on May 13, 2015), 2 pages.

Prockop, "Banked EBV-specific T-cells from HLA-partially matched normal donors induce durable remissions of rituximab refractory EBV+ B-cell lymphomas post hematopoietic and organ allografts," slide presentation on Jun. 1, 2015 at the 2015 ASCO Anual Meeting held May 29-Jun. 2, 2015, Chicago, Illinois, United States, 18 pages.

Pulko et al., 2016, "Human memory T cells with a naive phenotype accumulate with aging and respond to persistent viruses", Nature Immunology, 17(8):966-976.

(56) References Cited

OTHER PUBLICATIONS

Rapatz et al., 1968, "Preservation of erythrocytes in blood containing various cryoprotective agents, frozen at various rates and brought to a given final temperature", Cryobiology, 5(1):18-25.
Roberto et al., 2015, "Role of naive-derived T memory stem cells in T-cell reconstitution following allogeneic transplantation", Blood, 125(18):2855-2864.
Rooney et al., Sep. 1998, "Infusion of cytotoxic T cells for the prevention and treatment of Epstein-Barr virus-induced lymphoma in allogeneic transplant recipients," Blood, 92(5):1549-1555.
Rooney et al., Jan. 1995, "Use of gene-modified virus-specific T lymphocytes to control Epstein-Barr-virus-related lymphoproliferation," Lancet, 345(8941):9-13.
Rowe and Rinfret, 1962, "Bone Marrow Transplantation and Irradiation Protection", Blood, abstract only, 20(5):636.
Rowe AW, 1966, "Biochemical aspects of cryoprotective agents in freezing and thawing", Cryobiology, 3(1):12-18.
Sadelain et al., 2013, "The basic principles of chimeric antigen receptor design", Cancer Discovery, 3:388-398.
Schmueck-Henneresee et al., 2015, "Peripheral blood-derived virus-specific memory stem T cells mature to functional effector memory subsets with self-renewal potency", J Immunol, 194(11):5559-5567.
Schmitt et al., Mar. 2011, "Adoptive transfer and selective reconstitution of streptamer-selected cytomegalovirus-specific CD8+ T cells leads to virus clearance in patients after allogeneic peripheral blood stem cell transplantation," Transfusion, 51(3):591-599 (Published online Dec. 6, 2010).
Sharpe and Mount, 2015, "Genetically modified T cells in cancer therapy: opportunities and challenges", Dis Model Mech, 8:337-350.
Sili et al., Jan. 2012, "Production of good manufacturing practice-grade cytotoxic T lymphocytes specific for Epstein-Barr virus, cytomegalovirus and adenovirus to prevent or treat viral infections post-allogeneic hematopoietic stem cell transplant," Cytotherapy, 14(1):7-11.
Song et al., 2012, "CD27 costimulation augments the survival and antitumor activity of redirected human T cells in vivo", Blood, 119(3):696-706.
Stauss et al., 2015, "Cancer gene therapy with T cell receptors and chimeric antigen receptors.", Curr Opin Pharmacol, 24:113-118.
Stone et al., 2012, "T cell receptor engineering", Methods Enzymol, 503:189-222.
Straathof et al., Mar. 2005, "Treatment of nasopharyngeal carcinoma with Epstein-Barr virus—specific T lymphocytes," Blood, 105(5):1898-1904 (Published online Nov. 12, 2004).
Sukdolak et al., Oct. 2013, "CMV-, EBV- and ADV-specific T cell immunity: screening and monitoring of potential third-party donors to improve post-transplantation outcome," Biology of Blood and Marrow Transplantation, 19(10):1480-1492 (Published online Jul. 23, 2013).
Szabolcs, Paul, 2011, "T-lymphocyte recovery and function after cord blood transplantation", Immunol. Res., 49:56-69.
Trivedi et al., Apr. 2005, "Generation of CMV-specific T lymphocytes using protein-spanning pools of pp65-derived overlapping pentadecapeptides for adoptive immunotherapy," Blood, 105(7):2793-2801 (Published online Oct. 28, 2004).
Trautmann et al., 2005, "Selection of T cell clones expressing high-affinity public TCRs within Human cytomegalovirus-specific CD8 T cell responses", J Immun., 175:6123-6132.
Tscharke et al., 2015, "Sizing up the key determinants of the CD8(+) T cell response", Nat Rev Immunol, 15:705-716.
Tse and Kwong, Jan. 2015, "Epstein Barr virus-associated lymphoproliferative diseases: the virus as a therapeutic target," Experimental & Molecular Medicine, 47:e136.
Uhlin et al., Oct. 2012, "Rapid salvage treatment with virus-specific T cells for therapy-resistant disease," Clinical Infectious Diseases, 55(8):1064-1073 (Published online Jul. 17, 2012).
Waldrop et al., Apr. 1997, "Determination of antigen-specific memory/effector CD4+ T cell frequencies by flow cytometry: evidence for a novel, antigen-specific homeostatic mechanism in HIV-associated immunodeficiency," Journal of Clinical Investigation, 99(7):1739-1750.
Walter et al., Oct. 1995, "Reconstitution of cellular immunity against cytomegalovirus in recipients of allogeneic bone marrow by transfer of T-cell clones from the donor," The New England Journal of Medicine, 333(16):1038-1044.
Wang et al., 2011, "Engraftment of human central memory-derived effector CD8+ T cells in immunodeficient mice", Blood, 117:1888-1898.
Wang et al., 2012, "T cell receptor αβ diversity inversely correlates with pathogen-specific antibody levels in human cytomegalovirus infection.", Sci Translational Medicine, 4:128ra142.
Welsh et al., 2010, "Heterologous immunity between viruses", Immunol Rev, 235:244-266.
Wensveen et al., 2010, "Apoptosis threshold set by Noxa and Mcl-1 after T cell activation regulates competitive selection of high-affinity clones", Immunity, 32:754-765.
Wilkie et al., Jul.-Aug. 2004, "Establishment and characterization of a bank of cytotoxic T lymphocytes for immunotherapy of epstein-barr virus-associated diseases," Journal of Immunotherapy, 27(4):309-316.
Wolfl et al., 2007, "Activation-induced expression of CD137 permits detection, isolation, and expansion of the full repertoire of CD8+ T cells responding to antigen without requiring knowledge of epitope specificities", Blood, 110:201-210.
Xu et al., 2015, "The roles of stem cell memory T cells in hematological malignancies", J of Hematology & Oncology, 8(113):5 pages.
Yang et al., 2015, "Structural Basis for Clonal Diversity of the Public T Cell Response to a Dominant Human Cytomegalovirus Epitope", J Biol Chem, 290:29106-29119.
O'Reilly et al., Sep. 2016, "Virus-specific T-cell banks for 'off the shelf' adoptive therapy of refractory infections," Bone Marrow Transplantation, 51(9):1163-1172 (published online on Apr. 4, 2016).
Lugli et al., Jan. 2013 "Identification, isolation and in vitro expansion of human and nonhuman primate T stem cell memory cells," Nat Protoc. 8(1):33-42.

\* cited by examiner

Figure 6G

GENERATION AND USE IN ADOPTIVE IMMUNOTHERAPY OF STEM CELL-LIKE MEMORY T CELLS

CROSS-REFERENCE TO RELATED APPLICATIONS

This application is a national stage of International Patent Application No. PCT/US2017/052846, filed Sep. 22, 2017, which claims the benefit of U.S. Provisional Application No. 62/399,311, filed Sep. 23, 2016, which is incorporated by reference herein in its entirety.

GOVERNMENT RIGHTS STATEMENT

This invention was made with government support under CA023766 awarded by National Institutes of Health. The government has certain rights in the invention.

REFERENCE TO SEQUENCE LISTING SUBMITTED ELECTRONICALLY

This application incorporates by reference a Sequence Listing submitted with this application as a text file entitled "Seqlisting_14259-034-228.txt" created on Sep. 12, 2017 and having a size of 4.57 kilobytes.

1. FIELD

Provided herein are methods of generating antigen-specific T cells for therapeutic administration to a human patient having or suspected of having a pathogen or cancer, utilizing stem cell-like memory T cells ($T_{SCM}$ cells). Also disclosed are antigen-specific T cells generated by such methods, and methods of treating a human patient using such antigen-specific T cells.

2. BACKGROUND

The characteristics of the T cells that are selected for expansion and adoptive transfer have been identified as a critical factor that determines the persistence of transferred cells. Antigen-specific T cells in the presence of infections or cancer can expand and differentiate into effector T cells devoted to rapidly clearing of the pathogens as well as memory T cells that can persist long-term and defend against recurrence of disease. The memory T cell compartment is heterogeneous and encompasses multiple subsets with distinctive properties. Current evidence indicates that central memory T cells ($T_{CM}$ cells) that express high levels of CD62L and CCR7 are less differentiated, while CD62L⁻ CCR7⁻ effector memory T cells ($T_{EM}$ cells) represent committed progenitor cells that undergo terminal differentiation (Berger et al., 2008, J Clin Invest 118:294-305). Furthermore, studies in mice and nonhuman primates have shown that infused T cells that are derived from the $T_{CM}$ population exhibit greater replicative potential in response to antigen and prolonged in vivo persistence compared with those derived from the $T_{EM}$ population (Berger et al., 2008, J Clin Invest 118:294-305; Wang et al., 2011, Blood 117:1888-1898). Recently, the spectrum of immunological memory has been extended with the identification of stem cell-like memory T cells ($T_{SCM}$ cells) that express CD45RA, CCR7 and CD62L, like naive T cells, but also express CD95. Human $T_{SCM}$ cells have been expanded in vitro (Gattinoni et al., 2011, Nat Med 17:1290-1297; Cieri et al., 2013, Blood 121:573-584). When compared with other memory T cell populations, human $T_{SCM}$ cells have exhibited increased proliferative capacity. $T_{SCM}$ cells transduced to express a mesothelin-specific chimeric antigen receptor have also exhibited greater proliferation and superior antitumor responses following adoptive transfer in a humanized mouse model (Gattinoni et al., 2011, Nat Med 17:1290-1297). While $T_{SCM}$ cells can differentiate into $T_{CM}$, $T_{EM}$ and effector T cells, they also have a marked potential for self-renewal as shown by serial transplantation experiments (Cieri et al., 2013, Blood 121:573-584). Because of these attributes, $T_{SCM}$ cells have attracted considerable interests as a potential critical reservoir of antigen-specific T cells for reconstituting immunity following human allogeneic hematopoietic cell transplants (allo HCT) (Cieri et al., 2013, Blood 121:573-584; Xu et al., 2015, J Hematol Oncol 8:113; Biasco et al., 2015, Sci Transl Med 7:273ra213; Roberto et al., 2015, Blood 125:2855-2864). Indeed, analyses of T cell receptor CDR3 sequences have shown that $T_{SCM}$ cells undergo marked proliferation and clonal diversification early after allo HCT (Roberto et al., 2015, Blood 125:2855-2864; Cieri et al., 2015, Blood 125:2865-2874). Furthermore, $T_{SCM}$ cell clones, distinguished by retroviral vector insertion sites, may resist in humans for up to 12 years post infusion (Biasco et al., 2015, Sci Transl Med 7:273ra213). The low frequency of antigen-specific $T_{SCM}$ cells has limited their detailed characterization (Schmueck-Henneresse et al., 2015, J Immunol 194:5559-5567). Furthermore, the contribution of different memory subsets to the maintenance of the overall memory compartment of antigen-specific T cells has not been fully elucidated.

Citation of a reference herein shall not be construed as an admission that such is prior art to the present disclosure.

3. SUMMARY OF THE INVENTION

The present invention provides methods of generating antigen-specific T cells for therapeutic administration to a human patient having or suspected of having a pathogen or cancer, utilizing stem cell-like memory T cells ($T_{SCM}$ cells). Also disclosed are antigen-specific T cells generated by such methods, and methods of treating a human patient using such antigen-specific T cells.

In one aspect, provided herein are methods of generating a population of cells comprising antigen-specific T cells for therapeutic administration to a human patient having or suspected of having a pathogen or cancer, comprising: (a) ex vivo sensitizing a population of human blood cells to one or more antigens of the pathogen or cancer over a period of time in culture, wherein at the initiation of said period of time, the population of human blood cells contains at least 50% stem cell-like memory T cells ($T_{SCM}$ cells); and (b) cryopreserving (i) the ex vivo sensitized population of human blood cells, or (ii) cells derived therefrom that comprise antigen-specific T cells recognizing the one or more antigens of the pathogen or cancer; thereby producing said population of cells comprising antigen-specific T cells.

In certain embodiments, the method of generating a population of cells comprising antigen-specific T cells further comprises, after the step of cryopreserving, steps of thawing and optionally expanding in culture the ex vivo sensitized population of human blood cells or cells derived therefrom.

In specific embodiments, the aforementioned period of time in culture (termed herein "the Sensitization Culture Time;" i.e., the culture time period over which sensitization occurs) is in the range of 9-21 days. In a specific embodiment, the Sensitization Culture Time is in the range of 9-14 days. In another specific embodiment, the Sensitization Culture Time is 14 days.

In specific embodiments, the ex vivo sensitizing step comprises co-culturing the population of human blood cells with one or more immunogenic peptides or proteins derived from the one or more antigens. In specific embodiments, the ex vivo sensitizing step comprises co-culturing the population of human blood cells with antigen presenting cells that present the one or more antigens.

The antigen presenting cells used in the ex vivo sensitizing step can be any antigen presenting cells suitable for presenting the one or more antigens, such as dendritic cells, cytokine-activated monocytes, peripheral blood mononuclear cells (PBMCs), Epstein-Barr virus-transformed B-lymphoblastoid cell line cells (EBV-BLCL cells), or artificial antigen presenting cells (AAPCs). In a specific embodiment, the antigen presenting cells are AAPCs.

In some embodiments, the antigen presenting cells are loaded with one or more immunogenic peptides or proteins derived from the one or more antigens. In other embodiments, the antigen presenting cells are genetically engineered to recombinantly express one or more immunogenic peptides or proteins derived from the one or more antigens.

In some embodiments, the one or more immunogenic peptides or proteins are a pool of overlapping peptides derived from the one or more antigens. In specific embodiments, the pool of overlapping peptides is a pool of overlapping pentadecapeptides. In other embodiments, the one or more immunogenic peptides or proteins are one or more proteins derived from the one or more antigens.

In some embodiments, the population of cells comprising antigen-specific T cells, as described herein, comprises antigen-specific T cells that endogenously express a public T cell receptor (TCR) recognizing the one or more antigens. In other embodiments, the population of cells comprising antigen-specific T cells, as described herein, comprises antigen-specific T cells that recombinantly express a public TCR recognizing the one or more antigens. In specific embodiments, the method of generating a population of cells comprising antigen-specific T cells, as described herein, further comprises transducing the population of human blood cells with a nucleic acid encoding a public TCR (e.g., at a time when the population of human blood cells has been cultured for 3-5 days). In a specific embodiment wherein the one or more antigens is cytomegalovirus (CMV) pp65, the public TCR comprises a β-chain comprising a variable domain, which comprises a complementarity determining region (CDR)3 of CASSPQTGASYGYTF (SEQ ID NO:3). In another specific embodiment wherein the one or more antigens is CMV pp65, the public TCR comprises a β-chain comprising a variable domain, which comprises a CDR3 of CASSPKTGAVYGYTF (SEQ ID NO:4).

In certain embodiments, the population of cells comprising antigen-specific T cells, as described herein, comprises antigen-specific T cells that recombinantly express a chimeric antigen receptor (CAR) recognizing the one or more antigens. In specific embodiments, the method of generating a population of cells comprising antigen-specific T cells, as described herein, further comprises transducing the population of human blood cells with a nucleic acid encoding a CAR (e.g., at a time when the population of human blood cells has been cultured for 3-5 days).

In another aspect, provided herein are methods of generating a population of cells comprising antigen-specific T cells for therapeutic administration to a human patient having or suspected of having a pathogen or cancer, comprising transducing a population of human blood cells with a nucleic acid encoding a public TCR recognizing one or more antigens of the pathogen or cancer at a time when the population of human blood cells has been cultured for 3-5 days, wherein the population of human blood cells contains at least 50% $T_{SCM}$ cells; thereby producing said population of cells comprising antigen-specific T cells. In a specific embodiment wherein the one or more antigens is CMV pp65, the public TCR comprises a β-chain comprising a variable domain, which comprises a CDR3 of CASSPQTGASYGYTF (SEQ ID NO:3). In another specific embodiment wherein the one or more antigens is CMV pp65, the public TCR comprises a β-chain comprising a variable domain, which comprises a CDR3 of CASSPKTGAVYGYTF (SEQ ID NO:4). In specific embodiments, the method of generating a population of cells comprising antigen-specific T cells further comprises, after the step of transducing, a step of cryopreserving the transduced population of human blood cells or cells derived therefrom. In a specific embodiment, the method of generating a population of cells comprising antigen-specific T cells further comprises, after the step of cryopreserving, steps of thawing and optionally expanding in culture the transduced population of human blood cells or cells derived therefrom.

In another aspect, provided herein are methods of generating a population of cells comprising antigen-specific T cells for therapeutic administration to a human patient having or suspected of having a CMV infection, comprising transducing a population of human blood cells with a nucleic acid encoding a public TCR recognizing CMV pp65 at a time when the population of human blood cells has been cultured for 3-5 days, wherein the public TCR comprises a β-chain comprising a variable domain, which comprises a CDR3 of CASSPQTGASYGYTF (SEQ ID NO:3), and wherein the population of human blood cells contains at least 50% $T_{SCM}$ cells; thereby producing said population of cells comprising antigen-specific T cells. In specific embodiments, the method of generating a population of cells comprising antigen-specific T cells further comprises, after the step of transducing, a step of cryopreserving the transduced population of human blood cells or cells derived therefrom. In a specific embodiment, the method of generating a population of cells comprising antigen-specific T cells further comprises, after the step of cryopreserving, steps of thawing and optionally expanding in culture the transduced population of human blood cells or cells derived therefrom.

In another aspect, provided herein are methods of generating a population of cells comprising antigen-specific T cells for therapeutic administration to a human patient having or suspected of having a CMV infection, comprising transducing a population of human blood cells with a nucleic acid encoding a public TCR recognizing CMV pp65 at a time when the population of human blood cells has been cultured for 3-5 days, wherein the public TCR comprises a β-chain comprising a variable domain, which comprises a CDR3 of CASSPKTGAVYGYTF (SEQ ID NO:4), and wherein the population of human blood cells contains at least 50% $T_{SCM}$ cells; thereby producing said population of cells comprising antigen-specific T cells. In specific embodiments, the method of generating a population of cells comprising antigen-specific T cells further comprises, after the step of transducing, a step of cryopreserving the transduced population of human blood cells or cells derived therefrom. In a specific embodiment, the method of generating a population of cells comprising antigen-specific T cells further comprises, after the step of cryopreserving, steps of thawing and optionally expanding in culture the transduced population of human blood cells or cells derived therefrom.

In another aspect, provided herein are methods of generating a population of cells comprising antigen-specific T cells for therapeutic administration to a human patient having or suspected of having a pathogen or cancer, comprising transducing a population of human blood cells with a nucleic acid encoding a CAR recognizing one or more antigens of the pathogen or cancer at a time when the population of human blood cells has been cultured for 3-5 days, wherein the population of human blood cells contains at least 50% $T_{SCM}$ cells; thereby producing said population of cells comprising antigen-specific T cells. In specific embodiments, the method of generating a population of cells comprising antigen-specific T cells further comprises, after the step of transducing, a step of cryopreserving the transduced population of human blood cells or cells derived therefrom. In a specific embodiment, the method of generating a population of cells comprising antigen-specific T cells further comprises, after the step of cryopreserving, steps of thawing and optionally expanding in culture the transduced population of human blood cells or cells derived therefrom.

The population of human blood cells used in accordance with the methods of generating a population of cells comprising antigen-specific T cells described herein contains at least 50% $T_{SCM}$ cells. In a specific embodiment, the population of human blood cells contains at least 90% $T_{SCM}$ cells. In another specific embodiment, the population of human blood cells contains at least 95% $T_{SCM}$ cells. In another specific embodiment, the population of human blood cells contains at least 99% $T_{SCM}$ cells. In another specific embodiment, the population of human blood cells contains 100% $T_{SCM}$ cells.

In certain embodiments, the population of human blood cells contains less than 10% $T_N$ cells. In a specific embodiment, the population of human blood cells contains less than 5% $T_N$ cells. In another specific embodiment, the population of human blood cells contains less than 1% $T_N$ cells. In another specific embodiment, the population of human blood cells contains no $T_N$ cells.

In certain embodiments, the method of generating a population of cells comprising antigen-specific T cells described herein further comprises a step of deriving the population of human blood cells from a human cell sample. In specific embodiments, the deriving step comprises enriching for $T_{SCM}$ cells from the human cell sample. In a specific embodiment, the enriching step comprises selecting for cells that are $CD3^+CD62L^+CD45RO^-CD95^+$. In some embodiments, the step of deriving the population of human blood cells from a human cell sample comprises sorting $T_{SCM}$ cells from the human cell sample by fluorescence-activated cell sorting (FACS).

In preferred embodiments, the population of human blood cells is derived from a human donor that is seropositive for the one or more antigens.

In certain embodiments, the population of cells comprising antigen-specific T cells, as described herein, lacks substantial cytotoxicity in vitro toward antigen presenting cells that are not loaded with or genetically engineered to express one or more peptides or proteins derived from the one or more antigens.

In specific embodiments of the methods of generating a population of cells comprising antigen-specific cells described herein, the ex vivo sensitizing step comprises ex vivo sensitizing the population of human blood cells to one or more antigens of the pathogen. The pathogen can be a virus, bacterium, fungus, helminth or protist. In some embodiments, the pathogen is a virus. In a specific embodiment, the virus is cytomegalovirus (CMV).

In specific embodiments of the methods of generating a population of cells comprising antigen-specific cells described herein, the ex vivo sensitizing step comprises ex vivo sensitizing the population of human blood cells to one or more antigens of Epstein-Barr virus (EBV).

In specific embodiments of the methods of generating a population of cells comprising antigen-specific cells described herein, the ex vivo sensitizing step comprises ex vivo sensitizing the population of human blood cells to one or more antigens of BK virus (BKV), John Cunningham virus (JCV), herpesvirus, adenovirus (ADV), human immunodeficiency virus (HIV), influenza virus, ebola virus, poxvirus, rhabdovirus, or paramyxovirus.

In specific embodiments of the methods of generating a population of cells comprising antigen-specific cells described herein, the ex vivo sensitizing step comprises ex vivo sensitizing the population of human blood cells to one or more antigens of the cancer. The cancer can be a blood cancer. In a specific embodiment, the cancer is multiple myeloma or plasma cell leukemia. In an aspect of the specific embodiment, the one or more antigens of the cancer is Wilms tumor 1 (WT1). The cancer can also be a solid tumor cancer, such as, but is not limited to: a cancer of the breast, lung, ovary, stomach, pancreas, larynx, esophagus, testes, liver, parotid, biliary tract, colon, rectum, cervix, uterus, endometrium, kidney, bladder, prostate, thyroid, brain, or skin.

In another aspect, provided herein are methods of treating a human patient having a pathogen or cancer, comprising: (i) generating a population of cells comprising antigen-specific T cells according to a method described herein; and (ii) administering the population of cells comprising antigen-specific T cells to the human patient.

In another aspect, provided herein are methods of treating a human patient having a pathogen or cancer, comprising administering a population of cells comprising antigen-specific T cells to the human patient, wherein the population of cells comprising antigen-specific T cells is the product of a method comprising generating the population of cells comprising antigen-specific T cells according to a method described herein.

In some embodiments, the antigen-specific T cells contained in the population of cells comprising antigen-specific T cells are restricted by an HLA allele shared with the diseased cells in the human patient to be treated. In other embodiments, the antigen-specific T cells contained in the population of cells comprising antigen-specific T cells share at least 2 HLA alleles (for example, at least 2 out of 8 HLA alleles, such as two HLA-A alleles, two HLA-B alleles, two HLA-C alleles, and two HLA-DR alleles) with the diseased cells in the human patient to be treated.

In specific embodiments, the population of human blood cells is derived from a human donor that is allogeneic to the human patient. In a specific embodiment, the human patient has been the recipient of a transplant from a transplant donor, and the human donor is a third-party donor that is different from the transplant donor.

In some embodiments, the administering step comprises administering the population of cells comprising antigen-specific T cells to the human patient, at a dose that is less than or equal to about $1\times10^5$ cells of the population of cells comprising antigen-specific T cells per kg of the human patient. In a specific embodiment, the administering step comprises administering the population of cells comprising antigen-specific T cells to the human patient, at a dose that is less than or equal to about 5×10⁴ cells of the population of cells comprising antigen-specific T cells per kg of the human patient. In a preferred embodiment, the administering step comprises administering the population of cells comprising antigen-specific T cells to the human patient, at a dose that is less than or equal to about 1×10⁴ cells of the population of cells comprising antigen-specific T cells per kg of the human patient. In another specific embodiment, the administering step comprises administering the population of cells comprising antigen-specific T cells to the human patient, at a dose that is less than or equal to about 5×10³ cells of the population of cells comprising antigen-specific T cells per kg of the human patient. In another specific embodiment, the administering step comprises administering the population of cells comprising antigen-specific T cells to the human patient, at a dose that is less than or equal to about 1×10³ cells of the population of cells comprising antigen-specific T cells per kg of the human patient.

In certain embodiments, the step of administering comprises administering the population of cells comprising antigen-specific T cells to the human patient at the dose described above weekly.

In certain embodiments, the step of administering is by bolus intravenous infusion.

In certain embodiments, the step of administering comprises administering at least 2 doses of the population of cells comprising antigen-specific T cells to the human patient. In specific embodiments, the step of administering comprises administering 2, 3, 4, 5, or 6 doses of the population of cells comprising antigen-specific T cells to the human patient.

In a specific embodiment, the step of administering comprises administering a first cycle of one dose per week of the population of cells comprising antigen-specific T cells for 3 consecutive weeks followed by a washout period during which no dose of the population of cells comprising antigen-specific T cells is administered, followed by a second cycle of said one dose per week of the population of cells comprising antigen-specific T cells for 3 consecutive weeks.

In specific embodiments, the step of administering comprises administering two, three, four, five, or six cycles of one dose per week of the population of cells comprising antigen-specific T cells for three consecutive weeks, each cycle separated by a washout period during which no dose of the population of cells comprising antigen-specific T cells is administered.

In specific embodiments, the washout period is about 1, 2, 3, or 4 weeks. In a preferred embodiment, the washout period is about 3 weeks.

In specific embodiments, the step of administering of the population of cells comprising antigen-specific T cells does not result in any graft-versus-host disease (GvHD) in the human patient.

In another aspect, provided herein are populations of cells comprising antigen-specific T cells for therapeutic administration to a human patient having or suspected of having a pathogen or cancer, wherein the population of cells comprising antigen-specific T cells is the product of a method comprising generating the population of cells comprising antigen-specific T cells according to a method described herein. In specific embodiments, provided herein is a population of cells comprising antigen-specific T cells for therapeutic administration to a human patient having or suspected of having a pathogen or cancer, wherein the population of cells comprising antigen-specific T cells is the product of a method comprising generating the population of cells comprising antigen-specific T cells according to a method described herein, and wherein the population of cells comprising antigen-specific T cells is cryopreserved.

In another aspect, provided herein is a cell bank comprising a plurality of populations of cells comprising antigen-specific T cells described herein.

4. BRIEF DESCRIPTION OF FIGURES

FIG. 1. Isolation and characterization of $T_N$, $T_{SCM}$, $T_{CM}$ and $T_{EM}$ populations from human peripheral blood. Flow cytometry was used to isolate the $T_N$, $T_{SCM}$, $T_{CM}$ and $T_{EM}$ subsets from peripheral blood mononuclear cell (PBMCs). Lymphocytes were first gated within PBMCs by forward scatter (FSC) and side scatter (SCC) and analyzed for CD45RO, CD95, CD62L and CD3 expression. CD3⁺ lymphocytes were then gated for CD45RO⁺CD62L⁺ $T_{CM}$ and CD45RO⁺CD62L⁻ $T_{EM}$, CD45RO⁻CD62L⁺CD95⁺ $T_{SCM}$ cells and CD45RO⁻CD62L⁺CD95⁻ $T_N$ cells.

Figures 1, 5A:
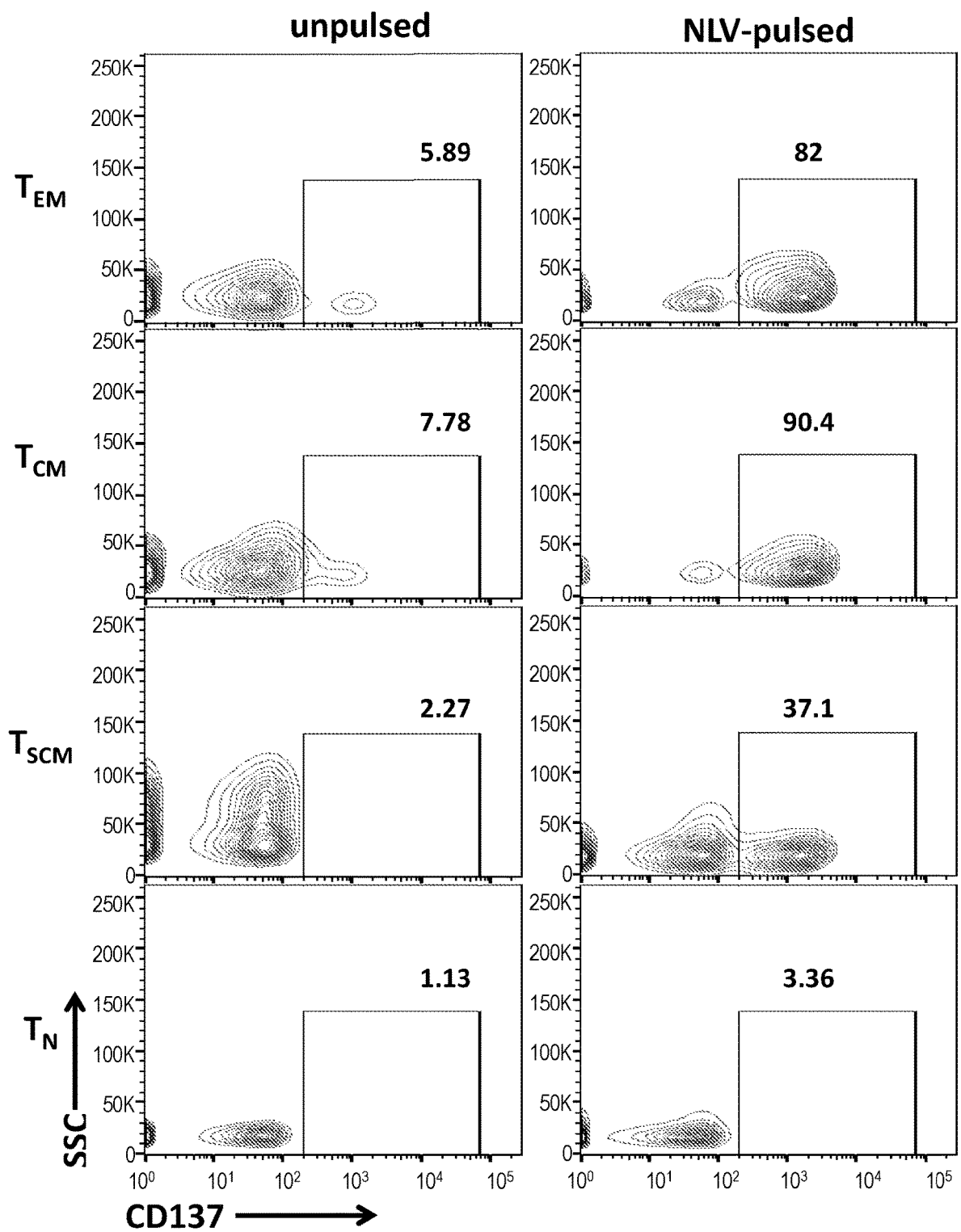
Figures 2, 5A:
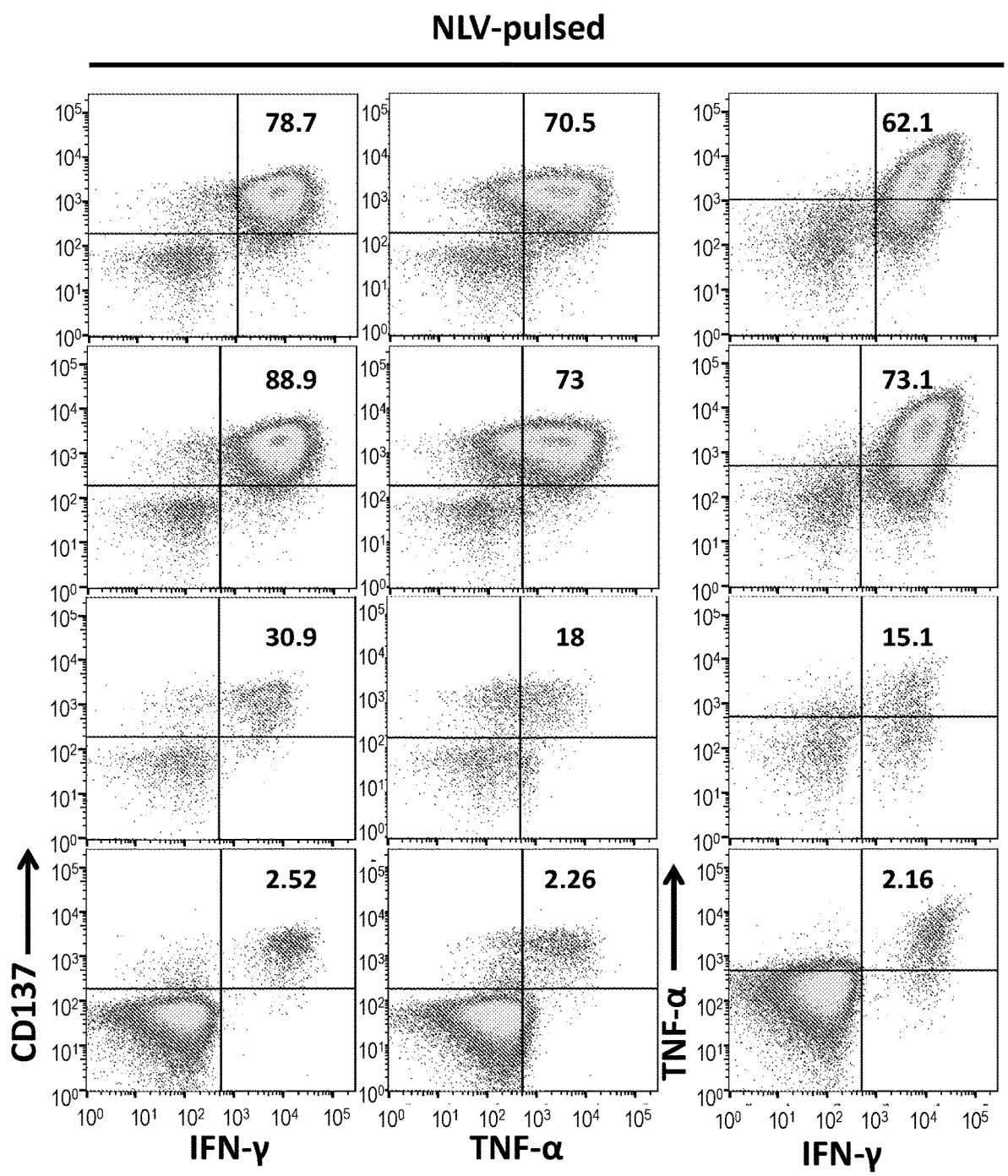

FIG. 2. Phenotypic characterization of naive and memory ($T_N$, $T_{SCM}$, $T_{CM}$ and $T_{EM}$)-derived CMV-specific CD8⁺ T cells upon antigen stimulation. (A), (B) and (C) Isolated T cells from $T_N$, $T_{SCM}$, $T_{CM}$ and $T_{EM}$ cell populations were sensitized with artificial antigen presenting cells (AAPCs) expressing CMVpp65 peptide and HLA-A:0201. CD3+ T lymphocytes derived from each cell population were evaluated at 7 (A), 14 (B) and 30 days (C) post-stimulation. CD8⁺ single, live T cells were gated from CD3+ T lymphocytes. HLA-A:0201-NLV Tetramer (Tet)⁺ and NLV-Tet⁻ T cells were then gated within CD8⁺ T cells (left panel). Expression frequencies of CD62L, CCR7 and CD45RA gated on NLV-Tet⁺ and NLV-Tet⁻ population are shown for a representative donor. (Regular font text: NLV-Tet⁺; Bold font text: NLV-Tet⁻.) (FIGS. 2A-2C were originally in color, so for purposes of this black and white reproduction of the figures, outlines of the former blue FACS plot contours were traced manually in order to make them distinguishable on black and white reproduction from the former red contours, the outlines of which were not traced.) Percentages of CCR7⁺ cells 14 days post-stimulation are shown in (D) for NLV-Tet⁺ and in (E) for NLV-Tet⁻ T cells (n=6; *P<0.05; **P<0.01; from Mann-Whitney test).

FIG. 3. Distinct expression of co-stimulatory and senescence markers within $T_N$, $T_{SCM}$, $T_{CM}$ and $T_{EM}$. Expression frequencies of CD27, CD57, CD127, CD28, KLRG1 and PD1 gated on NLV-Tet⁺ and NLV-Tet⁻ populations after in-vitro stimulation for 14-18 days are shown. (A) Percentage of CD27⁺ cells within NLV-Tet⁺ CD8⁺ T cells (n=6) derived from $T_N$, $T_{SCM}$, $T_{CM}$ and $T_{EM}$ populations, respectively. (B) Representative fluorescence-activated cell sorting (FACS) plots of the CD27 expression within CD8⁺ T cells. (C) Percentage of NLV-Tet⁺ CD8⁺ T cells expressing CD57 (n=8) derived from $T_N$, $T_{SCM}$, $T_{CM}$ and $T_{EM}$ populations, respectively. (D) Representative FACS plots of the CD57 expression in CD8⁺ T cells. (E) and (F) Percentage of NLV-Tet⁺ CD8⁺ T cells expressing CD 127 (n=6) and CD28 (n=8) respectively, derived from $T_N$, $T_{SCM}$, $T_{CM}$ and $T_{EM}$ populations, respectively. (G) and (H) Percentage of CD8⁺ T cells expressing KLRG1 within NLV-Tet⁺ (G) and NLV-Tet⁻ T cells post-stimulation (n=9). (I) and (J) Percentage of CD8⁺ T cells expressing PD1 within NLV-Tet⁺ (I) and NLV-Tet⁻ (J) T cells post-stimulation (n=11). (*P<0.05; P<0.01; *P<0.005; from Mann-Whitney test.)

FIG. 4. Enrichment of CMV-specific CD8⁺ T cells results from rapid expansion of early memory T cells. (A) In-vitro proliferation of A2-NLV-Tet⁺ T cells was evaluated after in-vitro sensitization with CMVpp65 antigen by EdU as shown in a representative donor on Day 3, 5 and 7 post-stimulation. CD3$^+$ T cells were sensitized with artificial antigen presenting cells (AAPCs) expressing CMVpp65 peptide and HLA-A*0201. The enrichment of NLV-Tet$^+$ T cells after stimulation was evaluated as shown on the left panel. Percentage of EdU incorporation gated on single, live CD8$^+$ T lymphocytes is shown in the middle panel. Percentage of EdU incorporation gated on NLV-Tet$^+$ CD8$^+$ T cells is shown on the right panel. (B) Phenotypic analysis of NLV-Tet$^+$ T cells (right panel) in comparison to NLV-Tet$^+$ T cells with EdU incorporation (left panel) is shown for a representative donor. (White: CD45RO$^+$CD62L$^-$ T$_{EM}$; Light Grey: CD45RO$^+$CD62L$^+$ T$_{CM}$; Dark Grey: CD45RO$^-$CD62L$^+$CD95$^+$ T$_{SCM}$.) CD45RO$^-$CD62L$^+$CD95$^-$ T$_N$ cells were not detected post antigen stimulation. (C) Fold expansion of A2-NLV-Tet$^+$ T cells after 14 days of antigen-specific T cell stimulation was evaluated within NLV-Tet$^+$ CD8$^+$ T cells within the T$_N$-, T$_{SCM}$-, T$_{CM}$- and T$_{EM}$-derived cells. NLV-Tet$^+$ CD8$^+$ T cells were not detected before exposure to antigen in 4 out of 6 donors for the T$_N$ population (n=6) (*P=0.03; ns, not significant; from Mann-Whitney test).

FIG. 5. Functional cytokine profile and cytotoxic activity of in vitro expanded CMV-specific T cells derived from naive (T$_N$) and memory T cells (T$_{SCM}$, T$_{CM}$ and T$_{EM}$). (A) Expanded naive and memory T cell populations were stimulated for 18 hours with NLV peptide loaded autologous B-lymphoblastoid cell line cells (BLCL cells) at a ratio of 5:1. T cells co-cultured with autologous BLCLs without peptide loading served as controls. CD8$^+$ T cells secreting IFN-γ and TNF-α were evaluated by intracellular staining. The percentage of CD8$^+$ T cells expressing CD137 are shown on the first 2 panels (on FIG. 5A-1) with or without peptide stimulation. The proportion of CD8+ T cells expressing CD137 and secreting IFN-γ or TNF-α cytokine is shown in the next 2 panels (on FIG. 5A-2). CD8$^+$ T cells secreting both IFN-γ and TNF-α cytokine are shown in the last panel (on FIG. 5A-2). (B) Cytotoxic activity was evaluated by CD107a degranulation assay. The percentage of CD8$^+$ T cells expressing CD107a with (middle panel) or without (left panel) peptide stimulation is shown. The percentage of CD8$^+$ T cells expressing both CD137 and CD107a is shown in the right panel. Data shown is a representative of three experiments (n=3).

FIG. 6. Clonal diversity and clonotype selection within CMV-specific T$_N$, T$_{SCM}$, T$_{CM}$ and T$_{EM}$ cells. Next-generation sequencing was performed for TCRVβ repertoire analysis. TCR clonality was analyzed using immuno SEQ Analyzer 2.0 (A) before and (B) 15 days after T cell expansion, for NLV-Tet$^+$ T cells contained within (A) sorted T$_N$, T$_{SCM}$, T$_{CM}$ and T$_{EM}$ subsets or (B) cells derived from these subsets, respectively. Heat map indicates similarity of sample profiles. The similarity accounts for overlap between unique nucleotide sequences within any two samples. (c) Sorted NLV-Tet$^+$ T cells derived from Naive (T$_N$), and memory (T$_{SCM}$, T$_{CM}$ and T$_{EM}$) subsets from the same donor after 30 days expansion were compared for their TCR sequences. TCR sequencing was performed on sorted NLV-Tet$^+$ T cells derived from Naive (T$_N$), and memory (T$_{SCM}$, T$_{CM}$ and T$_{EM}$) subsets from a separate donor (D) before, (E) after 15 days and, (F) after 30 days of in vitro stimulation, and compared for their similarities. Values shown are proportions of overlap. The TCR sequencing analysis for this donor at the same time points (pre-, day 15 and day 30 post-stimulation) is summarized in (G).

FIG. 7. Enhanced proliferation of T$_{SCM}$ cells may not explain immunodominance. (A) T cells from HLA-A:0201$^+$ and A:2402$^+$ CMV seropositive donors were sensitized with artificial antigen presenting cells (AAPCs) expressing HLA-A:0201 or HLA-A:2402 and CMVpp65 protein. T cells gated on single, live CD8$^+$ T lymphocytes were gated for cells binding the HLA-A:0201-NLVPMVATV (SEQ ID NO:1) peptide tetrameric complexes (NLV-Tet$^+$) or HLA-A:2402-QYDPVAALF (SEQ ID NO:2) peptide tetrameric complexes (QYD-Tet$^+$) after 4, 5, 7 and 8 days post antigen specific stimulation (n=2). Results are shown for one representative donor. Phenotypic analysis of NLV-Tet$^+$ or QYD-Tet$^+$ T cells was performed to evaluate the proportion of T$_{SCM}$, T$_{CM}$ and T$_{EM}$-derived cells after antigen specific stimulation (CD45RO$^+$CD62L$^+$ T$_{CM}$: Light Gray; CD45RO$^+$CD62L$^-$ T$_{EM}$: White; CD45RO$^-$CD62L$^+$CD95$^+$ T$_{SCM}$: Dark Gray). There were no Tet$^+$ T cells with T$_N$ phenotype CD45RO$^-$CD62L$^+$CD95$^-$ post-sensitization. (B) T cells labeled with EdU were used to evaluate and compare the proportion of proliferating T cells within NLV-Tet$^+$ and the proportion of proliferating T cells within QYD-Tet$^+$ T cells, within T$_{SCM}$-, T$_{CM}$- and T$_{EM}$-derived cells 4, 5, 7 and 8 days post stimulation (FIG. 7B-1). The proportion of apoptotic T cells within EdU labeled NLV-Tet$^+$ or EdU labeled QYD-Tet$^+$ population was evaluated after T cell stimulation at 4, 5, 7 and 8 days using Annexin V labeling (FIG. 7B-2).

5. DETAILED DESCRIPTION

The present invention provides methods of generating antigen-specific T cells for therapeutic administration to a human patient having or suspected of having a pathogen or cancer, antigen-specific T cells generated by such methods, and methods of treating a human patient using such antigen-specific T cells. According to the present invention, stem cell-like memory T cells (T$_{SCM}$ cells) are a more suitable source of T cells for the generation of antigen-specific T cells for adoptive immunotherapy, relative to naive T cells (T$_N$ cells), central memory T cells (T$_{CM}$ cells) and effector memory T cells (T$_{EM}$ cells), because they allow rapid, persistent and selective in vitro expansion of antigen-specific T cells that recognize dominant epitopes of antigens of pathogens found in human blood and are the principal and persistent reservoir for rapid repopulation of immunodominant T cells in vivo.

5.1. Methods of Generating Antigen-Specific T Cells for Adoptive Immunotherapy

5.1.1. Methods Using Ex Vivo Sensitization of T$_{SCM}$ Cells

In one aspect, provided herein are methods of generating a population of cells comprising antigen-specific T cells for therapeutic administration to a human patient having or suspected of having a pathogen or cancer, comprising: (a) ex vivo sensitizing a population of human blood cells to one or more antigens of the pathogen or cancer over a period of time in culture, wherein at the initiation of said period of time, the population of human blood cells contains at least 50% stem cell-like memory T cells (T$_{SCM}$ cells); and (b) cryopreserving (i) the ex vivo sensitized population of human blood cells, or (ii) cells derived therefrom that comprise antigen-specific T cells recognizing the one or more antigens of the pathogen or cancer; thereby producing said population of cells comprising antigen-specific T cells.

Ex Vivo Sensitization

In specific embodiments, the aforementioned period of time in culture (termed herein "the Sensitization Culture Time;" i.e., the culture time period over which sensitization occurs) is in the range of 9-21 days. As will be clear, this means that the period of time in culture for sensitization purposes starting with the first culturing in the presence of antigen until the end of culturing in the presence of antigen is only for 9-21 days and not longer. (The cells may optionally be cultured for a longer period of time, but not in the presence of antigen for sensitization.) In a specific embodiment, the Sensitization Culture Time is in the range of 9-14 days. In another specific embodiment, the Sensitization Culture Time is 9 days. In another specific embodiment, the Sensitization Culture Time is 10 days. In another specific embodiment, the Sensitization Culture Time is 11 days. In another specific embodiment, the Sensitization Culture Time is 12 days. In another specific embodiment, the Sensitization Culture Time is 13 days. In another specific embodiment, the Sensitization Culture Time is 14 days. In another specific embodiment, the Sensitization Culture Time is 15 days. In another specific embodiment, the Sensitization Culture Time is 16 days. In another specific embodiment, the Sensitization Culture Time is 17 days. In another specific embodiment, the Sensitization Culture Time is 18 days. In another specific embodiment, the Sensitization Culture Time is 19 days. In another specific embodiment, the Sensitization Culture Time is 20 days. In another specific embodiment, the Sensitization Culture Time is 21 days.

The ex vivo sensitizing step can be performed by any method known in the art to stimulate T cells to be antigen-specific ex vivo, such as a method as described in Koehne et al., 2000, Blood 96:109-117; Trivedi et al., 2005, Blood 105:2793-2801; Haque et al., 2007, Blood 110:1123-1131; Hasan et al., 2009, J Immunol 183: 2837-2850; Feuchtinger et al., 2010, Blood 116:4360-4367; Doubrovina et al., 2012, Blood 120:1633-1646; Leen et al., 2013, Blood 121:5113-5123; Papadopoulou et al., 2014, Sci Transl Med 6:242ra83; Sukdolak et al., 2013, Biol Blood Marrow Transplant 19:1480-1492; Koehne et al., 2015, Biol Blood Marrow Transplant 21: 1663-1678, or International Patent Application Publication No. WO 2016/073550.

In specific embodiments, the ex vivo sensitizing step comprises co-culturing the population of human blood cells with one or more immunogenic peptides or proteins derived from the one or more antigens (preferably also in the presence of antigen presenting cells). In specific embodiments, the ex vivo sensitizing step comprises co-culturing the population of human blood cells with antigen presenting cells that present the one or more antigens. The ex vivo sensitizing step preferably comprises first supplementing the culture with IL-15 and IL-7 (e.g., starting from day 4 after the initiation of the Sensitization Culture Time, or earlier), and then supplementing the culture with IL-2 (e.g., at least 7 days after the initiation of the Sensitization Culture Time) optionally together with IL-15 and IL-7. IL-15 and IL-7 help to maintain stem cell-like phenotype of the $T_{SCM}$ cells, and are preferably added to the culture within the first seven days of culturing in the ex vivo sensitizing step and then again for multiple times. IL-2 helps to boost expansion of the antigen-specific T cells, and is preferably added to the cell culture on a culture date that is later than the initial addition of IL-15 and IL-7 to the cell culture in the ex vivo sensitizing step (e.g., IL-2 is added at least 7 days after the initiation of the Sensitization Culture Time). In a specific embodiment, the ex vivo sensitizing step comprises supplementing the culture with IL-15 and IL-7 on day 4 and day 7 after the initiation of the Sensitization Culture Time, and then supplementing the culture with IL-15, IL-7 and IL-2 every other day starting after day 12 after the initiation of the Sensitization Culture Time.

The antigen presenting cells used in the ex vivo sensitizing step can be any antigen presenting cells suitable for presenting the one or more antigens, such as dendritic cells, cytokine-activated monocytes, peripheral blood mononuclear cells (PBMCs), Epstein-Barr virus-transformed B-lymphoblastoid cell line cells (EBV-BLCL cells), or artificial antigen presenting cells (AAPCs). In a specific embodiment, the antigen presenting cells are dendritic cells. In another specific embodiment, the antigen presenting cells are PBMCs. In another specific embodiment, the antigen presenting cells are EBV-BLCL cells. In another specific embodiment, the antigen presenting cells are AAPCs. In certain embodiments, the antigen presenting cells are derived from the donor of the population of human blood cells. The antigen presenting cells can be obtained by any method known in the art, such as the method(s) described in Koehne et al., 2000, Blood 96:109-117; Koehne et al., 2002, Blood 99:1730-1740; Trivedi et al., 2005, Blood 105:2793-2801; O'Reilly et al., 2007, Immunol Res 38:237-250; Hasan et al., 2009, J Immunol 183: 2837-2850; Barker et al., 2010, Blood 116:5045-5049; O' Reilly et al., 2011, Best Practice & Research Clinical Haematology 24:381-391; Doubrovina et al., 2012, Blood 120:1633-1646; Koehne et al., 2015, Biol Blood Marrow Transplant 21: 1663-1678, or International Patent Application Publication No. WO 2016/073550.

In some embodiments, the antigen presenting cells are loaded with one or more immunogenic peptides or proteins derived from the one or more antigens. Non-limiting exemplary methods for loading antigen presenting cells with peptide(s) derived from antigen(s) can be found in Trivedi et al., 2005, Blood 105:2793-2801; Hasan et al., 2009, J Immunol 183: 2837-2850; and International Patent Application Publication No. WO 2016/073550. In other embodiments, the antigen presenting cells are genetically engineered to recombinantly express one or more immunogenic peptides or proteins derived from the one or more antigens. Any appropriate method known in the art for introducing nucleic acid vehicles into cells to express proteins, such as transduction or transformation, can be used to genetically engineer the antigen presenting calls to recombinantly express the one or more immunogenic peptides or proteins derived from the one or more antigens.

In some embodiments, the one or more immunogenic peptides or proteins are a pool of overlapping peptides derived from the one or more antigens. In specific embodiments, the pool of overlapping peptides is a pool of overlapping pentadecapeptides. In other embodiments, the one or more immunogenic peptides or proteins are one or more proteins derived from the one or more antigens.

Cryopreservation

In preferred embodiments, the step of cryopreserving comprises steps of: (c) recovering from culture the ex vivo sensitized population of human blood cells or cells derived therefrom; (d) combining with a cryopreservative the ex vivo sensitized population of human blood cells or cells derived therefrom; and (e) freezing the ex vivo sensitized population of human blood cells, or cells derived therefrom, combined with the cryopreservative. Cells derived from the ex vivo sensitized population of human blood cells and comprising antigen-specific T cells which recognize the one or more antigens of the pathogen or cancer can be a fraction of the ex vivo sensitized population of human blood cells (e.g., a $CD3^+$ T cell population enriched from the ex vivo sensitized population of human blood cells, or a $CD8^+$ cytotoxic T cell population enriched from the ex vivo sensitized population of human blood cells) or an expanded population of the ex vivo sensitized population of human blood cells.

Freezing of cells is ordinarily destructive. On cooling, water within the cell freezes. Injury then occurs by osmotic effects on the cell membrane, cell dehydration, solute concentration, and ice crystal formation. As ice forms outside the cell, available water is removed from solution and withdrawn from the cell, causing osmotic dehydration and raised solute concentration which eventually destroy the cell. (For a discussion, see Mazur, 1977, Cryobiology 14:251-272.) These injurious effects can be circumvented by (a) use of a cryopreservative, (b) control of the freezing rate, and (c) storage at a temperature sufficiently low to minimize degradative reactions.

Cryopreservative which can be used in accordance with the present invention can be, but is not limited to, dimethyl sulfoxide (DMSO), glycerol, polyvinylpyrrolidine, polyethylene glycol, albumin, dextran, sucrose, ethylene glycol, i-erythritol, D-ribitol, D-mannitol, D-sorbitol, i-inositol, D-lactose, choline chloride, amino acids, methanol, acetamide, glycerol monoacetate, or inorganic salts. In a preferred embodiment, the cryopreservative which is used in accordance with the present invention is DMSO. Being a small molecule, DMSO freely permeates the cell and protects intracellular organelles by combining with water to modify its freezability and prevent damage from ice formation. Addition of plasma, fetal calf serum, or human albumin can augment the protective effect of DMSO. After addition of DMSO, cells should be kept at 0° C. until freezing, since DMSO concentrations of about 1% are toxic at temperatures above 4° C.

A controlled slow cooling rate is also critical. Different cryopreservatives (Rapatz, G., et al., 1968, Cryobiology 5(1):18-25) and different cell types have different optimal cooling rates (see, e.g., Rowe and Rinfret, 1962, Blood 20:636; Rowe, 1966, Cryobiology 3:12-18; Lewis et al., 1967, Transfusion 7:17-32; and Mazur, 1970, Science 168: 939-949). The heat of fusion phase where water turns to ice should be minimal. The cooling procedure can be carried out by use of, e.g., a programmable freezing device or a methanol bath procedure. Any method for cryopreserving that preserves viability of the cells can be used. In specific embodiments, a controlled rate freezer is used in the cryopreserving step to bring the temperature of the vial of cells to ≤−90° C. or less, at a rate ranging from −0.3 to −2° C. per minute. By way of example but not limitation, the following program can be used: 1) wait for chamber is 4° C. and sample is 6.0° C.; 2) ramp at 1.0° C./min. until sample is −6.0° C.; 3) ramp at 25° C./min. until chamber is −45° C.; 4) ramp at 10° C./min. until chamber is −14° C.; 5) ramp at 1.0° C./min. until chamber is −40° C.; 6) ramp at 10° C./min. until chamber is −90° C.; and 7) transfer to liquid nitrogen. Alternatively, the cells can be placed in a Mr. Frosty™ or other alcohol/polystyrene insulated freezing chamber preconditioned at −20° C. and frozen overnight by transferring the chamber to a −80° C. freezer, prior to transfer to liquid nitrogen storage.

After thorough freezing, the ex vivo sensitized population of human blood cells or cells derived therefrom can be rapidly transferred to a long-term cryogenic storage vessel. In a preferred embodiment, the ex vivo sensitized population of human blood cells or cells derived therefrom can be cryogenically stored in liquid nitrogen (−196° C.) or its vapor (−165° C.). In a specific embodiment, the cells are stored at −80° C. for 2 days and then transferred to liquid nitrogen. In a specific embodiment, a plurality of the populations of cells comprising antigen-specific T cells are generated and stored as described herein, thereby producing a cell bank.

In a preferred embodiment, by way of example but not limitation, the cryopreserving step is performed as follows: First, a freeze mix is prepared containing 90% fetal calf serum and 10% DMSO (in sterile, 15 ml tubes, 9 ml of heat inactivated and filtered fetal calf serum is mixed with sterile, filtered 1 ml of DMSO). Aliquots of this freeze mix are prepared under sterile conditions and then stored at −20° C. for use as a suspension medium for freezing cells. T cells suspended at $1 \times 10^6$/ml in Tcell medium are centrifuged in 15 or 50 ml tubes at 1500 rpm for 5 mins. The supernatant is gently discarded, cells are washed a second time with phosphate buffered saline (PBS), and cell pellet is then suspended in the thawed freeze mix at $10 \times 10^6$ cells/ml.

Other known methods of cryopreservation of viable cells, or modifications thereof, are available and envisioned for use (e.g., cold metal-mirror techniques; Livesey and Linner, 1987, Nature 327:255; Linner et al., 1986, J Histochem Cytochem 34:1123-1135; see also U.S. Pat. No. 4,199,022 by Senkan et al., U.S. Pat. No. 3,753,357 by Schwartz, U.S. Pat. No. 4,559,298 by Fahy).

In certain embodiments, the method of generating a population of cells comprising antigen-specific T cells further comprises, after the step of cryopreserving, steps of thawing and optionally expanding in culture the ex vivo sensitized population of human blood cells or cells derived therefrom. Frozen cells are preferably thawed quickly (e.g., in a water bath maintained at 37-41° C.) and chilled immediately upon thawing. In particular, the vial containing the frozen cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed in ice.

The cryopreservative, if toxic in humans, can be removed prior to therapeutic administration, and the removal is preferably accomplished upon thawing. However, when the cryopreservative is DMSO, it is preferable to omit this step in order to avoid cell loss, since DMSO in a low concentration has no serious toxicity.

TCR- or CAR-Expression

In some embodiments, the population of cells comprising antigen-specific T cells comprises antigen-specific T cells that recombinantly express a protein of interest, for example, a T cell receptor (TCR) or a chimeric antigen receptor (CAR). This can be achieved by transducing the population of human blood cells during their time in culture with a nucleic acid encoding the protein of interest. The nucleic acid preferably is a vector in which a nucleic acid sequence encoding the protein of interest is operably linked to a promoter. The transducing preferably occurs during days 3-5 in culture, since, as shown by the example section herein (i.e., Section 6), this time is when the $T_{SCM}$ cells exhibit the highest proliferative capacity.

In some embodiments, the population of cells comprising antigen-specific T cells, as described herein, comprises antigen-specific T cells that endogenously express a public T cell receptor (TCR) recognizing the one or more antigens. In other embodiments, the population of cells comprising antigen-specific T cells, as described herein, comprises antigen-specific T cells that recombinantly express a public TCR recognizing the one or more antigens. In specific embodiments, the method of generating a population of cells comprising antigen-specific T cells, as described herein, further comprises transducing the population of human blood cells with a nucleic acid encoding a public TCR (e.g., at a time when the population of human blood cells has been cultured for 3-5 days), for example, using a transducing method as described in Section 5.1.2, infra. The transducing step can be performed before, during, or after the ex vivo sensitizing step, which reduces alloreactivity of the population of cells comprising antigen-specific T cells.

Public TCRs are peptide-specific TCRs with highly homologous sequences detected in multiple individuals (Li et al., 2012, Cell Res 22:33-42). Public TCRs for a variety of human viruses have been described (Argaet et al., 1994, J Exp Med 180:2335-2340; Wang et al., 2012, Sci Transl Med 4:128ra142; Nguyen et al., 2014, J Immunol 192:5039-5049; Trautmann et al., 2005, J Immunol 175:6123-6132).

In a specific embodiment wherein the one or more antigens is cytomegalovirus (CMV) pp65, the public TCR comprises a β-chain comprising a variable domain, which comprises a complementarity determining region (CDR)3 of CASSPQTGASYGYTF (SEQ ID NO:3). In another specific embodiment wherein the one or more antigens is CMV pp65, the public TCR comprises a β-chain comprising a variable domain, which comprises a CDR3 of CASSPKTGAVYGYTF (SEQ ID NO:4). In another specific embodiment wherein the one or more antigens is CMV pp65, the public TCR comprises a β-chain comprising a variable domain, which comprises a CDR3 of S*$_n$TG*$_n$GY (SEQ ID NO:16; *n indicates any amino acid sequence of any length and any amino acid combination).

In certain embodiments, the population of cells comprising antigen-specific T cells, as described herein, comprises antigen-specific T cells that recombinantly express a chimeric antigen receptor (CAR) recognizing the one or more antigens (see Section 5.1.3, infra, for more details regarding CAR). In specific embodiments, the method of generating a population of cells comprising antigen-specific T cells, as described herein, further comprises transducing the population of human blood cells with a nucleic acid encoding a CAR (e.g., at a time when the population of human blood cells has been cultured for 3-5 days), for example, using a transducing method as described in Section 5.1.3, infra. The transducing step can be performed before, during, or after the ex vivo sensitizing step, which reduces alloreactivity of the population of cells comprising antigen-specific T cells.

5.1.2. Methods Using TCR-Transduced $T_{SCM}$ Cells

In another aspect, provided herein are methods of generating a population of cells comprising antigen-specific T cells for therapeutic administration to a human patient having or suspected of having a pathogen or cancer, comprising transducing a population of human blood cells with a nucleic acid encoding a public TCR recognizing one or more antigens of the pathogen or cancer (preferably at a time when the population of human blood cells has been cultured for 3-5 days), wherein the population of human blood cells contains at least 50% $T_{SCM}$ cells; thereby producing said population of cells comprising antigen-specific T cells. The transducing preferably occurs during days 3-5 in culture, since, as shown by the example section herein (i.e., Section 6), this time is when the $T_{SCM}$ cells exhibit the highest proliferative capacity.

In a specific embodiment wherein the one or more antigens is CMV pp65, the public TCR comprises a β-chain comprising a variable domain, which comprises a CDR3 of CASSPQTGASYGYTF (SEQ ID NO:3). In another specific embodiment wherein the one or more antigens is CMV pp65, the public TCR comprises a β-chain comprising a variable domain, which comprises a CDR3 of CASSPKTGAVYGYTF (SEQ ID NO:4). In another specific embodiment wherein the one or more antigens is CMV pp65, the public TCR comprises a β-chain comprising a variable domain, which comprises a CDR3 of S*$_n$TG*$_n$GY (SEQ ID NO:16; *n indicates any amino acid sequence of any length and any amino acid combination).

In another aspect, provided herein are methods of generating a population of cells comprising antigen-specific T cells for therapeutic administration to a human patient having or suspected of having a CMV infection, comprising transducing a population of human blood cells with a nucleic acid encoding a public TCR recognizing CMV pp65 (preferably at a time when the population of human blood cells has been cultured for 3-5 days), wherein the public TCR comprises a β-chain comprising a variable domain, which comprises a CDR3 of CASSPQTGASYGYTF (SEQ ID NO:3), and wherein the population of human blood cells contains at least 50% $T_{SCM}$ cells; thereby producing said population of cells comprising antigen-specific T cells.

In another aspect, provided herein are methods of generating a population of cells comprising antigen-specific T cells for therapeutic administration to a human patient having or suspected of having a CMV infection, comprising transducing a population of human blood cells with a nucleic acid encoding a public TCR recognizing CMV pp65 (preferably at a time when the population of human blood cells has been cultured for 3-5 days), wherein the public TCR comprises a β-chain comprising a variable domain, which comprises a CDR3 of CASSPKTGAVYGYTF (SEQ ID NO:4), and wherein the population of human blood cells contains at least 50% $T_{SCM}$ cells; thereby producing said population of cells comprising antigen-specific T cells.

In another aspect, provided herein are methods of generating a population of cells comprising antigen-specific T cells for therapeutic administration to a human patient having or suspected of having a CMV infection, comprising transducing a population of human blood cells with a nucleic acid encoding a public TCR recognizing CMV pp65 (preferably at a time when the population of human blood cells has been cultured for 3-5 days), wherein the public TCR comprises a β-chain comprising a variable domain, which comprises a CDR3 of S*$_n$TG*$_n$GY (SEQ ID NO:16; *n indicates any amino acid sequence of any length and any amino acid combination), and wherein the population of human blood cells contains at least 50% $T_{SCM}$ cells; thereby producing said population of cells comprising antigen-specific T cells.

In specific embodiments, the method of generating a population of cells comprising antigen-specific T cells further comprises, after the step of transducing, a step of cryopreserving the transduced population of human blood cells or cells derived therefrom. In a specific embodiment, the method of generating a population of cells comprising antigen-specific T cells further comprises, after the step of cryopreserving, steps of thawing and optionally expanding in culture the transduced population of human blood cells or cells derived therefrom. The cryopreserving and thawing steps can be performed as described in Section 5.1.1, supra.

In specific embodiments, the method of generating a population of cells comprising antigen-specific T cells further comprises, after the step of transducing, a step of expanding in culture the transduced population of human blood cells or cells derived therefrom, wherein the transduced population of human blood cells or cells derived therefrom has not been cryopreserved.

TCR is a cell surface molecule on T cells that is responsible for recognizing antigen peptide-bound major histocompatibility complex (MHC) molecules. Public TCRs are peptide-specific TCRs with highly homologous sequences detected in multiple individuals (Li et al., 2012, Cell Res 22:33-42). Public TCRs for a variety of human viruses have been described (Argaet et al., 1994, J Exp Med 180:2335-2340; Wang et al., 2012, Sci Transl Med 4:128ra142; Nguyen et al., 2014, J Immunol 192:5039-5049; Trautmann et al., 2005, J Immunol 175:6123-6132).

The population of human blood cells transduced with a nucleic acid encoding a TCR can be generated by any method known in the art, for example, as described in Stauss et al., 2015, Curr Opin Pharmacol 24:113-118; Sharpe and Mount, 2015, Dis Model Mech 8:337-350; Kunert et al., 2013, Front Immunol 4: 363; Stone et al., 2012, Methods Enzymol 503:189-222; or Park et al., 2011, Trends Biotechnol 29:550-557.

The nucleic acid encoding a TCR can be DNA, RNA, or a nucleic acid analog. In specific embodiments, such a nucleic acid may be part of a vector. In a specific embodiment, the vector is an expression vector that is capable of directing the expression of a nucleic acid encoding a polypeptide of the TCR described herein in T cells. Non-limiting examples of expression vectors suitable for directing the expression of a nucleic acid encoding a polypeptide of the TCR described herein include, but are not limited to, plasmids and viral vectors, such as synthetic vectors, lentiviral vectors, replication-defective retroviral vectors, autonomously replicating plasmids. In a specific embodiment, an expression vector used for directing the expression of a nucleic acid encoding a polypeptide of the TCR described herein includes one or more regulatory sequences operably linked to the nucleic acid to be expressed. "Operably linked" is intended to mean that a nucleic acid of interest is linked to the regulatory sequence(s) in a manner which allows for expression of the nucleic acid in T cells. Regulatory sequences include promoters, enhancers and other expression control elements (e.g., polyadenylation signals).

A nucleic acid encoding a polypeptide of the TCR described herein, for example, an expression vector, can be transduced into host cells via conventional transformation or transfection (such as, transfection by a virus, e.g., a retrovirus or lentivirus) techniques. Such techniques include, but are not limited to, calcium phosphate or calcium chloride co-precipitation, DEAE-dextran-mediated transfection, lipofection, and electroporation. Cells containing a nucleic acid encoding a polynucleotide of the TCR described herein may be selected using one or more selectable markers known in the art.

5.1.3. Methods Using CAR-Transduced $T_{SCM}$ Cells

In another aspect, provided herein are methods of generating a population of cells comprising antigen-specific T cells for therapeutic administration to a human patient having or suspected of having a pathogen or cancer, comprising transducing a population of human blood cells with a nucleic acid encoding a CAR recognizing one or more antigens of the pathogen or cancer (preferably at a time when the population of human blood cells has been cultured for 3-5 days), wherein the population of human blood cells contains at least 50% $T_{SCM}$ cells; thereby producing said population of cells comprising antigen-specific T cells. The transducing preferably occurs during days 3-5 in culture, since, as shown by the example section herein (i.e., Section 6), this time is when the $T_{SCM}$ cells exhibit the highest proliferative capacity.

In specific embodiments, the method of generating a population of cells comprising antigen-specific T cells further comprises, after the step of transducing, a step of cryopreserving the transduced population of human blood cells or cells derived therefrom. In a specific embodiment, the method of generating a population of cells comprising antigen-specific T cells further comprises, after the step of cryopreserving, steps of thawing and optionally expanding in culture the transduced population of human blood cells or cells derived therefrom. The cryopreserving and thawing steps can be performed as described in Section 5.1.1, supra.

In specific embodiments, the method of generating a population of cells comprising antigen-specific T cells further comprises, after the step of transducing, a step of expanding in culture the transduced population of human blood cells or cells derived therefrom, wherein the transduced population of human blood cells or cells derived therefrom has not been cryopreserved.

CARs are engineered receptors that provide both antigen binding and immune cell activation functions (Sadelain et al., 2013, Cancer Discovery 3:388-398). They usually comprise an antigen-binding domain (e.g., derived from a monoclonal antibody or the extracellular domain of a receptor), a transmembrane domain, an intracellular domain, and optionally a co-stimulatory domain. CARs can be used to graft the specificity of an antigen-binding domain onto an immune cell such as a T cell.

The population of human blood cells transduced with a nucleic acid encoding a CAR can be generated by any method known in the art, for example, as described in Stauss et al., 2015, Curr Opin Pharmacol 24:113-118; Sharpe and Mount, 2015, Dis Model Mech 8:337-350; or Park et al., 2011, Trends Biotechnol 29:550-557.

The nucleic acid encoding a CAR can be DNA, RNA, or a nucleic acid analog. In specific embodiments, such a nucleic acid may be part of a vector. In a specific embodiment, the vector is an expression vector that is capable of directing the expression of a nucleic acid encoding a polypeptide of the CAR described herein in T cells. Non-limiting examples of expression vectors suitable for directing the expression of a nucleic acid encoding a polypeptide of the CAR described herein include, but are not limited to, plasmids and viral vectors, such as synthetic vectors, lentiviral vectors, replication-defective retroviral vectors, autonomously replicating plasmids. In a specific embodiment, an expression vector used for directing the expression of a nucleic acid encoding a polypeptide of the CAR described herein includes one or more regulatory sequences operably linked to the nucleic acid to be expressed. "Operably linked" is intended to mean that a nucleic acid of interest is linked to the regulatory sequence(s) in a manner which allows for expression of the nucleic acid in T cells. Regulatory sequences include promoters, enhancers and other expression control elements (e.g., polyadenylation signals).

A nucleic acid encoding a polypeptide of the CAR described herein, for example, an expression vector, can be transduced into host cells via conventional transformation or transfection (such as, transfection by a virus, e.g., a retrovirus or lentivirus) techniques. Such techniques include, but are not limited to, calcium phosphate or calcium chloride co-precipitation, DEAE-dextran-mediated transfection, lipofection, and electroporation. Cells containing a nucleic acid encoding a polynucleotide of the CAR described herein may be selected using one or more selectable markers known in the art.

5.1.4. The Population of Human Blood Cells

The population of human blood cells used in accordance with the methods of generating a population of cells comprising antigen-specific T cells described herein contains at least 50% $T_{SCM}$ cells. In a specific embodiment, the population of human blood cells contains at least 60% $T_{SCM}$ cells. In another specific embodiment, the population of human blood cells contains at least 70% $T_{SCM}$ cells. In another specific embodiment, the population of human blood cells contains at least 80% $T_{SCM}$ cells. In another specific embodiment, the population of human blood cells contains at least 90% $T_{SCM}$ cells. In another specific embodiment, the population of human blood cells contains at least 95% $T_{SCM}$ cells. In another specific embodiment, the population of human blood cells contains at least 99% $T_{SCM}$ cells. In another specific embodiment, the population of human blood cells contains 100% $T_{SCM}$ cells. In another specific embodiment, the population of human blood cells contains about 50-75% $T_{SCM}$ cells. In another specific embodiment, the population of human blood cells contains about 75-90% $T_{SCM}$ cells. In another specific embodiment, the population of human blood cells contains about 90-100% $T_{SCM}$ cells. In another specific embodiment, the population of human blood cells contains about 95-100% $T_{SCM}$ cells.

In some embodiments, $T_{SCM}$ cells are $CD3^+CD62L^+CD45RO^-CD95^+$. In other embodiments, $T_{SCM}$ cells are $CD3^+CD62L^+CD45RA^+CD95^+$. In other embodiments, $T_{SCM}$ cells are $CD3^+CCR7^+CD45RA^+CD95^+$. In other embodiments, $T_{SCM}$ cells are $CD3^+CCR7^+CD28^+CD45RO^-CD95^+$. In other embodiments, $T_{SCM}$ cells are $CD3^+CD62L^+CCR7^+CD45RA^+CD95^+$. In other embodiments, $T_{SCM}$ cells are $CD3^+CCR7^+CD45RA^+CD28^+CD95^+$. In other embodiments, $T_{SCM}$ cells are $CD3^+CCR7^+CD45RA^+CD45RO^-CD95^+$. In other embodiments, $T_{SCM}$ cells are $CD3^+CCR7^+CD45RA^+CD127^+CD95^+$. In other embodiments, $T_{SCM}$ cells are $CD3^+CD62L^+CCR7^+CD45RA^+CD27^+CD127^+CD45RO^-CD95^+$. In other embodiments, $T_{SCM}$ cells are $CD3^+CD62L^+CCR7^+CD28^+CD45RA^+CD27^+CD127^+CD103^-CD45RO^-CD95^+$. In various embodiments, the cell surface marker expression of $T_{SCM}$ cells satisfies the following: (i) $CD3^+CD95^+$; (ii) $CD45RO^-$ or $CD45RA^+$, or a combination thereof; and (iii) $CD62L^+$, or $CCR7^+$, or $CD127^+$, or a combination thereof; and optionally (iv) $CD28^+$, or $CD27^+$, or $CD103^-$, or a combination thereof.

In various embodiments, the population of human blood cells contains less than 50% $T_N$ cells. In a specific embodiment, the population of human blood cells contains less than 40% $T_N$ cells. In another specific embodiment, the population of human blood cells contains less than 30% $T_N$ cells. In another specific embodiment, the population of human blood cells contains less than 20% $T_N$ cells. In another specific embodiment, the population of human blood cells contains less than 10% $T_N$ cells. In another specific embodiment, the population of human blood cells contains less than 5% $T_N$ cells. In another specific embodiment, the population of human blood cells contains less than 2% $T_N$ cells. In another specific embodiment, the population of human blood cells contains less than 1% $T_N$ cells. In another specific embodiment, the population of human blood cells contains no $T_N$ cells. In another specific embodiment, the population of human blood cells contains about 50-30% $T_N$ cells. In another specific embodiment, the population of human blood cells contains about 30-20% $T_N$ cells. In another specific embodiment, the population of human blood cells contains about 20-10% $T_N$ cells. In another specific embodiment, the population of human blood cells contains about 10-0% $T_N$ cells. In another specific embodiment, the population of human blood cells contains about 10-5% $T_N$ cells. In another specific embodiment, the population of human blood cells contains about 5-0% $T_N$ cells.

In some embodiments, $T_N$ cells are $CD3^+CD62L^+CD45RO^-CD95^-$. In other embodiments, $T_N$ cells are $CD3^+CD62L^+CD45RA^+CD95^-$. In other embodiments, $T_N$ cells are $CD3^+CCR7^+CD45RA^+CD95^-$. In other embodiments, $T_N$ cells are $CD3^+CCR7^+CD28^+CD45RO^-CD95^-$. In other embodiments, $T_N$ cells are $CD3^+CD62L^+CCR7^+CD45RA^+CD95^-$. In other embodiments, $T_N$ cells are $CD3^+CCR7^+CD45RA^+CD28^+CD95^-$. In other embodiments, $T_N$ cells are $CD3^+CCR7^+CD45RA^+CD45RO^-CD95^-$. In other embodiments, $T_N$ cells are $CD3^+CCR7^+CD45RA^+CD127^+CD95^-$. In other embodiments, $T_N$ cells are $CD3^+CD62L^+CCR7^+CD45RA^+CD27^+CD127^+CD45RO^-CD95^-$. In other embodiments, $T_N$ cells are $CD3^+CD62L^+CCR7^+CD28^+CD45RA^+CD27^+CD127^+CD103^-CD45RO^-CD95^-$. In various embodiments, the cell surface marker expression of $T_N$ cells satisfies the following: (i) $CD3^+CD95^-$; (ii) $CD45RO^-$ or $CD45RA^+$, or a combination thereof; and (iii) $CD62L^+$, or $CCR7^+$, or $CD127^+$, or a combination thereof; and optionally (iv) $CD28^+$, or $CD27^+$, or $CD103^-$, or a combination thereof.

In certain embodiments, the method of generating a population of cells comprising antigen-specific T cells described herein further comprises a step of deriving the population of human blood cells from a human cell sample. The human cell sample can be any cell sample that contains $T_{SCM}$ cells or cells that can be induced in culture to become $T_{SCM}$ cells, such as, but is not limited to, a hematopoietic cell sample, a blood cell sample, a fractionated or unfractionated whole blood sample, a fractionated or unfractionated apheresis collection (e.g., a leukapheresis collection, such as leukopak), PBMCs, or a T cell population (e.g., T cells enriched for from PBMCs). In a specific embodiment, the human cell sample is PBMCs. PBMCs can be isolated from the blood sample by any method known in the art to isolated PBMCs from a blood sample, such as by Ficoll-Hypaque centrifugation as described in Koehne et al., 2000, Blood 96:109-117; Trivedi et al., 2005, Blood 105:2793-2801; or as described in Section 6.2, infra. In another specific embodiment, the human cell sample is a population enriched in T cells from PBMCs. T cells can be enriched for from the PBMCs by any method known in the art to enrich for T cells from a blood sample or PBMCs. Non-limiting exemplary methods for enriching for T cells from PBMCs can be found in Koehne et al., 2000, Blood 96:109-117; Trivedi et al., 2005, Blood 105:2793-2801; Hasan et al., 2009, J Immunol 183: 2837-2850; and Koehne et al., 2015, Biol Blood Marrow Transplant 21: 1663-1678. For example, T cells can be enriched for from PBMCs by sorting the PBMCs using an anti-CD3 antibody and/or depleting from the PBMCs adherent monocytes and natural killer cells.

The step of deriving the population of human blood cells from a human cell sample can employ any known method in the art to produce a population of human blood cells that contains at least 50% $T_{SCM}$ cells from the human cell sample, such as, but is not limited to, sorting the human cell sample to select for $T_{SCM}$ cells or in vitro reprogramming cells in the human cell sample to turn them into $T_{SCM}$ cells. In specific embodiments, the step of deriving the population of human blood cells from a human cell sample comprises affinity selection for cells that express cell surface markers of $T_{SCM}$ cells (e.g., using antibodies to the cell surface markers). In some embodiments, the step of deriving the population of human blood cells from a human cell sample comprises sorting $T_{SCM}$ cells from the human cell sample by fluorescence-activated cell sorting (FACS). In other embodiments, the step of deriving the population of human blood cells from a human cell sample comprises sorting $T_{SCM}$ cells from the human cell sample by magnetic separation.

In specific embodiments, the deriving step comprises enriching for $T_{SCM}$ cells from the human cell sample. $T_{SCM}$ cells exhibit a set of cell surface markers that can be used to distinguish them from other T cell subsets, thus the enriching step can comprise selecting for $T_{SCM}$ cells based on their markers. In a specific embodiment, the enriching step comprises selecting for $T_{SCM}$ cells that are $CD3^+CD62L^+CD45RO^-CD95^+$. In another specific embodiment, the enriching step comprises selecting for $T_{SCM}$ cells that are $CD3^+CD62L^+CD45RA^+CD95^+$. In another specific embodiment, the enriching step comprises selecting for $T_{SCM}$ cells that are $CD3^+CCR7^+CD45RA^+CD95^+$. In another specific embodiment, the enriching step comprises selecting for $T_{SCM}$ cells that are $CD3^+CCR7^+CD28^+CD45RO^-CD95^+$. In another specific embodiment, the enriching step comprises selecting for $T_{SCM}$ cells that are $CD3^+CD62L^+CCR7^+CD45RA^+CD95^+$. In another specific embodiment, the enriching step comprises selecting for $T_{SCM}$ cells that are $CD3^+CCR7^+CD45RA^+CD28^+CD95^+$. In another specific embodiment, the enriching step comprises selecting for $T_{SCM}$ cells that are $CD3^+CCR7^+CD45RA^+CD45RO^-CD95^+$. In another specific embodiment, the enriching step comprises selecting for $T_{SCM}$ cells that are $CD3^+CCR7^+CD45RA^+CD127^+CD95^+$. In another specific embodiment, the enriching step comprises selecting for $T_{SCM}$ cells that are $CD3^+CD62L^+CCR7^+CD45RA^+CD27^+CD127^+CD45RO^-CD95^+$. In another specific embodiment, the enriching step comprises selecting for $T_{SCM}$ cells that are $CD3^+CD62L^+CCR7^+CD28^+CD45RA^+CD27^+CD127^+CD103^-CD45RO^-CD95^+$. In various embodiments, the enriching step comprises selecting for cells whose cell surface marker expression satisfies the following: (i) $CD3^+CD95^+$; (ii) $CD45RO^-$ or $CD45RA^+$, or a combination thereof; and (iii) $CD62L^+$, or $CCR7^+$, or $CD127^+$, or a combination thereof; and optionally (iv) $CD28^+$, or $CD27^+$, or $CD103^-$, or a combination thereof.

In specific embodiments, the deriving step comprises depleting $T_N$ cells from the human cell sample. Naive T cells ($T_N$ cells) are distinguished from $T_{SCM}$ cells by the expression of cell surface marker CD95. In a specific embodiment, the depleting step comprises selecting against (i.e., depleting, or excluding) cells that are $CD3^+CD62L^+CD45RO^-CD95^-$. In another specific embodiment, the depleting step comprises selecting against (i.e., depleting, or excluding) cells that are $CD3^+CD62L^+CD45RA^+CD95^-$. In another specific embodiment, the depleting step comprises selecting against (i.e., depleting, or excluding) cells that are $CD3^+CCR7^+CD45RA^+CD95^-$. In another specific embodiment, the depleting step comprises selecting against (i.e., depleting, or excluding) cells that are $CD3^+CCR7^+CD28^+CD45RO^-CD95^-$. In another specific embodiment, the depleting step comprises selecting against (i.e., depleting, or excluding) cells that are $CD3^+CD62L^+CCR7^+CD45RA^+CD95^-$. In another specific embodiment, the depleting step comprises selecting against (i.e., depleting, or excluding) cells that are $CD3^+CCR7^+CD45RA^+CD28^+CD95^-$. In another specific embodiment, the depleting step comprises selecting against (i.e., depleting, or excluding) cells that are $CD3^+CCR7^+CD45RA^+CD45RO^-CD95^-$. In another specific embodiment, the depleting step comprises selecting against (i.e., depleting, or excluding) cells that are $CD3^+CCR7^+CD45RA^+CD127^+CD95^-$. In another specific embodiment, the depleting step comprises selecting against (i.e., depleting, or excluding) cells that are $CD3^+CD62L^+CCR7^+CD45RA^+CD27^+CD127^+CD45RO^-CD95^-$. In another specific embodiment, the depleting step comprises selecting against (i.e., depleting, or excluding) cells that are $CD3^+CD62L^+CCR7^+CD28^+CD45RA^+CD27^+CD127^+CD103^-CD45RO^-CD95^-$. In various embodiments, the depleting step comprises selecting against (i.e., depleting, or excluding) cells whose cell surface marker expression level satisfies the following: (i) $CD3^+CD95^-$; (ii) $CD45RO^-$ or $CD45RA^+$, or a combination thereof; and (iii) $CD62L^+$, or $CCR7^+$, or $CD127^+$, or a combination thereof; and optionally (iv) $CD28^+$, or $CD27^+$, or $CD103^-$, or a combination thereof.

In preferred embodiments, the population of human blood cells is derived from a human donor that is seropositive for the one or more antigens. In certain embodiments, the population of human blood cells is derived from a human donor that is seronegative for the one or more antigens.

The human donor can be an adult (at least age 16), an adolescent (age 12-15), a child (under age 12), or a fetus. In a specific embodiment, the human donor is an adult.

The term "about" shall be construed so as to allow normal variation.

5.2. Methods of Treating Patients Using the Generated Antigen-Specific T Cells

In another aspect, provided herein are methods of treating a human patient having a pathogen or cancer, comprising: (i) generating a population of cells comprising antigen-specific T cells according to a method described in Section 5.1, supra; and (ii) administering the population of cells comprising antigen-specific T cells to the human patient.

In another aspect, provided herein are methods of treating a human patient having a pathogen or cancer, comprising administering a population of cells comprising antigen-specific T cells to the human patient, wherein the population of cells comprising antigen-specific T cells is the product of a method comprising generating the population of cells comprising antigen-specific T cells according to a method described in Section 5.1, supra.

In specific embodiments, the population of human blood cells is derived from a human donor that is allogeneic to the human patient. In a specific embodiment, the human patient has been the recipient of a transplant from a transplant donor, and the human donor is a third-party donor that is different from the transplant donor. In another specific embodiment, the human patient has been the recipient of a transplant from a transplant donor, and the human donor is the transplant donor. In some embodiments, the transplant is a hematopoietic stem cell transplantation (HSCT), such as a peripheral blood stem cell transplantation, a bone marrow transplantation, or a cord blood transplantation. In other embodiments, the transplant is a solid organ transplant, such as a kidney transplant, a liver transplant, a heart transplant, an intestinal transplant, a pancreas transplant, a lung transplant, or a small bowel transplant.

In specific embodiments, the step of administering of the population of cells comprising antigen-specific T cells does not result in any graft-versus-host disease (GvHD) in the human patient.

5.2.1. Administration and Dosage

The route of administration of the population of cells comprising antigen-specific T cells and the amount to be administered to the human patient can be determined based on the condition of the human patient and the knowledge of the physician. Generally, the administration is intravenous. In certain embodiments, the administering step is by infusion of the population of cells comprising antigen-specific T cells. In specific embodiments, the infusion is bolus intravenous infusion.

In some embodiments, the administering step comprises administering the population of cells comprising antigen-specific T cells to the human patient, at a dose that is less than or equal to about $1 \times 10^5$ cells of the population of cells comprising antigen-specific T cells per kg of the human patient. In a specific embodiment, the administering step comprises administering the population of cells comprising antigen-specific T cells to the human patient, at a dose that is less than or equal to about $5 \times 10^4$ cells of the population of cells comprising antigen-specific T cells per kg of the human patient. In a preferred embodiment, the administering step comprises administering the population of cells comprising antigen-specific T cells to the human patient, at a dose that is less than or equal to about $1 \times 10^4$ cells of the population of cells comprising antigen-specific T cells per kg of the human patient. In another specific embodiment, the administering step comprises administering the population of cells comprising antigen-specific T cells to the human patient, at a dose that is less than or equal to about $5 \times 10^3$ cells of the population of cells comprising antigen-specific T cells per kg of the human patient. In another specific embodiment, the administering step comprises administering the population of cells comprising antigen-specific T cells to the human patient, at a dose that is less than or equal to about $1 \times 10^3$ cells of the population of cells comprising antigen-specific T cells per kg of the human patient. In another specific embodiment, the administering step comprises administering the population of cells comprising antigen-specific T cells to the human patient, at a dose of about $1 \times 10^3$ to $5 \times 10^3$ cells of the population of cells comprising antigen-specific T cells per kg of the human patient. In another specific embodiment, the administering step comprises administering the population of cells comprising antigen-specific T cells to the human patient, at a dose of about $5 \times 10^3$ to $1 \times 10^4$ cells of the population of cells comprising antigen-specific T cells per kg of the human patient. In another specific embodiment, the administering step comprises administering the population of cells comprising antigen-specific T cells to the human patient, at a dose of about $1 \times 10^4$ to $5 \times 10^4$ cells of the population of cells comprising antigen-specific T cells per kg of the human patient. In another specific embodiment, the administering step comprises administering the population of cells comprising antigen-specific T cells to the human patient, at a dose of about $5 \times 10^4$ to $1 \times 10^5$ cells of the population of cells comprising antigen-specific T cells per kg of the human patient.

In other embodiments, the administering step comprises administering the population of cells comprising antigen-specific T cells to the human patient, at a dose that is at least $1 \times 10^5$ cells of the population of cells comprising antigen-specific T cells per kg of the human patient. In a specific embodiment, the administering step comprises administering the population of cells comprising antigen-specific T cells to the human patient, at a dose that is about $5 \times 10^5$ cells of the population of cells comprising antigen-specific T cells per kg of the human patient. In another specific embodiment, the administering step comprises administering the population of cells comprising antigen-specific T cells to the human patient, at a dose that is about $1 \times 10^6$ cells of the population of cells comprising antigen-specific T cells per kg of the human patient. In another specific embodiment, the administering step comprises administering the population of cells comprising antigen-specific T cells to the human patient, at a dose that is about $2 \times 10^6$ cells of the population of cells comprising antigen-specific T cells per kg of the human patient. In another specific embodiment, the administering step comprises administering the population of cells comprising antigen-specific T cells to the human patient, at a dose that is about $3 \times 10^6$ cells of the population of cells comprising antigen-specific T cells per kg of the human patient. In another specific embodiment, the administering step comprises administering the population of cells comprising antigen-specific T cells to the human patient, at a dose that is about $4 \times 10^6$ cells of the population of cells comprising antigen-specific T cells per kg of the human patient. In another specific embodiment, the administering step comprises administering the population of cells comprising antigen-specific T cells to the human patient, at a dose that is about $5 \times 10^6$ cells of the population of cells comprising antigen-specific T cells per kg of the human patient. In another specific embodiment, the administering step comprises administering the population of cells comprising antigen-specific T cells to the human patient, at a dose that is about $6 \times 10^6$ cells of the population of cells comprising antigen-specific T cells per kg of the human patient. In another specific embodiment, the administering step comprises administering the population of cells comprising antigen-specific T cells to the human patient, at a dose that is about $1 \times 10^7$ cells of the population of cells comprising antigen-specific T cells per kg of the human patient. In another specific embodiment, the administering step comprises administering the population of cells comprising antigen-specific T cells to the human patient, at a dose that is about $1 \times 10^5$ to $5 \times 10^5$ cells of the population of cells comprising antigen-specific T cells per kg of the human patient. In another specific embodiment, the administering step comprises administering the population of cells comprising antigen-specific T cells to the human patient, at a dose that is about $5 \times 10^5$ to $1 \times 10^6$ cells of the population of cells comprising antigen-specific T cells per kg of the human patient. In another specific embodiment, the administering step comprises administering the population of cells comprising antigen-specific T cells to the human patient, at a dose that is about $1 \times 10^6$ to $2 \times 10^6$ cells of the population of cells comprising antigen-specific T cells per kg of the human patient. In another specific embodiment, the administering step comprises administering the population of cells comprising antigen-specific T cells to the human patient, at a dose that is about $2 \times 10^6$ to $5 \times 10^6$ cells of the population of cells comprising antigen-specific T cells per kg of the human patient. In another specific embodiment, the administering step comprises administering the population of cells comprising antigen-specific T cells to the human patient, at a dose that is about $5 \times 10^6$ to $1 \times 10^7$ cells of the population of cells comprising antigen-specific T cells per kg of the human patient.

In certain embodiments, the step of administering comprises administering the population of cells comprising antigen-specific T cells to the human patient at the dose described above weekly. In certain embodiments, the step of administering comprises administering the population of cells comprising antigen-specific T cells to the human patient at the dose described above twice weekly. In certain embodiments, the step of administering comprises administering the population of cells comprising antigen-specific T cells to the human patient at the dose described above biweekly. In certain embodiments, the step of administering comprises administering the population of cells comprising antigen-specific T cells to the human patient at the dose described above every three weeks.

In certain embodiments, the step of administering comprises administering at least 2 doses of the population of cells comprising antigen-specific T cells to the human patient. In specific embodiments, the step of administering comprises administering 2, 3, 4, 5, or 6 doses of the population of cells comprising antigen-specific T cells to the human patient. In a specific embodiment, the step of administering comprises administering 2 doses of the population of cells comprising antigen-specific T cells to the human patient. In another specific embodiment, the step of administering comprises administering 3 doses of the population of cells comprising antigen-specific T cells to the human patient. In another specific embodiment, the step of administering comprises administering 4 doses of the population of cells comprising antigen-specific T cells to the human patient.

In specific embodiments, the step of administering comprises administering at least two cycles (e.g., 2, 3, 4, 5, or 6 cycles) of one dose per week of the population of cells comprising antigen-specific T cells for at least two consecutive weeks (e.g., 2, 3, 4, 5, or 6 consecutive weeks), each cycle separated by a washout period during which no dose of the population of cells comprising antigen-specific T cells is administered. In a specific embodiment, the at least two consecutive weeks are 2 consecutive weeks. In a preferred embodiment, the at least two consecutive weeks are 3 consecutive weeks. In another specific embodiment, the at least two consecutive weeks are 4 consecutive weeks. In another specific embodiment, the step of administering comprises administering two, three, four, five, or six cycles of one dose per week of the population of cells comprising antigen-specific T cells for three consecutive weeks, each cycle separated by a washout period during which no dose of the population of cells comprising antigen-specific T cells is administered. In another specific embodiment, the step of administering comprises administering a first cycle of one dose per week of the population of cells comprising antigen-specific T cells for 3 consecutive weeks followed by a washout period during which no dose of the population of cells comprising antigen-specific T cells is administered, followed by a second cycle of said one dose per week of the population of cells comprising antigen-specific T cells for 3 consecutive weeks. In specific embodiments, the washout period is at least about 1 week (e.g., about 1-6 weeks). In specific embodiments, the washout period is about 1, 2, 3, or 4 weeks. In a specific embodiment, the washout period is about 2 weeks. In a preferred embodiment, the washout period is about 3 weeks. In another specific embodiment, the washout period is about 4 weeks. Preferably, an additional cycle is administered only when the previous cycle has not exhibited toxicity (for example, no grade 3-5 serious adverse events, graded according to NCI CTCAE 4.0).

In specific embodiments, the step of administering of the population of cells comprising antigen-specific T cells comprises continuously administering the population of cells comprising antigen-specific T cells at a dose described herein weekly (i.e., there is no week during which the population of cells comprising antigen-specific T cells is not administered, and thus there is no washout period).

In certain embodiments, a first dosage regimen described herein is carried out for a first period of time, followed by a second and different dosage regimen described herein that is carried out for a second period of time, wherein the first period of time and the second period of time are optionally separated by a washout period. In specific embodiments, the washout period is at least about 1 week (e.g., about 1-6 weeks). In specific embodiments, the washout period is about 1, 2, 3, or 4 weeks. In a specific embodiment, the washout period is about 2 weeks. In a preferred embodiment, the washout period is about 3 weeks. In another specific embodiment, the washout period is about 4 weeks. Preferably, the second dosage regimen is carried out only when the first dosage regimen has not exhibited toxicity (for example, no grade 3-5 serious adverse events, graded according to NCI CTCAE 4.0).

The term "about" shall be construed so as to allow normal variation.

5.2.2. Serial Treatment with Different Cell Populations

In certain embodiments, the method of treating a human patient having a pathogen or cancer as described above further comprises, after administering to the human patient a first population of cells comprising antigen-specific T cells generated according to a method described in Section 5.1, supra, administering to the human patient a second population of cells comprising antigen-specific T cells generated according to a method described in Section 5.1, supra, wherein the antigen-specific T cells in the second population of cells comprising antigen-specific T cells are restricted by a different HLA allele (different from the HLA allele by which antigen-specific cells contained in the first population of cells comprising antigen-specific T cells are restricted) shared with the diseased cells in the human patient. In a specific embodiment, the method of treating a human patient having a pathogen or cancer comprises administering a first cycle of one dose per week of the first population of cells comprising antigen-specific T cells, for at least two consecutive weeks (e.g., 2, 3, 4, 5, or 6 consecutive weeks), optionally followed by a washout period during which no dose of any population of cells comprising antigen-specific T cells is administered, and followed by a second cycle of one dose per week of the second population of cells comprising antigen-specific T cells for at least two consecutive weeks (e.g., 2, 3, 4, 5, or 6 consecutive weeks). In specific embodiments, the washout period is at least about 1 week (e.g., about 1-6 weeks). In specific embodiments, the washout period is about 1, 2, 3, or 4 weeks. In a specific embodiment, the washout period is about 2 weeks. In a preferred embodiment, the washout period is about 3 weeks. In certain embodiments, the human patient has no response, an incomplete response, or a suboptimal response (i.e., the human patient may still have a substantial benefit from continuing treatment, but has reduced chances of optimal long-term outcomes) after administering the first population of cells comprising antigen-specific T cells and prior to administering the second population of cells comprising antigen-specific T cells.

The first and second populations of cells comprising antigen-specific T cells can each be administered by any route and any dosage regimen as described in Section 5.2.1, supra.

In specific embodiments, two populations of cells comprising antigen-specific T cells that are each restricted (i.e., antigen-specific T cells in the two populations of cells are each restricted) by a different HLA allele shared with the diseased cells in the human patient are administered serially. In specific embodiments, three populations of cells comprising antigen-specific T cells that are each restricted (i.e., antigen-specific T cells in the three populations of cells are each restricted) by a different HLA allele shared with the diseased cells in the human patient are administered serially. In specific embodiments, four populations of cells comprising antigen-specific T cells that are each restricted (i.e., antigen-specific T cells in the four populations of cells are each restricted) by a different HLA allele shared with the diseased cells in the human patient are administered serially. In specific embodiments, more than four populations of cells comprising antigen-specific T cells that are each restricted (i.e., antigen-specific T cells in the more than four populations of cells are each restricted) by a different HLA allele shared with the diseased cells in the human patient are administered serially.

5.2.3. Additional Therapies

In specific embodiments, the method of treating a human patient having a pathogen or cancer further comprises concurrently treating the human patient with a second therapy for the pathogen or cancer, which second therapy is not treatment with a population of cells comprising antigen-specific T cells according to the invention, for example, at about the same time, the same day, or same week, or same treatment period (treatment cycle) during which the population of cells comprising antigen-specific T cells is administered, or on similar dosing schedules, or on different but overlapping dosing schedules. In specific embodiments, no second therapy for the pathogen or cancer is concurrently administered to the human patient over a period of time over which the population of cells is repeatedly administered to the human patient. In specific embodiments, the method of treating a human patient having a pathogen or cancer further comprises, before the administering step, a step of treating the human patient with a second therapy for the pathogen or cancer, which is not treatment with a population of cells comprising antigen-specific T cells according to the invention.

5.3. The Population of Cells Comprising Antigen-Specific T Cells and Their Characterization In another aspect, provided herein are isolated populations of cells comprising antigen-specific T cells for therapeutic administration to a human patient having or suspected of having a pathogen or cancer, wherein the isolated population of cells comprising antigen-specific T cells is the product of a method comprising generating the population of cells comprising antigen-specific T cells according to a method described in Section 5.1, supra. In specific embodiments, provided herein is an isolated population of cells comprising antigen-specific T cells for therapeutic administration to a human patient having or suspected of having a pathogen or cancer, wherein the isolated population of cells comprising antigen-specific T cells is the product of a method comprising generating the population of cells comprising antigen-specific T cells according to a method described in Section 5.1, supra, and wherein the population of cells comprising antigen-specific T cells is cryopreserved.

In specific embodiments, the isolated population of cells comprising antigen-specific T cells comprises CD8+ T cells. In specific embodiments, the isolated population of cells comprising antigen-specific T cells comprises CD4+ T cells. In specific embodiments, the isolated population of cells comprising antigen-specific T cells comprises both CD8+ and CD4+ T cells.

To be suitable for therapeutic administration to a human patient in adoptive immunotherapy, the population of cells comprising antigen-specific T cells generated by a method described in Section 5.1, supra, preferably (1) exhibits substantial cytotoxicity toward fully or partially HLA-matched (relative to the human donor of the population of human blood cells) antigen presenting cells that are loaded with or genetically engineered to express one or more peptides or proteins derived from the one or more antigens of the pathogen or cancer; (2) lacks substantial alloreactivity; and/or (3) is restricted (i.e., the antigen-specific T cells contained in the population of cells comprising antigen-specific T cells are restricted) by an HLA allele shared with the diseased cells in the human patient, and/or shares (i.e., the antigen-specific T cells contained in the population of cells comprising antigen-specific T cells share) at least 2 HLA alleles (e.g., at least 2 out of 8 HLA alleles) with the diseased cells in the human patient. Thus, preferably, cytotoxicity, alloreactivity, information as to which HLA allele(s) the population of cells comprising antigen-specific T cells is restricted (i.e., to which HLA allele(s) the antigen-specific T cells contained in the population of cells comprising antigen-specific T cells are restricted), and/or the HLA assignment of the population of cells comprising antigen-specific T cells (i.e., the HLA assignment of the antigen-specific T cells contained in the population of cells comprising antigen-specific T cells) are measured by a method known in the art before administration to a human patient (for example, such a method as described in Koehne et al., 2000, Blood 96:109-117; Trivedi et al., 2005, Blood 105:2793-2801; Haque et al., 2007, Blood 110:1123-1131; Hasan et al., 2009, J Immunol 183: 2837-2850; Feuchtinger et al., 2010, Blood 116:4360-4367; Doubrovina et al., 2012, Blood 120:1633-1646; Leen et al., 2013, Blood 121:5113-5123; Papadopoulou et al., 2014, Sci Transl Med 6:242ra83; Sukdolak et al., 2013, Biol Blood Marrow Transplant 19:1480-1492; Koehne et al., 2015, Biol Blood Marrow Transplant 21: 1663-1678; or International Patent Application Publication No. WO 2016/073550).

Also provided herein is a cell bank comprising a plurality of isolated populations of cells comprising antigen-specific T cells described herein. Preferably, information as to cytotoxicity, alloreactivity, and/or HLA restriction and/or assignment, as described herein, is ascertained for each of the plurality of isolated populations of cells comprising antigen-specific T cells contained in the cell bank, and linked to the identifier of the corresponding population of cells comprising antigen-specific T cells, so as to facilitate the selection of a suitable population of cells comprising antigen-specific T cells from the plurality for therapeutic administration to a human patient.

It is contemplated that, in specific embodiments of the foregoing characterization of the population of cells comprising antigen-specific T cells described herein, a different method of measuring the potency of the population of cells comprising antigen-specific T cells (such as an assay that instead of measuring cell lysis, measures, for example, CD107 degranulation or release of a cytokine such as IFN-γ), in lieu of a cytotoxicity assay, is used.

5.3.1. Cytotoxicity

The cytotoxicity of a population of cells comprising antigen-specific T cells generated by a method described in Section 5.1, supra, toward fully or partially HLA-matched (relative to the human donor of the population of human blood cells) antigen presenting cells can be determined by any assay known in the art to measure T cell mediated cytotoxicity. The assay can be performed using the population of cells comprising antigen-specific T cells directly, an aliquot thereof, or a precursor cell population that indicates the cytotoxicity of the population of cells comprising antigen-specific T cells. In a specific embodiment, the cytotoxicity is determined by a standard $^{51}$Cr release assay as described in Trivedi et al., 2005, Blood 105:2793-2801 or Hasan et al., 2009, J Immunol 183: 2837-2850.

In certain embodiments, the population of cells comprising antigen-specific T cells generated by a method described in Section 5.1, supra, exhibits substantial cytotoxicity in vitro toward (e.g., exhibits substantial lysis of) fully or partially HLA matched antigen presenting cells that are loaded with or genetically engineered to express one or more peptides or proteins derived from the one or more antigens of the pathogen or cancer. Preferably, the fully or partially HLA-matched antigen presenting cells are fully HLA-matched antigen presenting cells (e.g., antigen presenting cells derived from the human donor). In specific embodiments, the population of cells comprising antigen-specific T cells generated by a method described in Section 5.1, supra, exhibits lysis of greater than or equal to 20%, 25%, 30%, 35%, or 40% of the fully or partially HLA-matched antigen presenting cells that are loaded with or genetically engineered to express one or more peptides or proteins derived from the one or more antigens of the pathogen or cancer. In a specific embodiment, the population of cells comprising antigen-specific T cells generated by a method described in Section 5.1, supra, exhibits lysis of greater than or equal to 20% of the fully or partially HLA-matched antigen presenting cells that are loaded with or genetically engineered to express one or more peptides or proteins derived from the one or more antigens of the pathogen or cancer.

Antigen presenting cells that can be used in the cytotoxicity assay include, but are not limited to, dendritic cells, phytohemagglutinin (PHA)-lymphoblasts, macrophages, B-cells that generate antibodies, EBV-BLCL cells, and artificial antigen presenting cells (AAPCs).

In specific embodiments, the fully or partially HLA-matched antigen presenting cells used in the cytotoxicity assay are loaded with a pool of peptides derived from the one or more antigens of the pathogen or cancer. The pool of peptides, can be, for example, a pool of overlapping peptides (e.g., pentadecapeptides) spanning the sequence of the one or more antigens of the pathogen or cancer.

5.3.2. Alloreactivity

Alloreactivity of a population of cells comprising antigen-specific T cells generated by a method described in Section 5.1, supra, can be measured using a cytotoxicity assay known in the art to measure T cell mediated cytotoxicity, such as a standard $^{51}$Cr release assay, as described in Section 5.3.1, supra, but with antigen presenting cells that are not loaded with or genetically engineered to express one or more peptides or proteins derived from the one or more antigens of the pathogen or cancer, and/or HLA-mismatched (relative to the human donor of the population of human cells) antigen presenting cells. The assay can be performed using the population of cells comprising antigen-specific T cells directly, an aliquot thereof, or a precursor cell population that indicates the alloreactivity of the population of cells comprising antigen-specific T cells. A population of cells comprising antigen-specific T cells that lacks substantial alloreactivity results generally in the absence of graft-versus-host disease (GvHD) when administered to a human patient.

In certain embodiments, the population of cells comprising antigen-specific T cells generated by a method described in Section 5.1, supra, lacks substantial cytotoxicity in vitro toward antigen presenting cells that are not loaded with or genetically engineered to express one or more peptides or proteins derived from the one or more antigens of the pathogen or cancer. In preferred embodiments, such antigen-presenting cells are fully or partially HLA-matched antigen presenting cells (relative to the human donor of the population of human blood cells) (e.g., antigen presenting cells derived from the human donor of the population of human blood cells). In specific embodiments, the population of cells comprising antigen-specific T cells generated by a method described in Section 5.1, supra, lyses less than or equal to 15%, 10%, 5%, 2%, or 1% of antigen presenting cells that are not loaded with or genetically engineered to express one or more peptides or proteins derived from the one or more antigens of the pathogen or cancer. In a specific embodiment, the population of cells comprising antigen-specific T cells generated by a method described in Section 5.1, supra, lyses less than or equal to 10% of antigen presenting cells that are not loaded with or genetically engineered to express one or more peptides or proteins derived from the one or more antigens of the pathogen or cancer. In another specific embodiment, the population of cells comprising antigen-specific T cells generated by a method described in Section 5.1, supra, lyses less than or equal to 5% of antigen presenting cells that are not loaded with or genetically engineered to express one or more peptides or proteins derived from the one or more antigens of the pathogen or cancer.

In certain embodiments, the population of cells comprising antigen-specific T cells generated by a method described in Section 5.1, supra, lacks substantial cytotoxicity in vitro toward HLA-mismatched (relative to the human donor of the population of human blood cells) antigen presenting cells. In some embodiments, such antigen-presenting cells are loaded with or genetically engineered to express one or more peptides or proteins derived from the one or more antigens of the pathogen or cancer. In other embodiments, such antigen-presenting cells are not loaded with or genetically engineered to express one or more peptides or proteins derived from the one or more antigens of the pathogen or cancer. In specific embodiments, the population of cells comprising antigen-specific T cells generated by a method described in Section 5.1, supra, lyses less than or equal to 15%, 10%, 5%, 2%, or 1% of HLA-mismatched (relative to the human donor of the population of human blood cells) antigen presenting cells. In a specific embodiment, the population of cells comprising antigen-specific T cells generated by a method described in Section 5.1, supra, lyses less than or equal to 10% of HLA-mismatched (relative to the human donor of the population of human blood cells) antigen presenting cells. In another specific embodiment, the population of cells comprising antigen-specific T cells generated by a method described in Section 5.1, supra, lyses less than or equal to 5% of HLA-mismatched (relative to the human donor of the population of human blood cells) antigen presenting cells.

In certain embodiments, the population of cells comprising antigen-specific T cells generated by a method described in Section 5.1, supra, lacks substantial cytotoxicity in vitro toward antigen presenting cells that are not loaded with or genetically engineered to express one or more peptides or proteins derived from the one or more antigens of the pathogen or cancer, as described above, and lacks substantial cytotoxicity in vitro toward HLA-mismatched antigen presenting cells as described above.

Antigen presenting cells that can be used in the alloreactivity assay include, but are not limited to, dendritic cells, phytohemagglutinin (PHA)-lymphoblasts, macrophages, B-cells that generate antibodies, EBV-BLCL cells, and artificial antigen presenting cells (AAPCs).

5.3.3. HLA Type

The HLA assignment (i.e., the HLA loci type) of a population of cells comprising antigen-specific T cells generated by a method described in Section 5.1, supra, (i.e., the HLA assignment of the antigen-specific T cells contained in the population of cells comprising antigen-specific T cells) and/or the HLA assignment of the diseased cells in the human patient to be treated can be ascertained (i.e., typed) by any method known in the art for typing HLA alleles. The assignment can be performed using the population of cells comprising antigen-specific T cells directly, an aliquot thereof, or a precursor cell population that indicates the HLA assignment of the population of cells comprising antigen-specific T cells. Non-limiting exemplary methods for ascertaining the HLA assignment can be found in ASHI Laboratory Manual, Edition 4.2 (2003), American Society for Histocompatibility and Immunogenetics; ASHI Laboratory Manual, Supplements 1 (2006) and 2 (2007), American Society for Histocompatibility and Immunogenetics; Hurley, "DNA-based typing of HLA for transplantation." in Leffell et al., eds., 1997, Handbook of Human Immunology, Boca Raton: CRC Press; Dunn, 2011, Int J Immunogenet 38:463-473; Erlich, 2012, Tissue Antigens, 80:1-11; Bontadini, 2012, Methods, 56:471-476; and Lange et al., 2014, BMC Genomics 15: 63. In specific embodiments, at least 4 HLA loci (preferably HLA-A, HLA-B, HLA-C, and HLA-DR) are typed. In a specific embodiment, 4 HLA loci (preferably HLA-A, HLA-B, HLA-C, and HLA-DR) are typed. In another specific embodiment, 6 HLA loci are typed. In another specific embodiment, 8 HLA loci are typed.

In general, high-resolution typing is preferable for HLA typing. The high-resolution typing can be performed by any method known in the art, for example, as described in ASHI Laboratory Manual, Edition 4.2 (2003), American Society for Histocompatibility and Immunogenetics; ASHI Laboratory Manual, Supplements 1 (2006) and 2 (2007), American Society for Histocompatibility and Immunogenetics; Flomenberg et al., Blood, 104:1923-1930; Kögler et al., 2005, Bone Marrow Transplant, 36:1033-1041; Lee et al., 2007, Blood 110:4576-4583; Erlich, 2012, Tissue Antigens, 80:1-11; Lank et al., 2012, BMC Genomics 13:378; or Gabriel et al., 2014, Tissue Antigens, 83:65-75.

In specific embodiments, the HLA assignment of the diseased cells in the human patient to be treated is ascertained by typing the origin of the diseased cells (e.g., the human patient or a transplant donor for the human patient, as the case may be). The origin of the diseased cells can be determined by any method known in the art, for example, by analyzing variable tandem repeats (VTRs) (which is a method that uses unique DNA signature of small DNA sequences of different people to distinguish between the recipient and the donor of a transplant), or by looking for the presence or absence of chromosome Y if the donor and the recipient of a transplant are of different sexes (which is done by cytogenetics or by FISH (fluorescence in situ hybridization)).

The HLA allele by which the population of cells comprising antigen-specific T cells generated by a method described in Section 5.1, supra, is restricted (i.e., the HLA allele by which the antigen-specific T cells contained in the population of cells comprising antigen-specific T cells are restricted) can be determined by any method known in the art, for example, as described in Trivedi et al., 2005, Blood 105:2793-2801; Barker et al., 2010, Blood 116:5045-5049; Hasan et al., 2009, J Immunol, 183:2837-2850; Doubrovina et al., 2012, Blood 120:1633-1646; or International Patent Application Publication No. WO 2016/073550. The determination can be performed using the population of cells comprising antigen-specific T cells directly, an aliquot thereof, or a precursor cell population that indicates the HLA allele by which the population of cells comprising antigen-specific T cells is restricted (i.e., the HLA allele by which the antigen-specific T cells contained in the population of cells comprising antigen-specific T cells are restricted).

In some embodiments, the antigen-specific T cells contained in the population of cells comprising antigen-specific T cells are restricted by an HLA allele shared with the diseased cells in the human patient to be treated. In other embodiments, the antigen-specific T cells contained in the population of cells comprising antigen-specific T cells share at least 2 HLA alleles (for example, at least 2 out of 8 HLA alleles, such as two HLA-A alleles, two HLA-B alleles, two HLA-C alleles, and two HLA-DR alleles) with the diseased cells in the human patient to be treated. In other embodiments, the antigen-specific T cells contained in the population of cells comprising antigen-specific T cells are restricted by an HLA allele shared with diseased cells in the human patient to be treated, and share at least 2 HLA alleles (for example, at least 2 out of 8 HLA alleles, such as two HLA-A alleles, two HLA-B alleles, two HLA-C alleles, and two HLA-DR alleles) with the diseased cells in the human patient to be treated.

5.3.4. Composition and Kits

In another aspect, provided herein are pharmaceutical compositions comprising a therapeutically effective amount of an isolated population of cells comprising antigen-specific T cells described herein, and a pharmaceutically acceptable carrier. In a preferred embodiment, the pharmaceutical composition is in a cryopreserved form.

The pharmaceutical acceptable carrier can be any physiologically-acceptable solution suitable for the storage and/or therapeutic administration of T cells, for example, a saline solution, a buffered saline solution, or a bio-compatible solution comprising one or more cryopreservatives (e.g., phosphate-buffered saline containing 7% DMSO, 5% dextrose and 1% dextran; hypothermosol containing 5% DMSO and 5% human serum albumin; normal saline containing 10% DMSO and 16% human serum albumin; or normal saline containing 10% DMSO and 15% human serum albumin).

The population of cells comprising antigen-specific T cells can be stored in the pharmaceutical composition at any concentration desirable for its long-term storage and convenience of storage and handling. In a specific embodiment, the population of cells comprising antigen-specific T cells is stored in the pharmaceutical composition at a concentration of about $5 \times 10^6$ cells/mL. In another specific embodiment, the population of cells comprising antigen-specific T cells is stored in the pharmaceutical composition at a concentration of about $10 \times 10^6$ cells/mL. In another specific embodiment, the population of cells comprising antigen-specific T cells is stored in the pharmaceutical composition at a concentration of about $20 \times 10^6$ cells/mL. In another specific embodiment, the population of cells comprising antigen-specific T cells is stored in the pharmaceutical composition at a concentration of about $50 \times 10^6$ cells/mL. In another specific embodiment, the population of cells comprising antigen-specific T cells is stored in the pharmaceutical composition at a concentration of about $100 \times 10^6$ cells/mL. In another specific embodiment, the population of cells comprising antigen-specific T cells is stored in the pharmaceutical composition at a concentration of about $200 \times 10^6$ cells/mL. In another specific embodiment, the population of cells comprising antigen-specific T cells is stored in the pharmaceutical composition at a concentration of about $500 \times 10^6$ cells/mL. In another specific embodiment, the population of cells comprising antigen-specific T cells is stored in the pharmaceutical composition at a concentration of about 1 to $10 \times 10^6$ cells/mL. In another specific embodiment, the population of cells comprising antigen-specific T cells is stored in the pharmaceutical composition at a concentration of about 10 to $100 \times 10^6$ cells/mL. In another specific embodiment, the population of cells comprising antigen-specific T cells is stored in the pharmaceutical composition at a concentration of about 100 to $1000 \times 10^6$ cells/mL.

Also provided herein are kits comprising in one or more containers the pharmaceutical composition described herein. In specific embodiments, the kits further comprise a second pharmaceutical composition comprising a second compound or biological product for treating the pathogen infection or cancer.

Optionally associated with such one or more containers can be a notice in the form prescribed by a governmental agency regulating the manufacture, use or sale of pharmaceuticals or biological products, which notice reflects approval by the agency of manufacture, use or sale for human administration.

The pharmaceutical compositions and kits encompassed herein can be used in accordance with the methods of treating a human patient as provided in this disclosure.

5.4. Antigen Specificity and Patients

The one or more antigens of a pathogen, as disclosed above, can be one or more peptides or proteins whose expressions are unique to the pathogen.

The pathogen can be a virus, bacterium, fungus, helminth or protist. In some embodiments, the pathogen is a virus (such as a virus that has a latency). In a specific embodiment, the virus is cytomegalovirus (CMV). In an aspect of the specific embodiment, the one or more antigens of CMV is CMV pp65, CMV IE1, or a combination thereof. In another aspect of the specific embodiment, the one or more antigens of CMV is CMV pp65.

In another specific embodiment, the virus is Epstein-Barr virus (EBV). In an aspect of the specific embodiment, the one or more antigens of EBV is EBNA1, EBNA2, EBNA3A, EBNA3B, EBNA3C, LMP1, LMP2, or a combination thereof. In another aspect of the specific embodiment, the one or more antigens of EBV is EBNA1, LMP1, LMP2, or a combination thereof.

In another specific embodiment, the virus is BK virus (BKV), John Cunningham virus (JCV), herpesvirus (such as human herpesvirus-6 or human herpesvirus-8), adenovirus (ADV), human immunodeficiency virus (HIV), influenza virus, ebola virus, poxvirus, rhabdovirus, or paramyxovirus. In another embodiment, the virus is hepatitis B virus (HBV), hepatitis C virus (HCV), herpes simplex virus (HSV), varicella zoster virus (VZV), human papillomavirus (HPV), or Merkel cell polyomavirus (MCV).

In specific embodiments of the methods of generating a population of cells comprising antigen-specific cells described herein, the ex vivo sensitizing step comprises ex vivo sensitizing the population of human blood cells to one or more antigens of the pathogen described herein. In a specific embodiment of the methods of generating a population of cells comprising antigen-specific cells described herein, the ex vivo sensitizing step comprises ex vivo sensitizing the population of human blood cells to one or more antigens of CMV. In another specific embodiment of the methods of generating a population of cells comprising antigen-specific cells described herein, the ex vivo sensitizing step comprises ex vivo sensitizing the population of human blood cells to one or more antigens of EBV. In another specific embodiment of the methods of generating a population of cells comprising antigen-specific cells described herein, the ex vivo sensitizing step comprises ex vivo sensitizing the population of human blood cells to one or more antigens of BKV, JCV, herpesvirus (such as human herpesvirus-6 or human herpesvirus-8), adenovirus, human immunodeficiency virus, influenza virus, ebola virus, poxvirus, rhabdovirus, or paramyxovirus.

In specific embodiments of the methods of treating a human patient described herein, the human patient has an infection of the pathogen. In some embodiments of the methods of treating a human patient described herein, the human patient has a CMV infection (e.g., CMV viremia, CMV retinitis, CMV pneumonia, CMV hepatitis, CMV colitis, CMV encephalitis, CMV meningoencephalitis, CMV-positive meningioma, or CMV-positive glioblastoma multiforme). In other embodiments of the methods of treating a human patient described herein, the human patient has an EBV-positive lymphoproliferative disorder (EBV-LPD) (for example, an EBV-positive post-transplant lymphoproliferative disorder) resulting from EBV infection, such as B-cell hyperplasia, lymphoma (such as, B-cell lymphoma, non-Hodgkin lymphoma (e.g., diffuse large B-cell lymphoma, for example in the elderly), T-cell lymphoma, EBV-positive Hodgkin's lymphoma, Burkitt lymphoma), polymorphic or monomorphic EBV-LPD, autoimmune lymphoproliferative syndrome, or mixed PTLD (post-transplant lymphoproliferative disorder). In other embodiments of the methods of treating a human patient described herein, the human patient has an EBV-positive nasopharyngeal carcinoma. In other embodiments of the methods of treating a human patient described herein, the human patient has an EBV-positive gastric cancer. In other embodiments of the methods of treating a human patient described herein, the human patient has an EBV+ leiomyosarcoma. In other embodiments of the methods of treating a human patient described herein, the human patient has an EBV-positive NK/T lymphoma.

In other embodiments, the pathogen is a bacterium, such as *Mycobacterium tuberculosis.*

The one or more antigens of a cancer, as disclosed above, can be one or more peptides or proteins whose expressions are higher in cancerous cells (of the corresponding type of cancer) relative to non-cancerous cells, or one or more peptides or proteins which are uniquely expressed in cancerous cells (of the corresponding type of cancer) relative to non-cancerous cells.

The cancer can be a blood cancer, such as, but is not limited to: acute lymphoblastic leukemia, chronic lymphocytic leukemia, acute myelogenous leukemia, chronic myelogenous leukemia, hairy cell leukemia, T-cell prolymphocytic leukemia, Large granular lymphocytic leukemia, adult T-cell leukemia, plasma cell leukemia, Hodgkin lymphoma, Non-Hodgkin lymphoma, or multiple myeloma. In a specific embodiment, the cancer is multiple myeloma or plasma cell leukemia. In an aspect of the specific embodiment, the one or more antigens of the cancer is Wilms tumor 1 (WT1).

The cancer can also be a solid tumor cancer, including, but is not limited to, a sarcoma, a carcinoma, a lymphoma, a germ cell tumor, or a blastoma. The solid tumor cancer that can be, such as, but not limited to: a cancer of the breast, lung, ovary, stomach, pancreas, larynx, esophagus, testes, liver, parotid, biliary tract, colon, rectum, cervix, uterus, endometrium, kidney, bladder, prostate, thyroid, brain, or skin.

In specific embodiments of the methods of generating a population of cells comprising antigen-specific cells described herein, the ex vivo sensitizing step comprises ex vivo sensitizing the population of human blood cells to one or more antigens of the cancer described herein. In a specific embodiment of the methods of generating a population of cells comprising antigen-specific cells described herein, the ex vivo sensitizing step comprises ex vivo sensitizing the population of human blood cells to WT1.

In specific embodiments of the methods of treating a human patient described herein, the human patient has a cancer described herein. In some embodiments of the methods of treating a human patient described herein, the human patient has multiple myeloma or plasma cell leukemia (e.g., a WT1-positive multiple myeloma or plasma cell leukemia).

In a specific embodiment, the human patient is an adult (at least age 16). In another specific embodiment, the human patient is an adolescent (age 12-15). In another specific embodiment, the patient is a child (under age 12).

In a specific embodiment, the human patient treated with a method described herein has failed a previous therapy for the pathogen or cancer, which previous therapy is not treatment with a population of cells comprising antigen-specific T cells according to the invention, due to resistance to or intolerance of the previous therapy. A disease is considered resistant to a therapy, if it has no response, or has an incomplete response (a response that is less than a complete remission), or progresses, or relapses after the therapy. The previous therapy could be an antiviral agent known in the art (e.g., an antiviral drug or antibody), or an anti-cancer therapy known in the art (e.g., a chemotherapy or a radiotherapy), as the case may be.

6. EXAMPLE

Certain embodiments provided herein are illustrated by the following non-limiting example, which demonstrates that stem cell-like memory T cells ($T_{SCM}$ cells) are an advantageous source of T cells to generate antigen-specific T cells for adoptive immunotherapy. The results described herein suggest that $Tet^+$ $T_{SCM}$ cells rather than $Tet^+$ $T_N$ cells are the principal reservoir for rapid repopulation of immunodominant T cells in the circulation.

6.1. Summary

Latent CMV infection is controlled by a limited repertoire of immunodominant T cells specific for viral peptides. Antigen-specific T cell subsets responsible for maintaining memory T cells and repopulating them in response to periodic viral reactivations remain unclear. In this example described herein, T cells specific for CMVpp65 were generated from naive T cell ($T_N$ cell), stem cell-like memory T cell ($T_{SCM}$ cell), central memory T cell ($T_{CM}$ cell) and effector memory T cell ($T_{EM}$ cell) subsets isolated from the blood of HLA-A*0201 seropositive human donors, and NLV-HLA-A*0201 Tetramer $(Tet)^+$ T cells from each of these subsets were comparatively characterized. Following in vitro sensitization, $Tet^+$ T cells were regularly generated from $CD62L^+CD45RO^-CD95^-$ $T_N$ cells and from $CD62L^+CD45RO^-CD95^+$ $T_{SCM}$ cells, as well as $T_{CM}$ cells and $T_{EM}$ cells. $Tet^+$ T cells derived from each of the $T_N$, $T_{SCM}$, $T_{CM}$ and $T_{EM}$ subsets generated IFN-γ, TNF-α and granzyme B. $Tet^+$ T cells derived from each subset also expressed similar levels of PD-1 and KLRG-1. However, $Tet^+$ T cells derived from the $T_N$ subset and those derived from the $T_{SCM}$ subset expressed higher levels of CD27 and lower levels of CD57 than those derived from the $T_{CM}$ or $T_{EM}$ subset. $Tet^+$ T cells derived from the $T_{SCM}$ subset were distinguished from those derived from the $T_N$, $T_{CM}$ and $T_{EM}$ subsets by a significantly greater level of proliferation and by their rapid and selective expansion of NLV-specific T cells bearing TCRs identical in sequence to those expressed by $T_{EM}$ and $T_{CM}$ in the blood. The example described herein suggests that $Tet^+$ $T_{SCM}$ cells rather than $Tet^+$ $T_N$ cells are the principal reservoir for rapid repopulation of immunodominant T cells in the circulation.

6.2. Materials and Methods

6.2.1. Donors

Blood samples were obtained from 12 healthy volunteer HLA-A*0201$^+$ CMV-seropositive donors. High resolution HLA typing was performed by analysis of HLA allele-specific nucleotide sequences using standard high-resolution typing techniques. CMV serostatus was determined by standard serologic techniques in the clinical microbiology laboratory at Memorial Sloan Kettering Cancer Center.

6.2.2. Generation of CMV-Specific T Cells

Peripheral blood mononuclear cells (PBMCs) were isolated from whole blood by Ficoll-Hypaque density gradient separation (Accurate Chemical & Scientific Corporation, Westbury, N.Y. USA), from which T cells were enriched by depletion of $CD19^+$, $CD14^+$, and $CD56^+$ cells, using mAb-coated immunomagnetic beads (Pan T-Cell Isolation Kit II, Miltenyi Biotec Inc, Auburn, Calif. USA). Enriched T cells were labeled with fluorescent Abs: anti-CD3 PerCP, anti-CD45RO PE, anti-CD95 APC, anti-CD62L FITC (all purchased from BD Biosciences), and anti-CD45RA (eBiosciences, CA, USA). T cell populations representing $T_N$, $T_{SCM}$, $T_{CM}$ and $T_{EM}$ cells were gated and sorted on a BD FACS Aria-II SORT (BD Biosciences) based on the following markers: $T_{SCM}$ population as $CD3^+CD45RO^-CD62L^+CD95^+$, $T_N$ population as $CD3^+CD45RO^-CD62L^+CD95^-$, and the $T_{CM}$ and $T_{EM}$ populations as $CD3^+CD45RO^+CD62L^+$ and $CD3^+CD45RO^+CD62L^-$ respectively. Sorted T cell subsets ($1 \times 10^6$) were then sensitized with irradiated $HLA-A0201^+$ and $CMVpp65^+$ artificial antigen presenting cells (AAPCs) ($0.1 \times 10^6$) as previously described (Hasan et al., 2009, J Immunol 183:2837-2850) and were additionally cultured in the presence of irradiated autologous PBMCs ($2 \times 10^6$) as feeder cells in culture medium X-VIVO™ 15 with gentamicin (Lonza, Allendale N.J., USA) and 15% heat inactivated human serum (Gemini, CA, USA) in humidified incubators at 37° C. and 5% $CO_2$. T cells were supplemented with IL-7 (5 ng/ml), and IL-15 (5 ng/ml) on day 4 and day 7 after culture initiation and were re-stimulated every 10 days with AAPCs and autologous PBMC feeders. After day 12, IL-7 (5 ng/ml), IL-15 (5 ng/ml), and IL-2 (20 U/ml) were supplemented to T cell cultures every other day.

6.2.3. Quantitation of Antigen-Specific CD8+ T Cells by Tetramer Analysis

CMVpp65 specific T cells responsive to the NLV peptide within the cultured T cells were enumerated by Tetramer analysis as previously described (Hasan et al., 2009, J Immunol 183:2837-2850). Commercially available CMVpp65 MHC-peptide tetramers for HLA-A*0201 and A*2402-bearing peptide sequences NLVPMVATV (SEQ ID NO:1) and QYDPVAALF (SEQ ID NO:2) (Beckman Coulter) were used. Briefly, T cells were incubated with CD3 FITC, CD8 PE, CD4 PerCP (BD Biosciences) and an APC-conjugated tetrameric complex for 20 mins on ice, washed and analyzed by FACS using a FACSCalibur flow cytometer with dual laser for four-color capability. Data were analyzed using FlowJo software (Tree Star). T cells were gated on CD3- and CD8-positive cells to determine the percentage of tetramer-positive $CD8^+$ T lymphocytes.

6.2.4. Phenotypic Analysis of T Cell Subsets

T cell subsets were further characterized by flow cytometry using specific T cell memory and co-stimulatory markers. T cells were labeled with fluorescent antibodies against CCR7 PE (BD Biosciences), CD27 FITC (Miltenyi Biotec), CD57 FITC (Miltenyi Biotec), CD127 PE (Miltenyi Biotec), CD28 PECy7 (BD Biosciences), KLRG1 PE (Miltenyi Biotec) and PD1 PECy7 (eBioscience), and analyzed by FACS. Doublet exclusion for lymphocytes was achieved by gating on forward scatter (FSC) vs side scatter (SSC) followed by FSC (height) versus FSC (area).

6.2.5. Functional Characterization of Antigen-Specific T Cells

Functional activity of T cells was evaluated after short secondary stimulation using several parameters including secretion of intracellular cytokines (IFN-γ and TNF-α), activation marker expression (CD137), and cytotoxicity (CD107a) by intracellular fluorescence staining. All antibodies were purchased from BD bioscience. Irradiated autologous B-lymphoblastoid cell line cells (BLCL cells) loaded with NLVPMVATV (SEQ ID NO:1) peptide were co-incubated with T cells in an effector to target ratio of 1:5 for 16 hours in the presence of 1 μg/ml brefeldin A (Sigma-Aldrich). Co-cultured T cells were then labeled with anti-CD3 APC and anti CD8 PE for 15 mins at room temp, washed and then permeabilized with Perm solution (BD Biosciences) and then co-incubated with anti-IFN-γ PECy7 (BD Biosciences) and anti-TNF-α APC (Miltenyi Biotec), or anti-CD137 PE (BD Biosciences), or anti-CD107a FITC (BD Biosciences).

6.2.6. Analysis of T Cell Proliferation and Apoptosis

EdU labeling (ThermoFisher) was used to evaluate T cell proliferation. 10 μM EdU was added to the culture media for 1 h at 37° C. Labeled cells were washed with PBS and resuspended in T cell culture media. T cells were then analyzed by flow cytometry, and the proportion of proliferating T cells was determined by the percentage of EdU$^+$ gated T cells using the FlowJo software (Treestar). Apoptotic T cells were defined by Annexin V staining (BD Biosciences).

6.2.7. TCR Next-Generation Sequencing

T cell receptor Vβ (TCRVβ) chain hypervariable complementarity-determining region 3 (CDR3) was amplified and sequenced from DNA extracted from NLV-Tet$^+$ T cell subsets ($T_N$, $T_{SCM}$, $T_{CM}$, and $T_{EM}$) isolated by fluorescence-activated cell sorting (FACS) (purity >95%) or NLV-Tet$^+$ T cells derived from these subsets, from days 0, 15 or 30 post-stimulation using the immunoSEQ platform at Adaptive Biotechnologies. Rearranged CDR3 sequences were classified as nonproductive if they included insertions or deletions resulting in frameshift or premature stop codons, and were excluded from subsequent analyses, according to the immunoSEQ validated algorithm. TCR clonality and sample overlap were determined using the immunoSEQ Analyzer 2.0. within a range of 0 to 1, where a low number indicates higher diversity, while a high number indicates higher clonality within the sample. Sample overlap indicates the percent of similar clones within a pair of sample types.

6.2.8. Statistical Analysis

Statistical analyses were performed using Prism (GraphPad Software). For most of the comparisons a nonparametric Mann-Whitney test was used to compare two groups. One-way ANOVA was used to compare three or more groups. Significance of differences between two groups was calculated using the t-test (α=0.05). For all comparisons, two-sided P values were used; where indicated, *P<0.05; P<0.01; *P<0.005.

6.3. Results 6.3.1. Detection and Isolation of CMVpp65-Specific $T_{SCM}$ Cells within PBMCs from Healthy Seropositive Donors Gattinoni et al. (2011, Nat Med 17:1290-1297), first described $T_{SCM}$ cells within human PBMCs as a specific subset of memory T cells with high proliferative potential that when modified to express a tumor-specific chimeric antigen receptor, also exhibits superior functional activity. This example described herein was designed to test whether in vivo primed virus-specific human $T_{SCM}$ cells also exhibit these attributes. T cells were isolated from PBMCs of 12 healthy HLA A0201$^+$ CMV seropositive donors. In each of these CMV-seropositive donors, $T_{SCM}$ population was identified as CD3$^+$CD45RO$^-$CD62L$^+$CD95$^+$ cells, $T_N$ population as CD3$^+$CD45RO$^-$CD62L$^+$CD95$^-$ cells, and $T_{CM}$ and $T_{EM}$ populations as CD3$^+$CD45RO$^+$CD62L$^+$ and CD3$^+$CD45RO$^+$CD62L$^-$ cells respectively (FIG. 1). The proportion of $T_{SCM}$ cells ranged from 1.2%-10.8% within the T cell populations in the peripheral blood in the absence of any in vitro stimulation. Despite low proportions within the PBMCs, the $T_{SCM}$ cells could consistently be identified in all donors tested (n=12). In comparison, the proportion of $T_N$, $T_{CM}$ and $T_{EM}$ cells were 3.8%-28.9%, 1.7%-32.4% and 15.4%-34.9% respectively (Table 1).

TABLE 1

Percentage of naive and memory $T_N$, $T_{SCM}$, $T_{CM}$ and $T_{EM}$ CD8$^+$ T cells in healthy CMV seropositive individuals

| | Within T cell population | | | | | Within NLV-Tet$^+$ population | | | |
|---|---|---|---|---|---|---|---|---|---|
| Donor | $T_{EM}$ | $T_{CM}$ | $T_{SCM}$ | $T_N$ | Tet$^+$ | $T_{EM}$ | $T_{CM}$ | $T_{SCM}$ | $T_N$ |
| 1 | 31.9 | 8.7 | 4.2 | 8.7 | 2.5 | 35.4 | 1.1 | 0.6 | ND |
| 2 | 31.7 | 7.0 | 2.5 | 28.9 | 4.4 | 15.1 | 0.9 | 2.0 | 0.2 |
| 3 | 27.4 | 20.3 | 5.8 | 16.0 | 0.9 | 47.9 | 8.3 | 3.7 | ND |
| 4 | 22.2 | 13.8 | 3.8 | 22.0 | 0.4 | 59.7 | 9.7 | 2.4 | ND |
| 5 | 34.9 | 11.0 | 2.1 | 5.0 | 0.5 | 42.0 | 1.4 | 1.4 | ND |
| 6 | 33.0 | 12.8 | 3.1 | 6.0 | 0.3 | 79.7 | 3.4 | 1.7 | ND |
| 7 | 18.1 | 32.4 | 1.2 | 17.3 | 2.0 | 60.2 | 31.0 | 6.3 | ND |
| 8 | 21.0 | 13.0 | 1.9 | 28.6 | 0.1 | 41.7 | 2.1 | 8.3 | ND |
| 9 | 28.4 | 8.3 | 10.8 | 23.5 | 1.5 | 70.6 | 5.9 | ND | ND |
| 10 | 15.4 | 3.6 | 2.6 | 21.8 | NA | | | | |
| 11 | 25.6 | 1.7 | 2.0 | 6.5 | 1.0 | 27.8 | 3.5 | 3.0 | 0.1 |
| 12 | 28.9 | 3.5 | 2.4 | 3.8 | 0.3 | 35.8 | 5.3 | 2.0 | ND |

(ND = not detectable; NA = not applicable)

Using CMVpp65 as a model antigen, the memory phenotype of the antigen-specific T cells was then examined. Accordingly, the CMVpp65-specific T cell populations in the blood of 11 of 12 donors were evaluated. In each of the donors tested, a discrete population of antigen-specific T cells could be identified using HLA peptide tetramers that were responsive to the well known CMVpp65 epitope NLVPMVATV (SEQ ID NO:1) presented by HLA-A0201. Further analysis of these tetramer positive T cells demonstrated that the majority of memory T cells in peripheral blood that recognize NLV epitope bear either a $T_{CM}$ or $T_{EM}$ phenotype (0.9%-31% and 15.1%-70.6% respectively) and the remainder were effector T cells (Table 1). Then it was determined whether there was a population of $T_{SCM}$ cells circulating in the peripheral blood of healthy donors that were also antigen-specific. Of the 11 donors total, 10 had a distinct population of $T_{SCM}$ cells within the CD95$^+$ naive T cell precursors (CD45RO$^-$CD62L$^+$), that could bind to the A2-NLV tetramer (0.6%-8.3%) (Table 1).

Other studies have demonstrated the feasibility of generating CMV specific T cells from cord blood donors from the naive T cell compartment (Hanley et al., 2015, Sci Transl Med 7:285ra263; Szabolcs, 2011, Immunol Res 49:56-69). Therefore the proportion of NLV-Tet$^+$ T cells within the CD95 negative naive T cells was examined. However, $T_N$ cells within the NLV-Tet$^+$ population in the peripheral blood could only be detected in 2 of 11 donors. Taken together, the data suggest that a minor proportion of NLV-tetramer binding CD8$^+$ T cells are within the CD45RO$^-$CD62L$^+$ compartment and they consist of both the CD95$^+$ $T_{SCM}$ and CD95$^-$ $T_N$ cells.

6.3.2. Epitope Specific $T_{SCM}$ Cells can be Successfully Expanded In Vitro and Maintain a Less Differentiated Memory Phenotype During Antigen-Specific Stimulation Next, it was evaluated which of the memory T cell populations detected in these healthy latently unrelated seropositive donors served as the reservoir of T cell immunity from which antigen-specific T cells were generated upon secondary challenge. It was particularly desirable to comparatively assess the potential of CMV-specific $T_{SCM}$ cells to expand and act as a durable T cell reservoir. For these studies, an in vitro system was developed for expansion of CMVpp65 specific T cells from all memory T cell compartments from human PBMCs. $T_{SCM}$, $T_N$, $T_{CM}$ and $T_{EM}$ cell populations were FACS sorted from HLA-A*0201 CMV-seropositive donors as described above using the expression markers CD62L, CD45RO and CD95. Then the sorted T cell subsets were sensitized with artificial antigen presenting cells (AAPCs) exclusively expressing HLA-A*0201, CMVpp65 and T cell costimulatory molecules as previously described (Hasan et al., 2009, J Immunol 183:2837-2850). Then this approach was modified to include supplementation of the cultures with IL-7 and IL-15 every 2 days beginning at day 4 as previously described (Cieri et al., 2013, Blood 121:573-584).

Figure 2A:
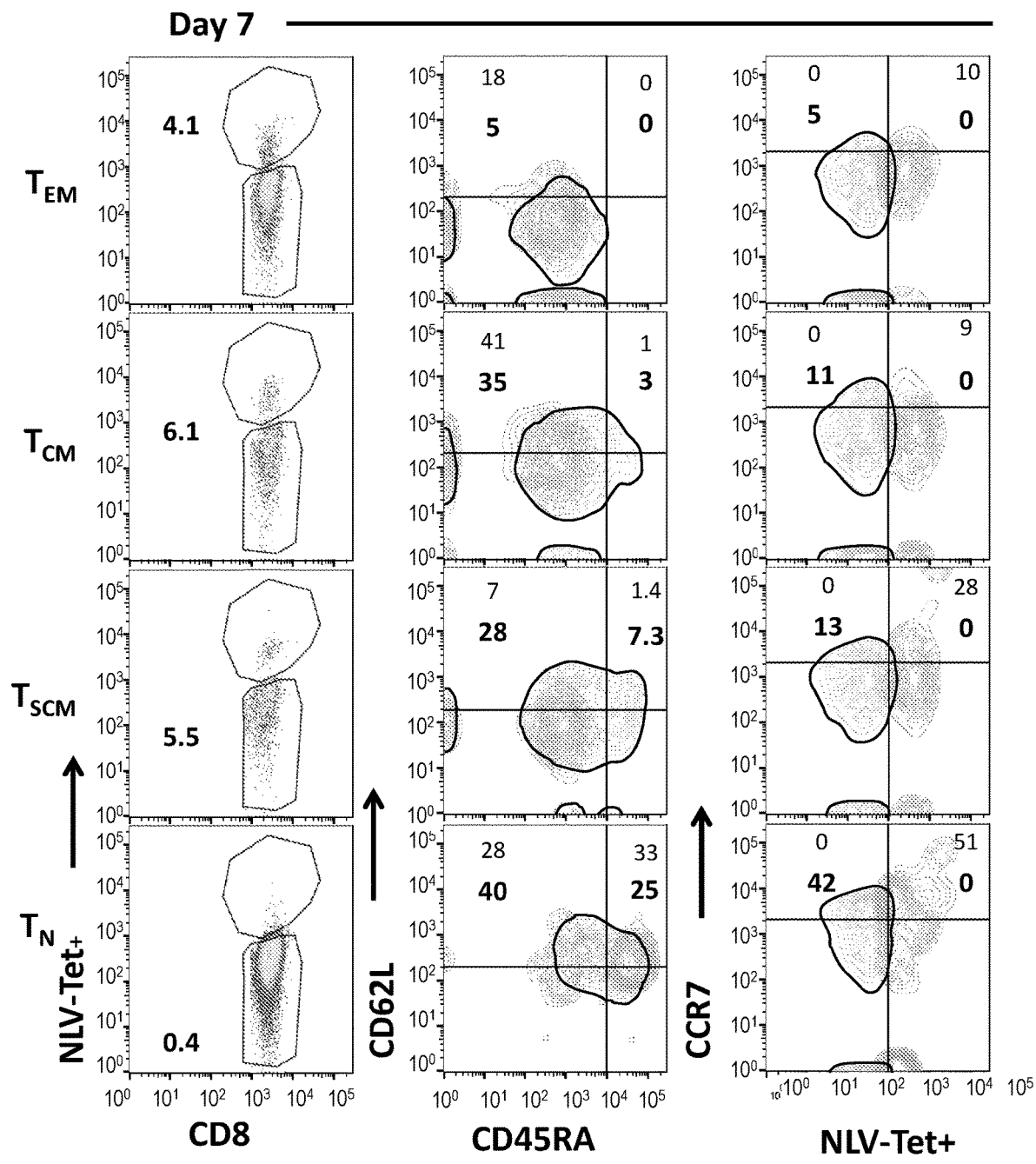
Figure 2B:
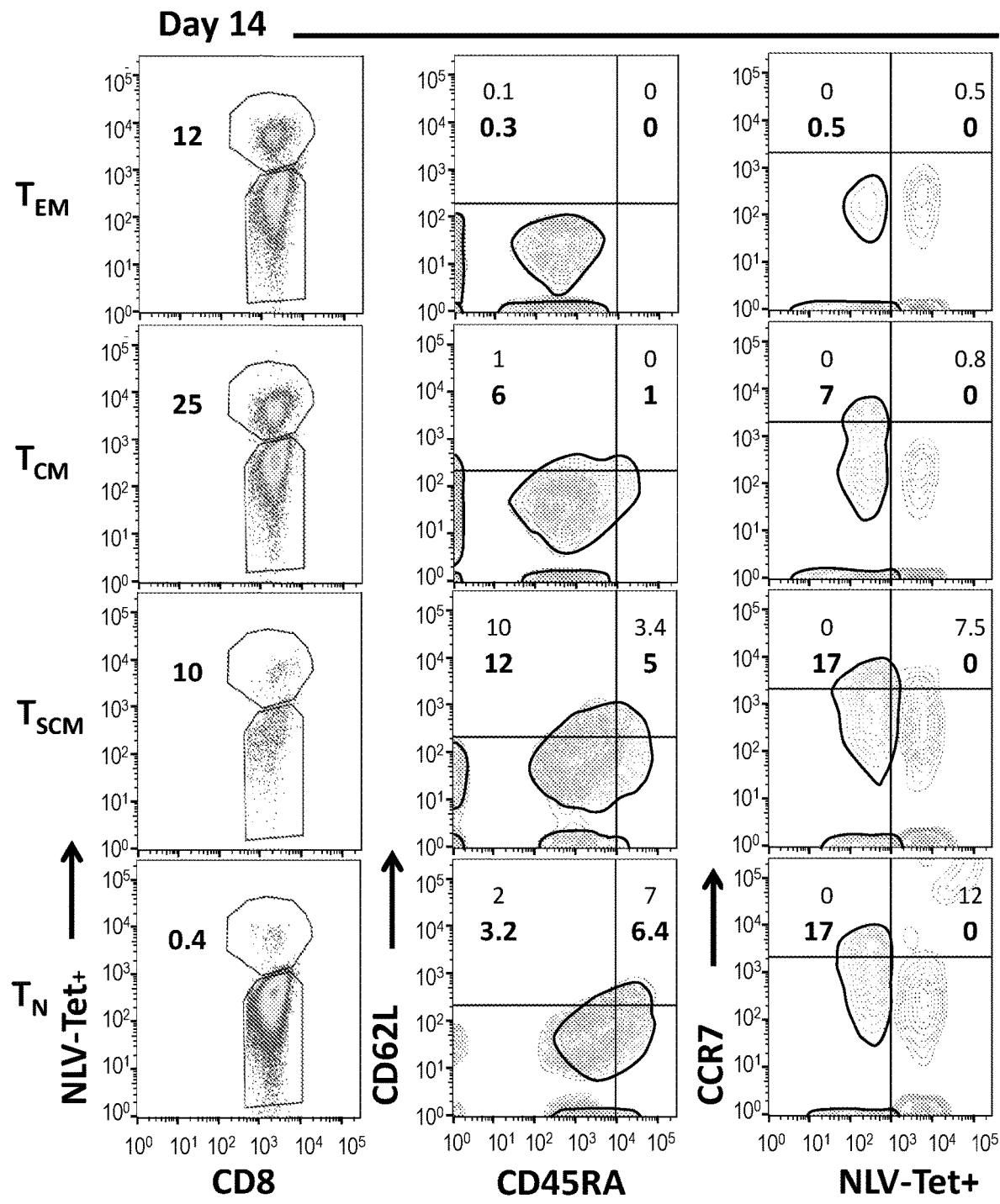
Figure 2C:
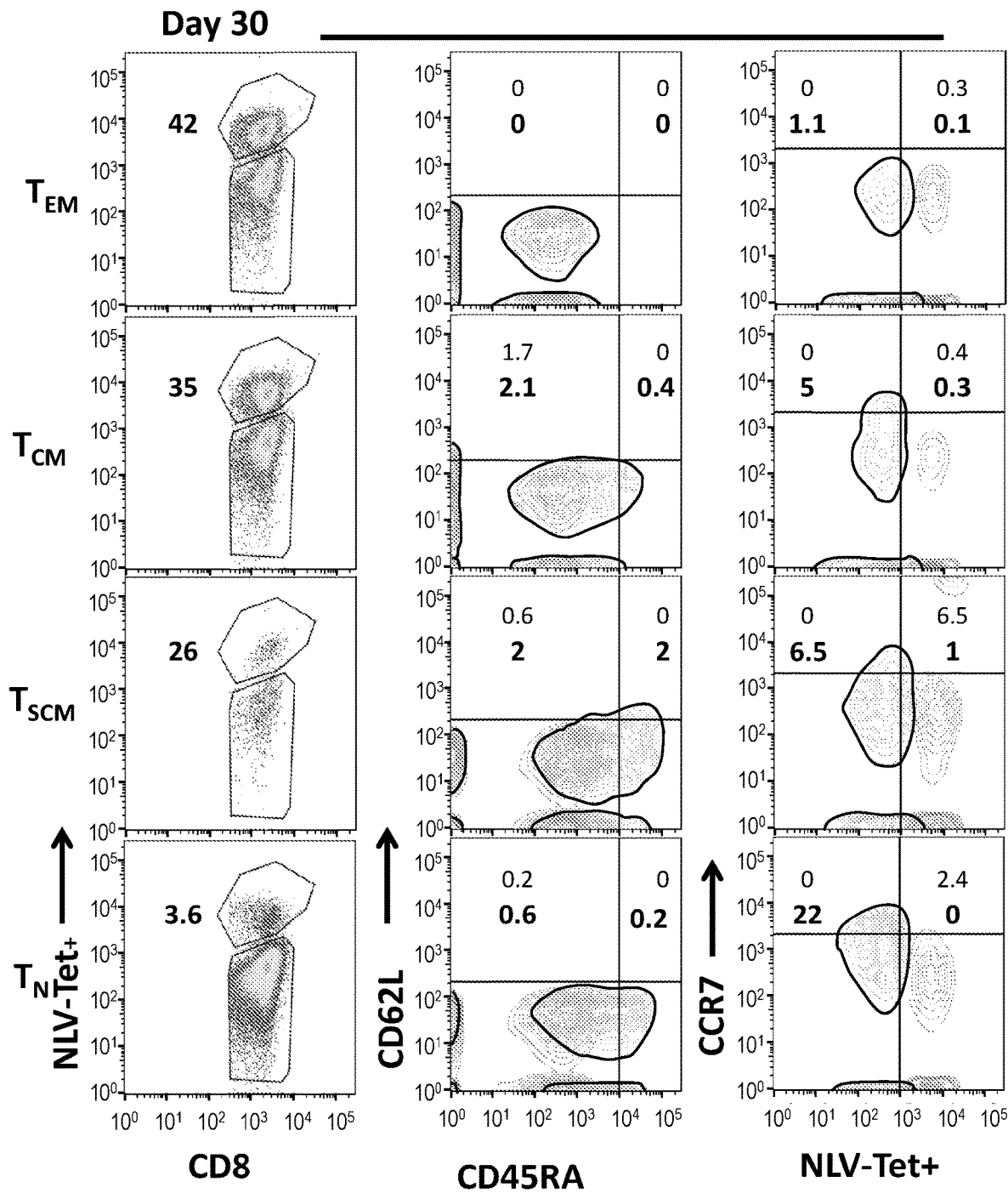
Figures 2D, 2E:
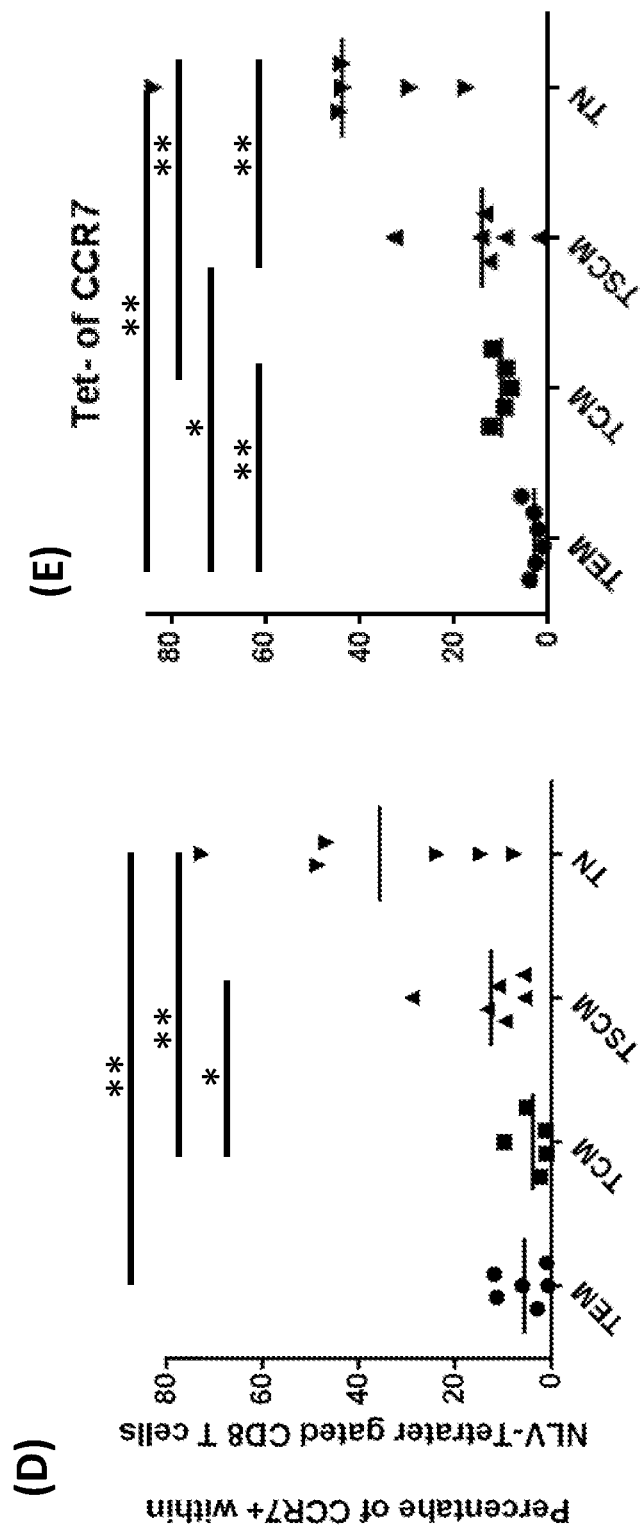

Using this method for in vitro sensitization of $T_{SCM}$ cells, HLA-A*0201 NLV-tetramer$^+$ CD8$^+$ T cells could be enriched up to 5.5% by 7 days from 0.6% at day 0 as shown for one representative donor (FIG. 2A). A similar enrichment of HLA-A*0201 NLV-tetramer$^+$ T cells was also observed within the $T_{CM}$- and $T_{EM}$-derived CD8$^+$ T cells (6.1% and 4.1% respectively) (FIG. 2A). Over a period of 4 weeks after antigen-specific in vitro sensitization, $T_{SCM}$ derived cells gradually acquired $T_{CM}$ and $T_{EM}$ phenotype within both the NLV-Tet$^+$ as well as NLV-Tet$^-$ T cell populations (FIGS. 2B and 2C). Strikingly, within the NLV-Tet$^+$ T cells derived from the $T_{SCM}$ subset, a proportion of cells with a CD45RA$^+$ and CD62L$^+$ $T_{SCM}$ phenotype could be detected for up to 14 days in culture. By this time, both $T_{CM}$- and $T_{EM}$-derived cells had converted to $T_{EM}$ phenotype (FIG. 2B). Higher CCR7 expression was also detected within both the NLV-Tet$^+$ as well as NLV-Tet$^+$ T cells derived from $T_{SCM}$ cells after 14 days of antigen-specific stimulation in comparison to $T_{CM}$- and $T_{EM}$-derived cells (FIGS. 2D and 2E). CCR7 was expressed in 7.5% of $T_{SCM}$-derived NLV-Tet$^+$ T cells (FIG. 2D). These data suggest that the $T_{SCM}$ cells follow a differentiation trajectory progressing to $T_{CM}$, and then $T_{EM}$ cells during in vitro expansion. These results also suggest that $T_{SCM}$-derived cells have the ability to maintain a less differentiated phenotype than $T_{CM}$-derived cells.

Using the same approach, CMV-specific T cells derived from CD95$^-$ $T_N$ cells also were generated. Regardless of the detection of NLV-Tet$^+$ T cells in the sorted $T_N$ cells within the peripheral blood before antigen stimulation, NLV-Tet$^+$ T cells could be generated from 6 of 6 different donors by this method of sensitization from sorted $T_N$ cells. Upon stimulation, $T_N$ cells upregulated the CD95 expression within 2 days and converted to a $T_{SCM}$ phenotype. $T_N$ cells also maintained a less differentiated memory phenotype, with expression of CD62L and CCR7 within a proportion of NLV-Tet$^+$ T cells for a longer duration during antigenic stimulation than the $T_{CM}$- and $T_{EM}$-derived cells. In a representative example (FIG. 2D), $T_N$-derived cells demonstrated CCR7 expression in 12% of NLV-Tet$^+$ T cells after 14 days of continuous antigenic stimulation, in comparison to 7.5%, 0.8% and 0.5% CCR7 expressing NLV-Tet$^+$ T cells derived from $T_{SCM}$, $T_{CM}$ and $T_{EM}$ subsets respectively. Within a total of 6 donors tested, the differential expression of CCR7 in $T_N$-derived NLV-Tet$^+$ T cells was significantly higher than that observed in $T_{CM}$- and $T_{EM}$-derived NLV-Tet$^+$ T cells (p<0.01) (FIG. 2D). These studies demonstrate a less differentiated phenotype within antigen-experienced T cells derived from $T_N$ and $T_{SCM}$ cells. However, the enrichment of NLV-Tet$^+$ populations was less pronounced within the $T_N$-derived cells (0.4%, 0.4% and 3.6% at Day 7, 14 and 30 as shown in FIGS. 2A, 2B and 2C) than within T cells derived from the memory T cell populations ($T_{SCM}$, $T_{CM}$ and $T_{EM}$ cells). The slow enrichment of CMV-specific cells might result from the extremely low precursor frequencies in the $T_N$ subset in the peripheral blood.

6.3.3. Characterization of the Co-Stimulatory and Senescence Markers within Memory T Cell Populations Next, other characteristics within the naive and different memory T cell subsets were evaluated, to identify a particular subset with higher potential for proliferation and persistence. The expression of a panel of markers was evaluated, including the co-stimulatory markers CD27 and CD28 as well as IL-7Rα (CD127), the activation marker PD-1 and the senescence marker CD57. The expression of each of these markers was compared in cells that recognize the same antigen to rule out differences occurring as a result of differential enrichment of antigen-specific T cells within each subset.

Figure 3A:
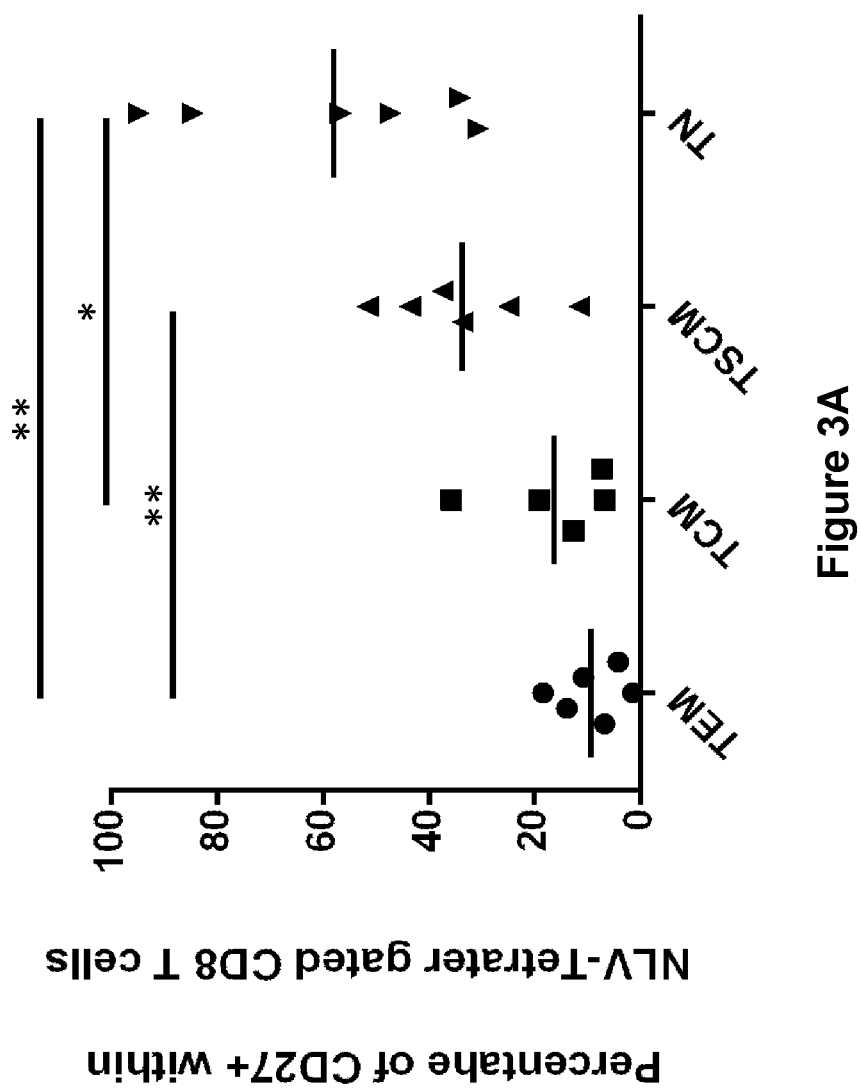
Figure 3B:
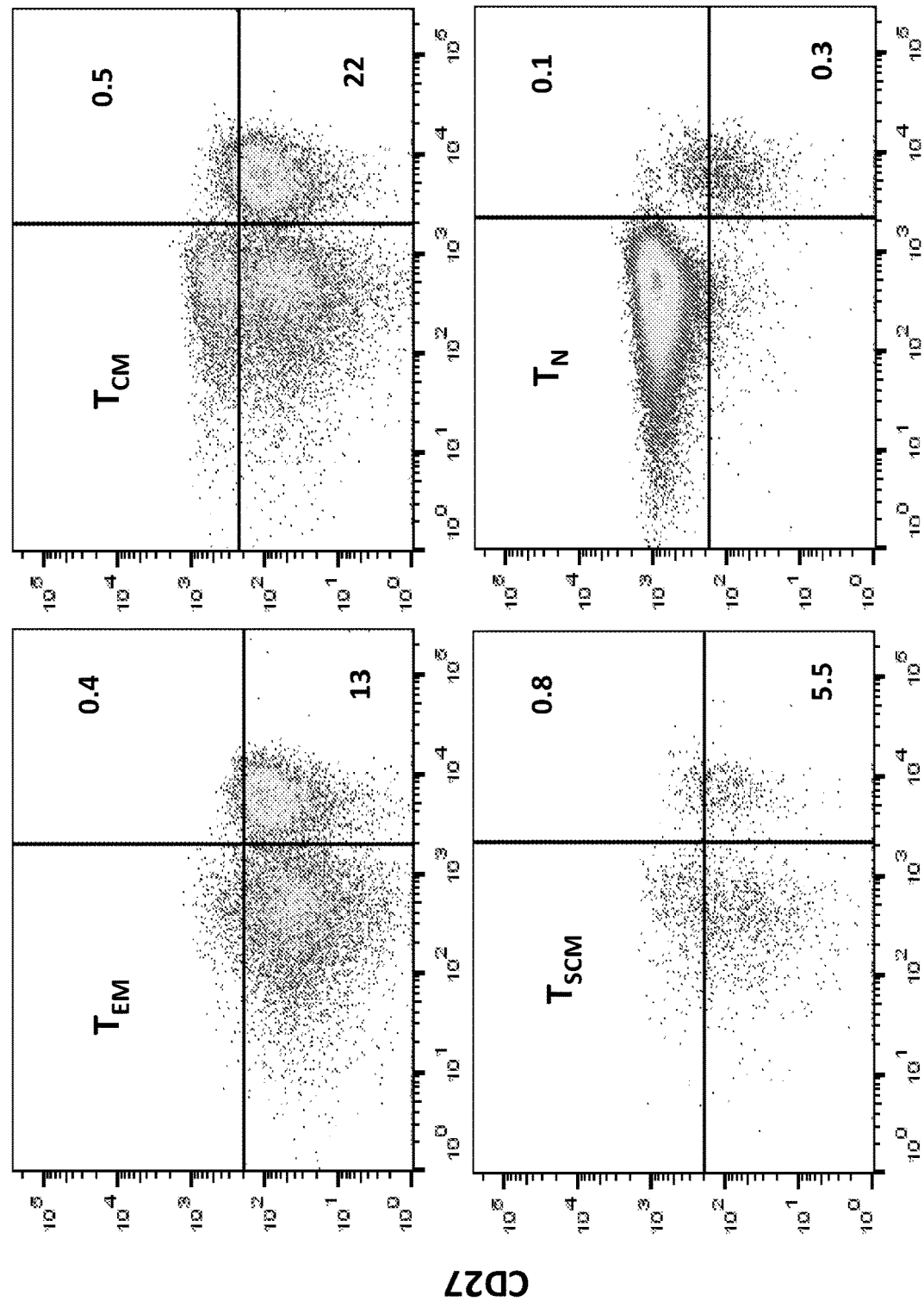

CD27 is constitutively expressed as a co-stimulatory molecule on naive and memory T cells. Its expression increases upon T cell activation, and is lost at the fully differentiated effector phase (Hintzen et al., 1993, J Immunol 151:2426-2435). Consistent with its role in T cell activation and proliferation, a recent study also demonstrated that CD27 co-stimulation improves the function of chimeric antigen receptor (CAR) modified T cells (Song et al., 2012, Blood 119:696-706). In the example herein, upon antigen stimulation, a significantly higher proportion of cells expressing CD27 was found, within NLV-Tet$^+$ T cells derived from $T_N$ cells compared to those derived from $T_{CM}$ and $T_{EM}$ cells, respectively, and within NLV-Tet$^+$ T cells derived from $T_{SCM}$ cells compared to those derived from $T_{EM}$ cells, in 6 donors tested (**p≤0.005 and *p≤0.05) (FIG. 3A). In the representative example shown (FIG. 3B), high expression of CD27 is also demonstrated in almost all of the NLV-Tet$^-$ CD8$^+$ T cells derived from $T_N$ cells (FIG. 3B).

Figure 3C:
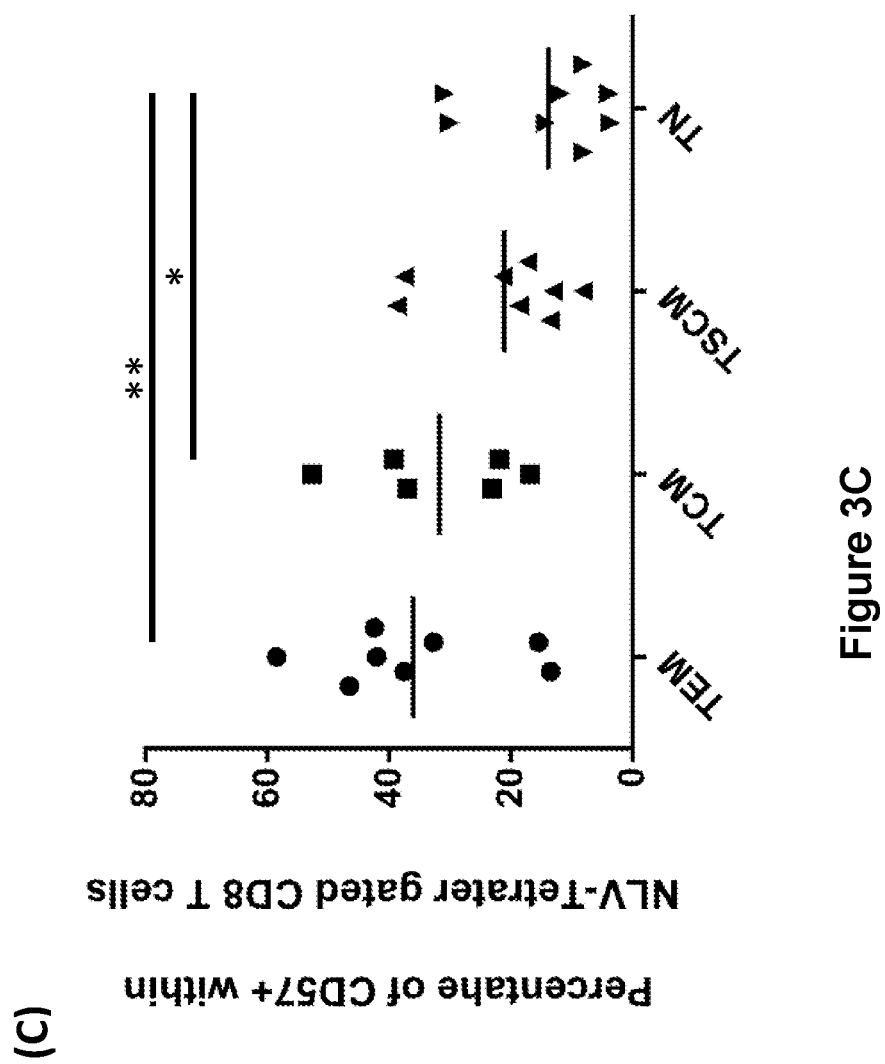
Figure 3D:
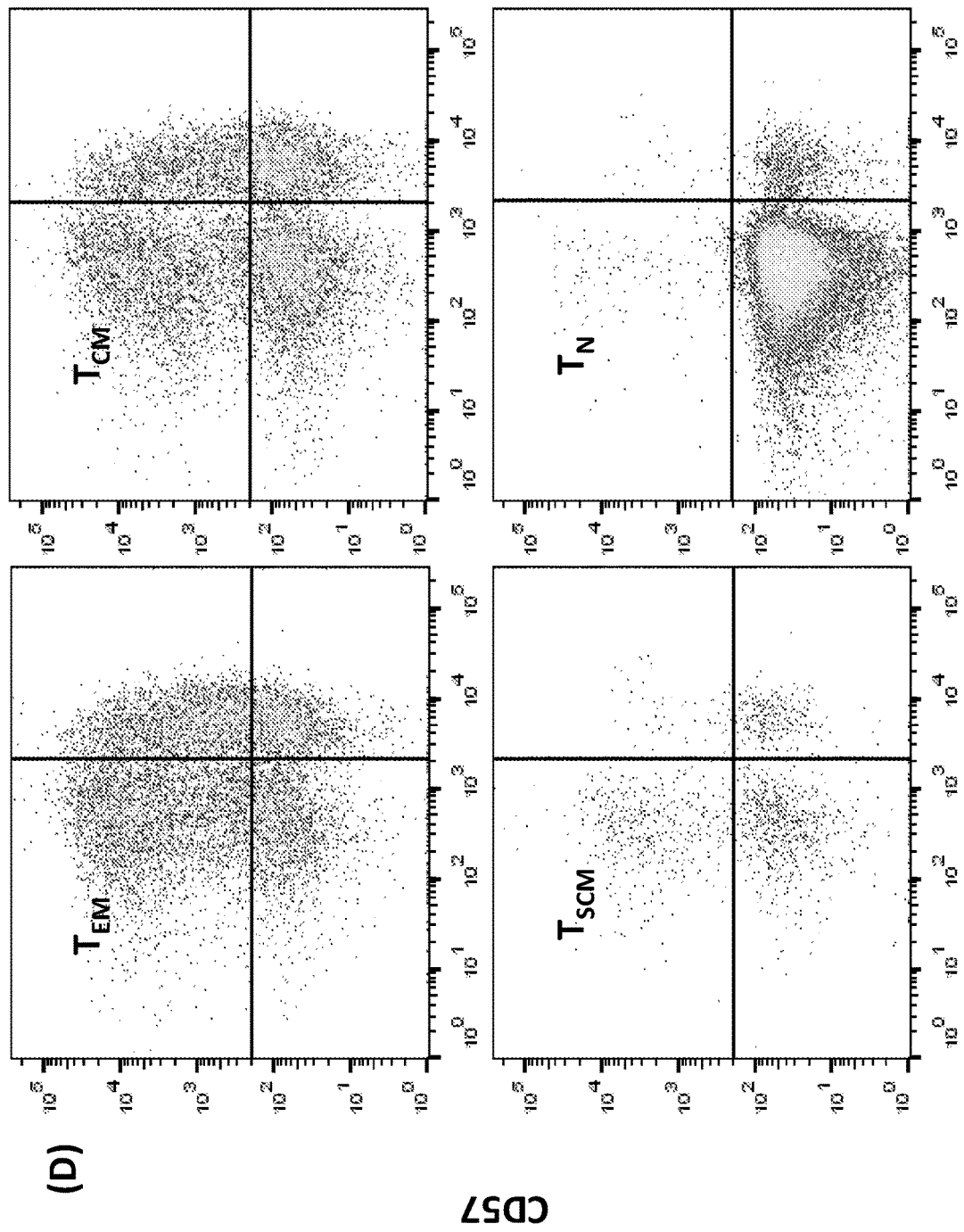

Then the expression of CD57, which has been described to be indicative of replicative senescence and antigen-induced apoptosis in HIV-specific CD8$^+$ T cells (Brenchley et al., 2003, Blood 101:2711-2720), was evaluated. After antigen-specific stimulation, a significantly lower proportion of CD57 expressing cells was found within $T_N$-derived NLV-Tet$^+$ T cells, compared to $T_{CM}$- and $T_{EM}$-derived NLV-Tet$^+$ T cells as shown for 6 donors tested (**p≤0.005 and *p≤0.05) (FIGS. 3C and 3D). $T_{SCM}$-derived cells expressed lower levels of CD57 than $T_{CM}$- and $T_{EM}$-derived cells, though this difference was not statistically significant for the donors tested. Nonetheless, this data demonstrate a trend towards increasing levels of CD57 expression with increasing T cell differentiation ($T_N < T_{SCM} < T_{CM} < T_{EM}$).

Figures 3E, 3F, 3G, 3H:
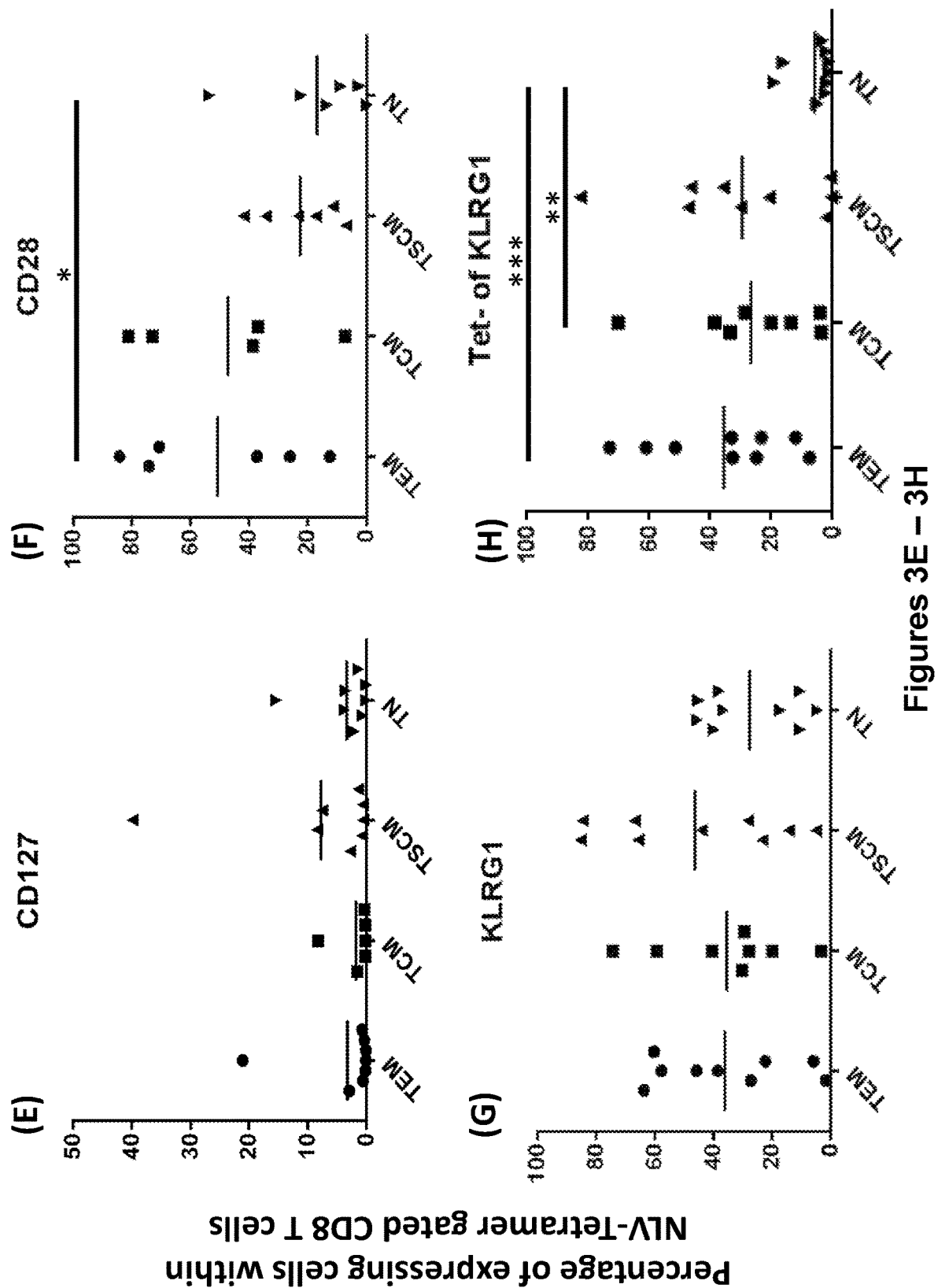
Figures 3I, 3J:
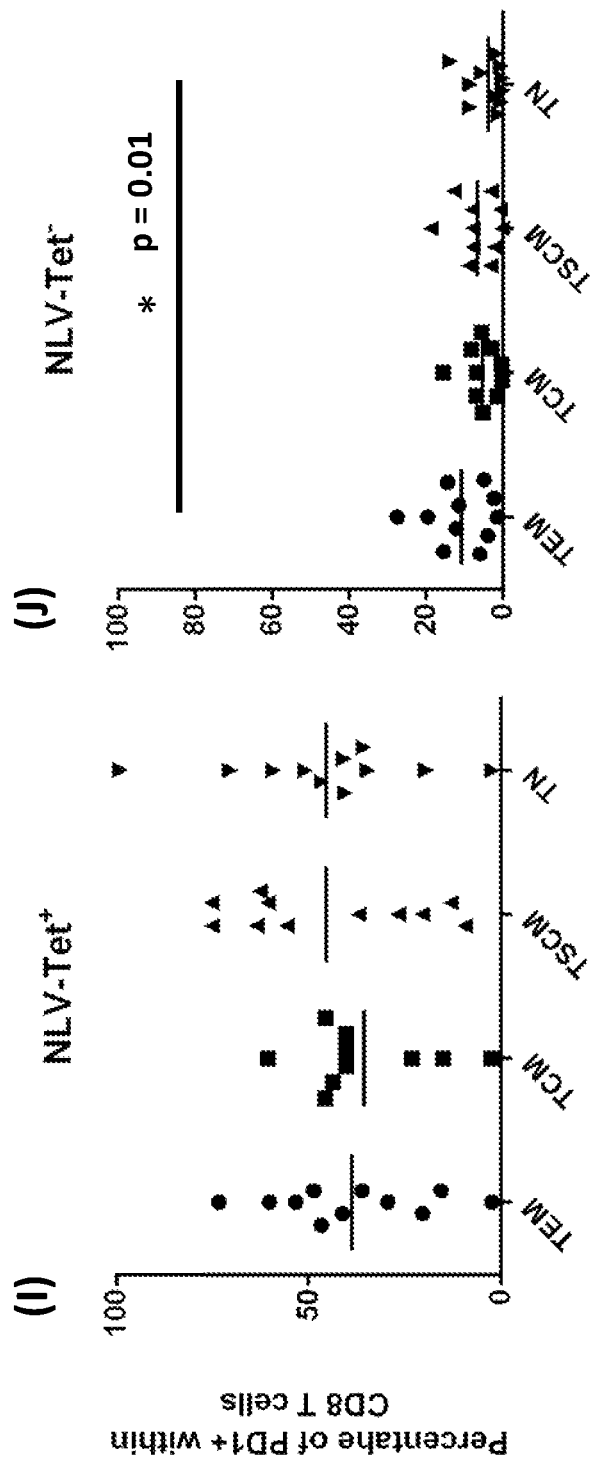

Next, the expression of IL-7Rα (CD127), which has been shown to facilitate T cell engraftment and persistence in mouse models (Kaech et al., 2003, Nat Immunol 4:1191-1198), was examined. In the example herein, a slightly higher level of CD127 expression was observed within $T_{SCM}$-derived NLV-Tet$^+$ T cells compared to $T_{CM}$- and $T_{EM}$-derived T cells though this was not statistically significant ($T_{SCM}$ vs $T_{EM}$ p=0.11 and $T_{SCM}$ vs $T_{CM}$ p=0.03) (FIG. 3E). In contrast, moderate to high levels of CD28 expression were observed within NLV-Tet$^+$ T cells derived from all subsets, suggesting adequate activation and co-stimulatory capacity within these activated antigen-specific T cells (FIG. 3F). After antigenic stimulation, variable levels of PD-1 expression were detected within the NLV-Tet$^+$ T cells derived from all T cell subsets tested, with no apparent trend (FIG. 3I). However, the expression of PD-1 within NLV-Tet$^-$ CD8$^+$ T cells was lower than the NLV-Tet$^+$ counterparts (FIG. 3J). The expression of PD-1 in these T cells is possibly indicative of an activated state. High levels of KLRG-1 expression were also detected within the NLV-Tet$^+$ T cells derived from all T cell subsets tested, suggesting the late differentiation stage in antigen-experienced cells (FIG. 3G). In contrast, expression of KLRG1 in the $T_N$-derived NLV-Tet$^-$ T cells was significantly lower than that expressed in $T_{CM}$- and $T_{EM}$-derived NLV-Tet$^-$ T cells, respectively (FIG. 3H). Taken together, these data suggest that antigen-experienced cells derived from the $T_{SCM}$ memory subset demonstrate a phenotype with CD27$^{hi}$, CD57$^{low}$ and CD127$^{int}$, which is not observed in $T_{CM}$- and $T_{EM}$-derived antigen-specific T cells.

Figure 4A:
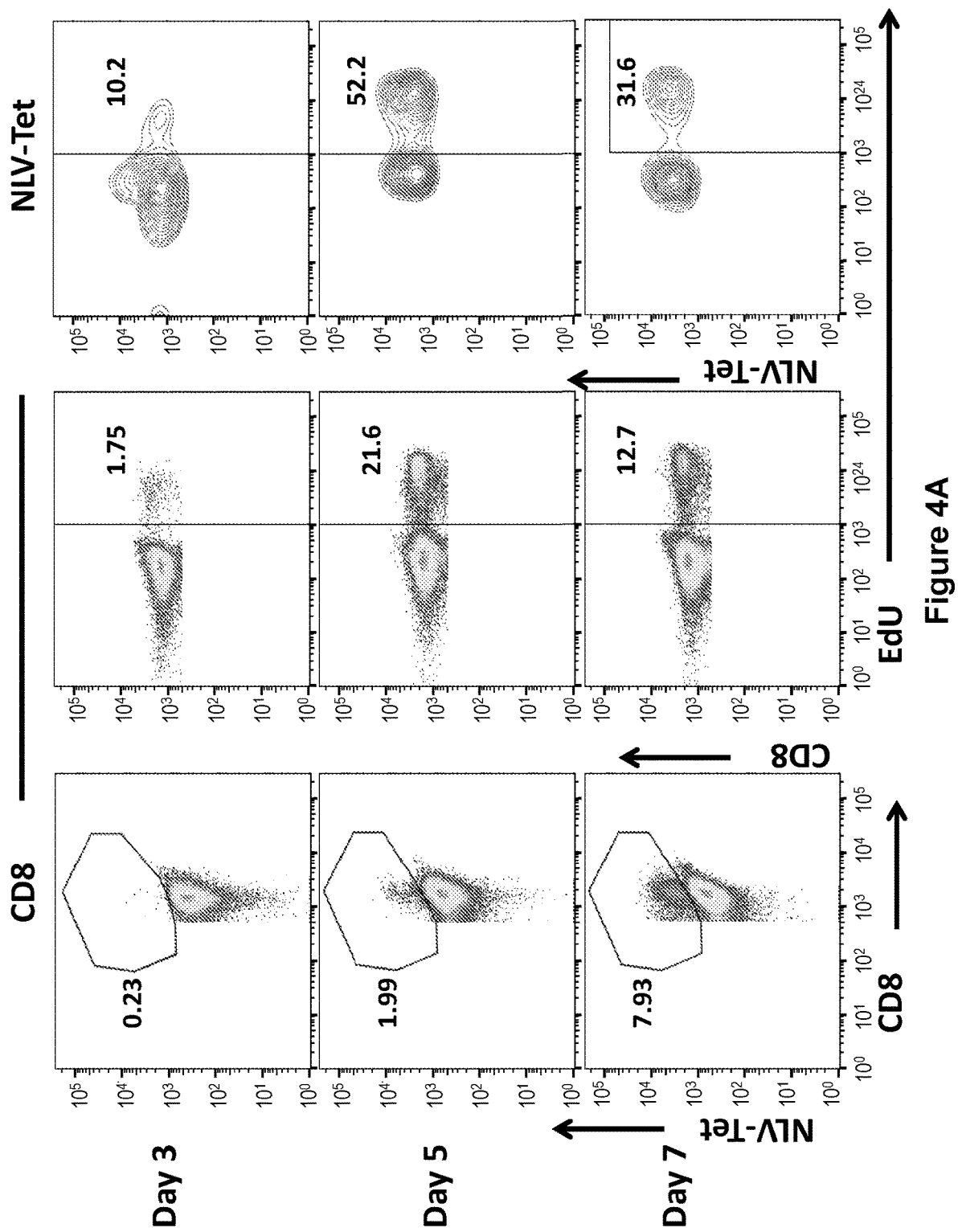
Figure 4B:
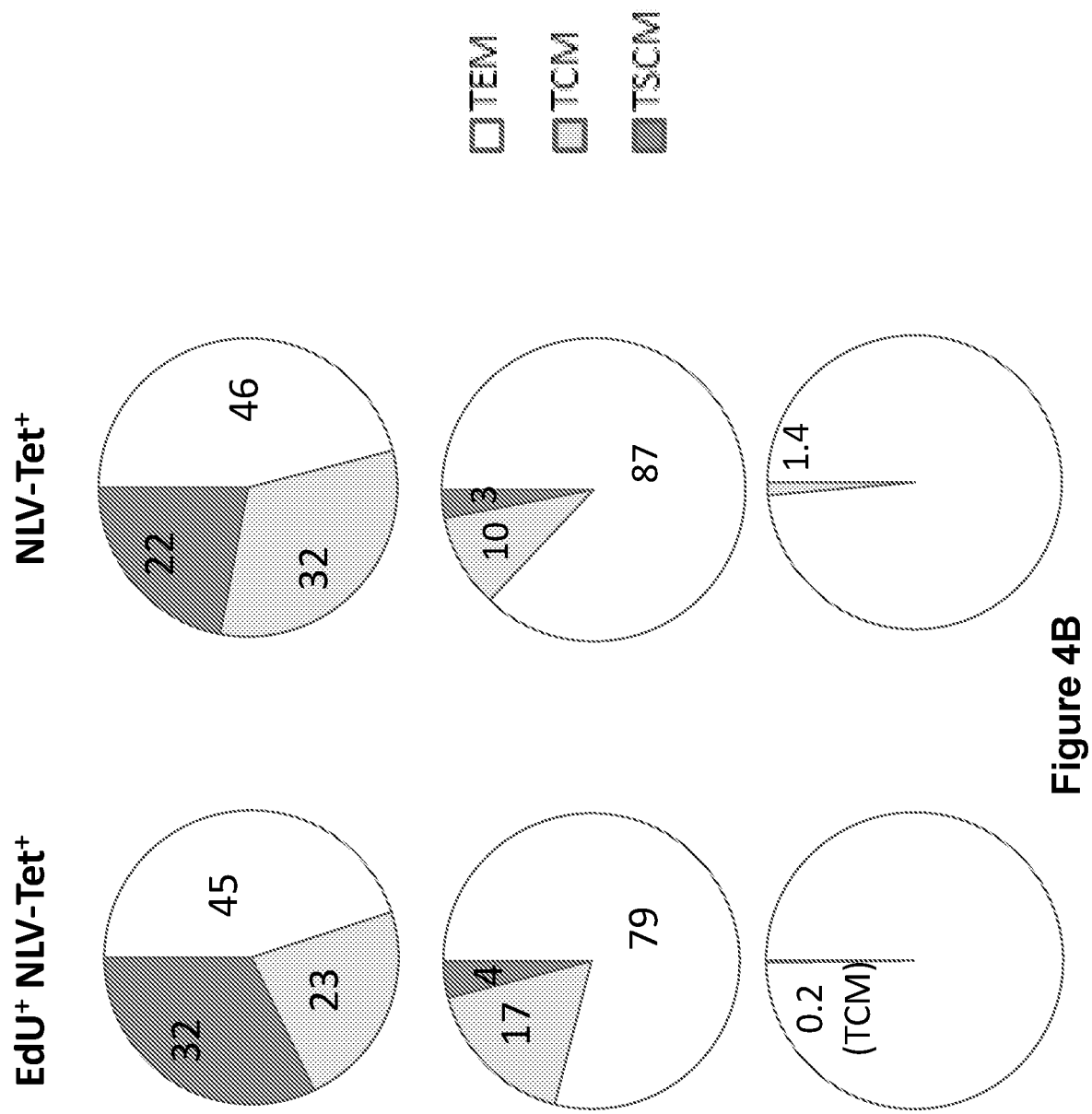
Figure 4C:
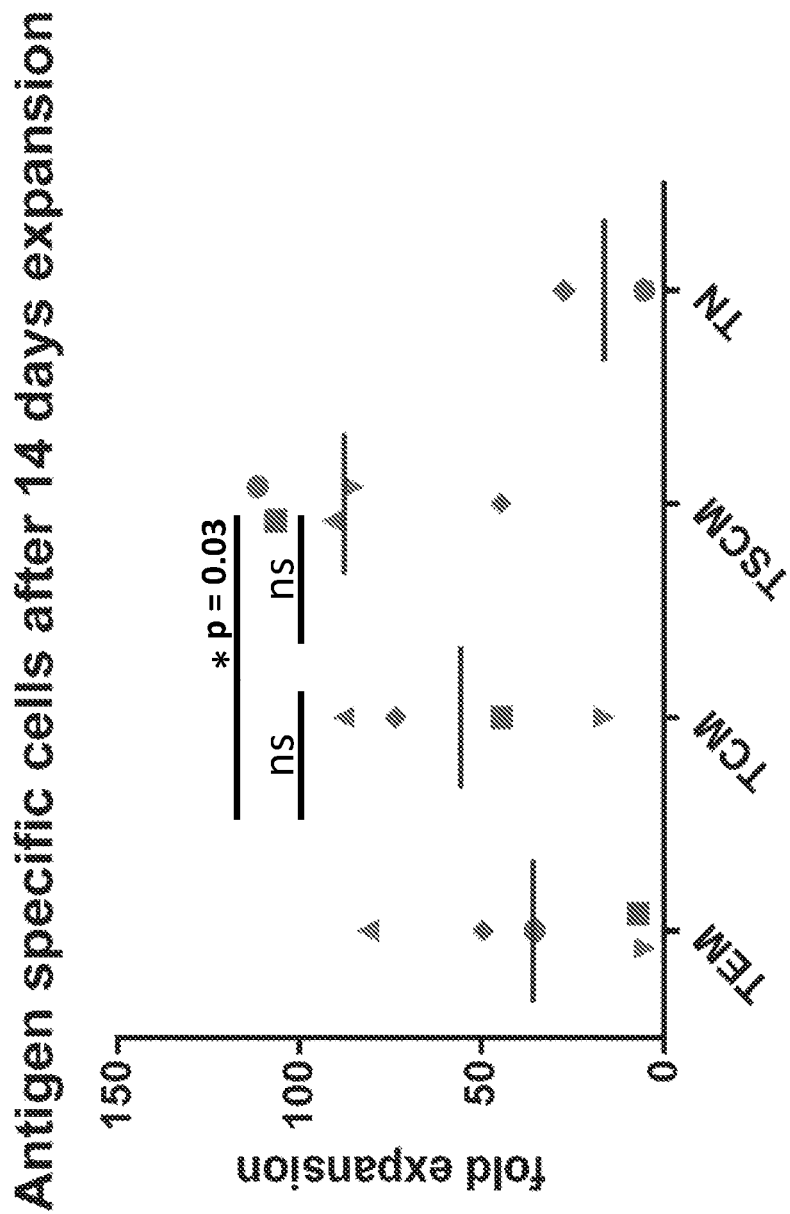

6.3.4. $T_{SCM}$-Derived T Cells Demonstrate Higher Proliferative Capacity Leading to Superior Expansion of Antigen-Specific T Cells The data above show that $T_{SCM}$ cells maintain a less differentiated memory phenotype during antigen-specific activation, and a higher level of CD27 expression which sustains a greater proliferative potential. These data suggest that $T_{SCM}$ cells might serve as a durable reservoir of antigen-experienced T cells for memory immune response upon antigen re-challenge. To address this, the in vitro proliferative capacity of different memory T cell subsets upon antigen-specific stimulation with AAPCs expressing CMVpp65 was evaluated, and the phenotype of proliferating T cells was examined using EdU labeling (see Section 6.2, supra). Within total T cell populations stimulated, vigorous T cell proliferation was observed starting at 3 days after stimulation. Within the NLV-Tet$^+$ T cells 10.2% proliferating cells were observed in a representative donor at day 3, reaching a peak of 52.2% at day 5 post-stimulation (FIG. 4A). The less differentiated $T_{SCM}$ and $T_{CM}$ cells constituted 32% and 23% respectively, of the proliferating memory NLV-Tet$^+$ T cells at day 3 (FIG. 4B). At this time the total NLV-Tet$^+$ T cells contained 22% of $T_{SCM}$ cells and 32% $T_{CM}$ cells (FIG. 4B). By day 5, the $T_{SCM}$ and $T_{CM}$ subsets contributed to 21% of the proliferating memory NLV-Tet$^+$ T cells, while they represented 13% of the NLV-Tet$^+$ memory T cell compartment (FIG. 4B). These data suggest that there is an early preferential proliferation within the $T_{SCM}$ and $T_{CM}$ subsets upon antigen-specific stimulation (FIG. 4B). By day 7 post-stimulation, the majority of the NLV-Tet$^+$ T cells differentiated to the $T_{EM}$ phenotype in this donor, and at this time $T_{EM}$ is the predominant subset constituting the proliferating NLV-Tet$^+$ T cells (FIG. 4B). Taken together, $T_{SCM}$ cells appear to reach their maximum proliferative capacity on days 3-5 in culture, suggesting that this is the optimal time to carry out transduction of the $T_{SCM}$ cells, if desired, particularly transduction with a vector (e.g., a retroviral vector) that requires cell proliferation for integration. To compare the proliferative potential of each memory subset, the fold expansion of NLV-Tet$^+$ T cells derived from each of these naive and memory subsets was examined. The yield of antigen-specific T cells was calculated and normalized to the number of Tet$^+$ T cells present in peripheral blood. After two rounds of antigen exposure, a significantly higher fold expansion of antigen-specific T cells was observed within $T_{SCM}$-derived cells compared to $T_{EM}$ derived cells (p=0.03) (FIG. 4C). Although the overall fold expansion of $T_{CM}$-derived NLV-Tet$^+$ T cells was lower than $T_{SCM}$-derived cells, this difference was not statistically significant. The same analysis could not be performed for some of the $T_N$ donors due to the undetectable levels of Tet$^+$ T cells in peripheral blood before antigen stimulation. Taken together, these data indicate that cells derived from the $T_{SCM}$ subset demonstrate superior expansion of antigen-specific cells and may serve as a significant source of other subsets in the T cell memory pool.

Figure 5B:
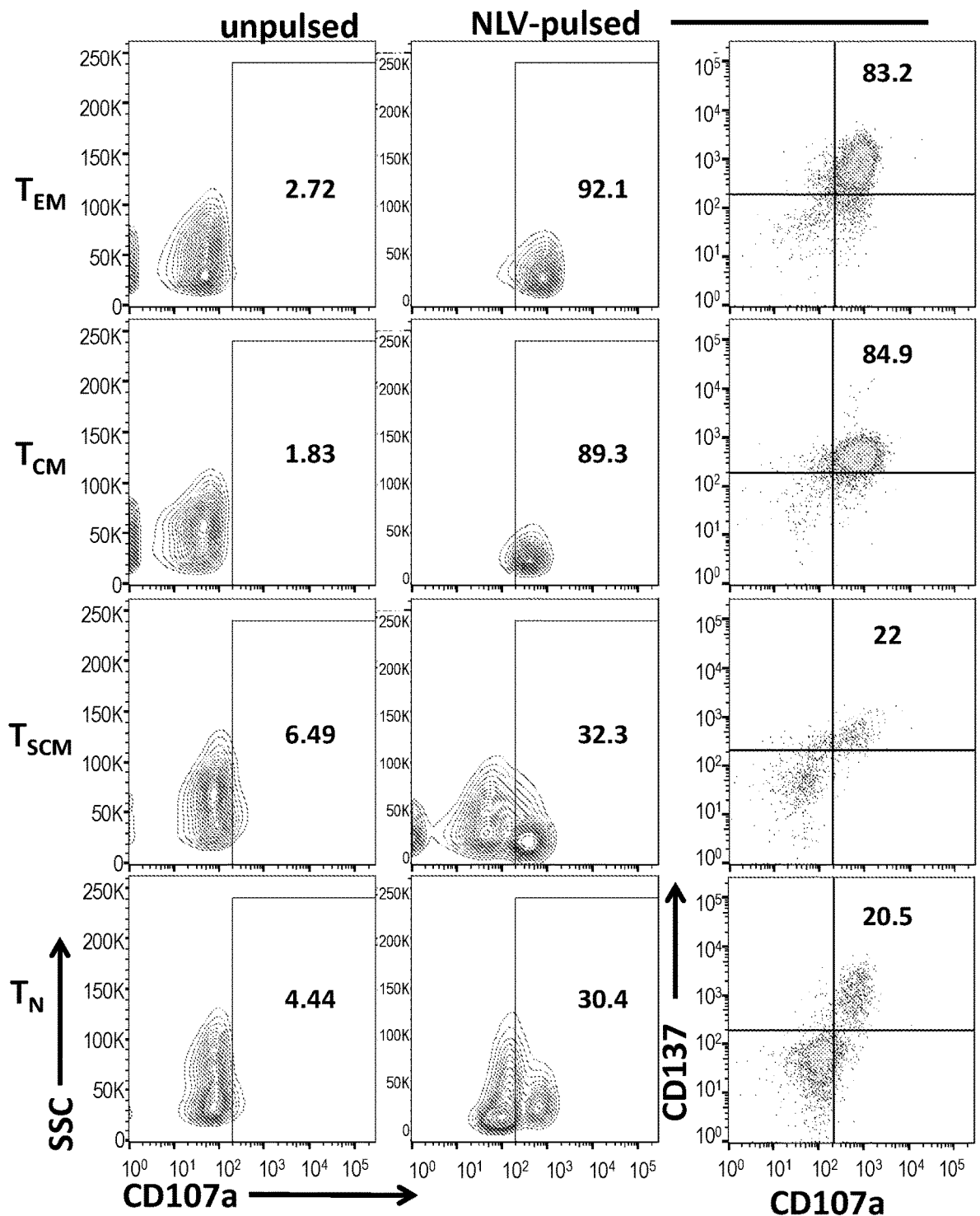

6.3.5. In Vitro Expanded $T_N$ and $T_{SCM}$-Derived T Cells Demonstrate Functional Activity Against Specific Epitopes as $T_{CM}$- and $T_{EM}$-Derived T Cells Given that the epitope specific $T_N$ and $T_{SCM}$ cells maintain a less differentiated phenotype during in vitro expansion, the question arises whether this would hamper their functional activity against antigen. Thus, the ability of cells derived from naive and memory T cell subsets to generate cytokines in response to secondary stimulation with antigen was evaluated. CD137 has been described as a marker of antigen-specific CD8$^+$ T cells that correlates with functional activity including production of cytokines TNF-α and IFN-γ, as well as cytotoxicity activity (evaluated by CD107a degranulation assay) (Wolff et al., 2007, Blood 110:201-210). Isolated in vitro expanded naive- and memory-derived T cells were secondarily stimulated by autologous NLV peptide loaded BLCLs. Following antigen-stimulation, the proportion of CD137 expressing cells within the CD8$^+$ T cells increased, as shown for a representative donor in FIG. 5A ($T_N$: 3.36%, $T_{SCM}$: 37%, $T_{CM}$: 90.4% and $T_{EM}$ 82%). T cells derived from all subsets ($T_N$, $T_{SCM}$, $T_{CM}$ and $T_{EM}$) were able to produce cytokines. Of note, T cells capable of secreting both TNF-α and IFN-γ were observed in T cells derived from all subsets including $T_N$ and $T_{SCM}$. To demonstrate cytotoxicity activity of T cells derived from different subsets, the CD107a degranulation assay was performed. Complementing their capacity to secrete cytokines, $T_N$- and $T_{SCM}$-derived cells also demonstrated functional cytotoxic activity against peptide loaded autologous targets. The percentage of CD107a-expressing cells within the $T_N$- and $T_{SCM}$-derived CD8$^+$ T cell population was 20% and 22% respectively (FIG. 5B). Taken together, epitope specific T cells can be expanded in vitro from $T_N$ and $T_{SCM}$ cells by stimulation with antigen-expressing AAPCs in the presence of IL-7 and IL-15. These epitope specific $T_N$- and $T_{SCM}$-derived cells, after expansion in vitro, demonstrate a less differentiated memory phenotype than $T_{CM}$- or $T_{EM}$-derived epitope specific T cells expanded in vitro. However, these antigen-specific $T_N$- and $T_{SCM}$-derived cells are functional as evidenced by their ability to release cytokines and degranulate in response to antigen stimulation.

6.3.6. In Vitro Expanded $T_{SCM}$-Derived CMV-Specific T Cells Exhibit an Oligoclonal Repertoire of Public TCRs that is Similar to that of $T_{CM}$- and $T_{EM}$-Derived Populations Next, the clonal diversity and/or similarity between NLV-Tet$^+$ T cells derived from naive as well as memory T cell subsets were examined. To assess clonal differences in the TCR sequences within NLV-Tet$^+$ T cells, $T_N$-, $T_{SCM}$-, $T_{CM}$- and $T_{EM}$-derived NLV-specific T cells from two CMV seropositive donors were evaluated. It was first evaluated if there were common TCR sequences within CMV-specific T cells derived from $T_N$, $T_{SCM}$, $T_{CM}$ and $T_{EM}$ cells. Accordingly, $T_N$-, $T_{SCM}$-, $T_{CM}$- and $T_{EM}$-derived T cells were expanded in vitro using artificial antigen presenting cells for 30 days, and the NLV-Tet$^+$ T cells and NLV-Tet$^-$ T cells were sorted. Then TCR repertoire analysis was performed by next-generation sequencing on the sorted Tet$^+$ T cells in comparison to the Tet$^-$ T cells. TCR sequencing data were analyzed for similarities in nucleotide sequences by sample overlap. This analysis demonstrates a high overlap between TCR sequences for $T_{CM}$- and $T_{EM}$-derived NLV-Tet$^+$ T cells post-stimulation (96% overlap in FIG. 6C). $T_{SCM}$-derived cells demonstrated high similarities with $T_N$- and $T_{CM}$- derived cells, and less similarities with $T_{EM}$-derived cells ($T_N$: 84%; $T_{CM}$: 91%; and $T_{EM}$: 57% in FIG. 6C). $T_N$-derived Tet+ cells also had a high degree of TCR similarities/overlap with Tet+ $T_{CM}$-derived cells (87%) but very little overlap with $T_{EM}$-derived cells (14%). No TCR overlap was detected within NLV-Tet− T cells derived from either naive or memory T cells (data not shown). Overall, these data indicate that Tet+ T cells recognizing the NLV epitope that are derived from the naive like $T_N$ subset demonstrate a high degree of overlap between TCR sequences expressed by $T_{SCM}$- and $T_{CM}$-derived cells. While the TCR sequence detected in $T_{SCM}$ and $T_{CM}$ derived T cells were less frequently detected in the $T_{EM}$-derived cells, nevertheless, there was a significant number of specific public TCRs common to T cells derived from all memory T cell compartments.

Figures 6A, 6B:
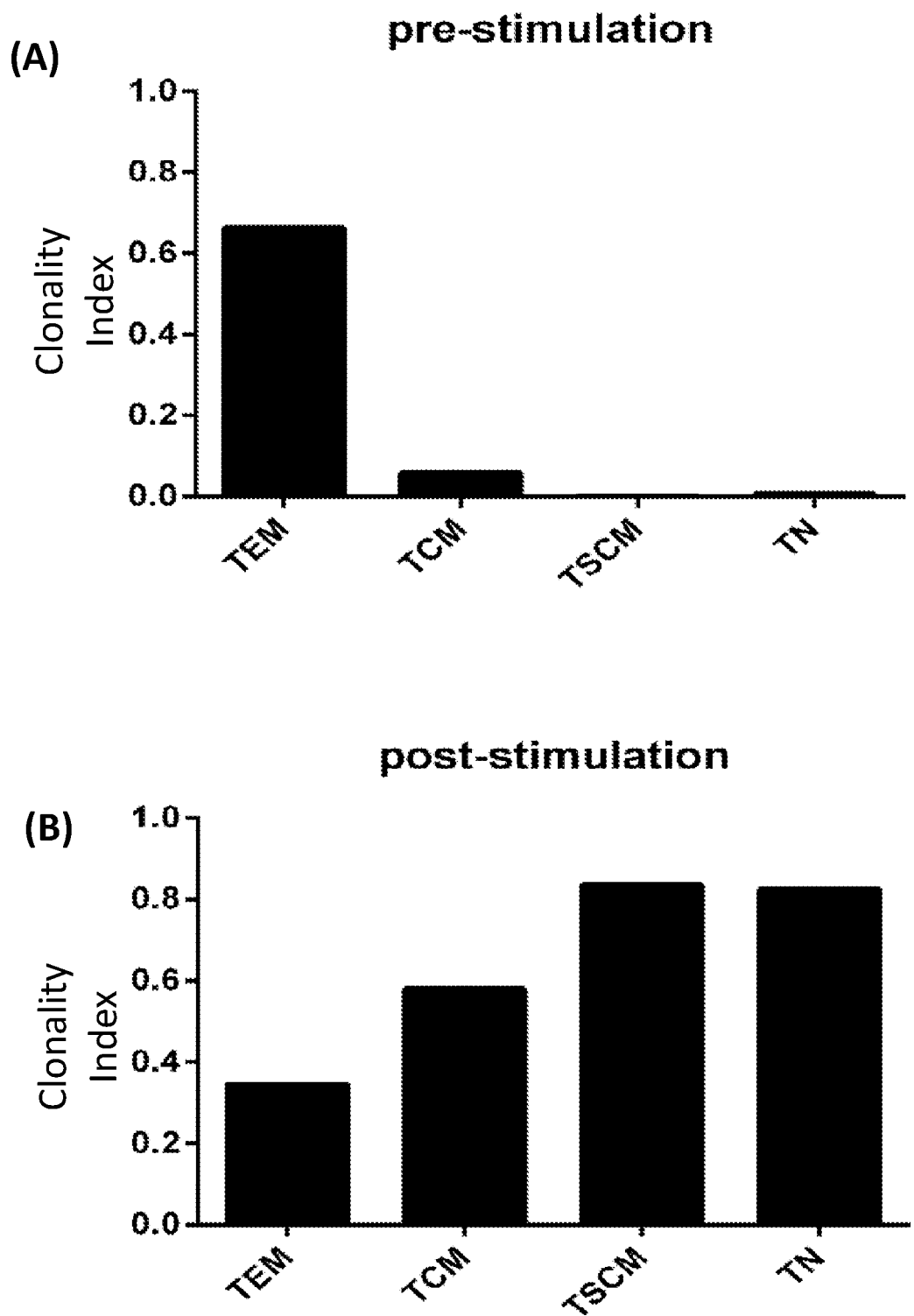
Figures 6C, 6D, 6E, 6F:
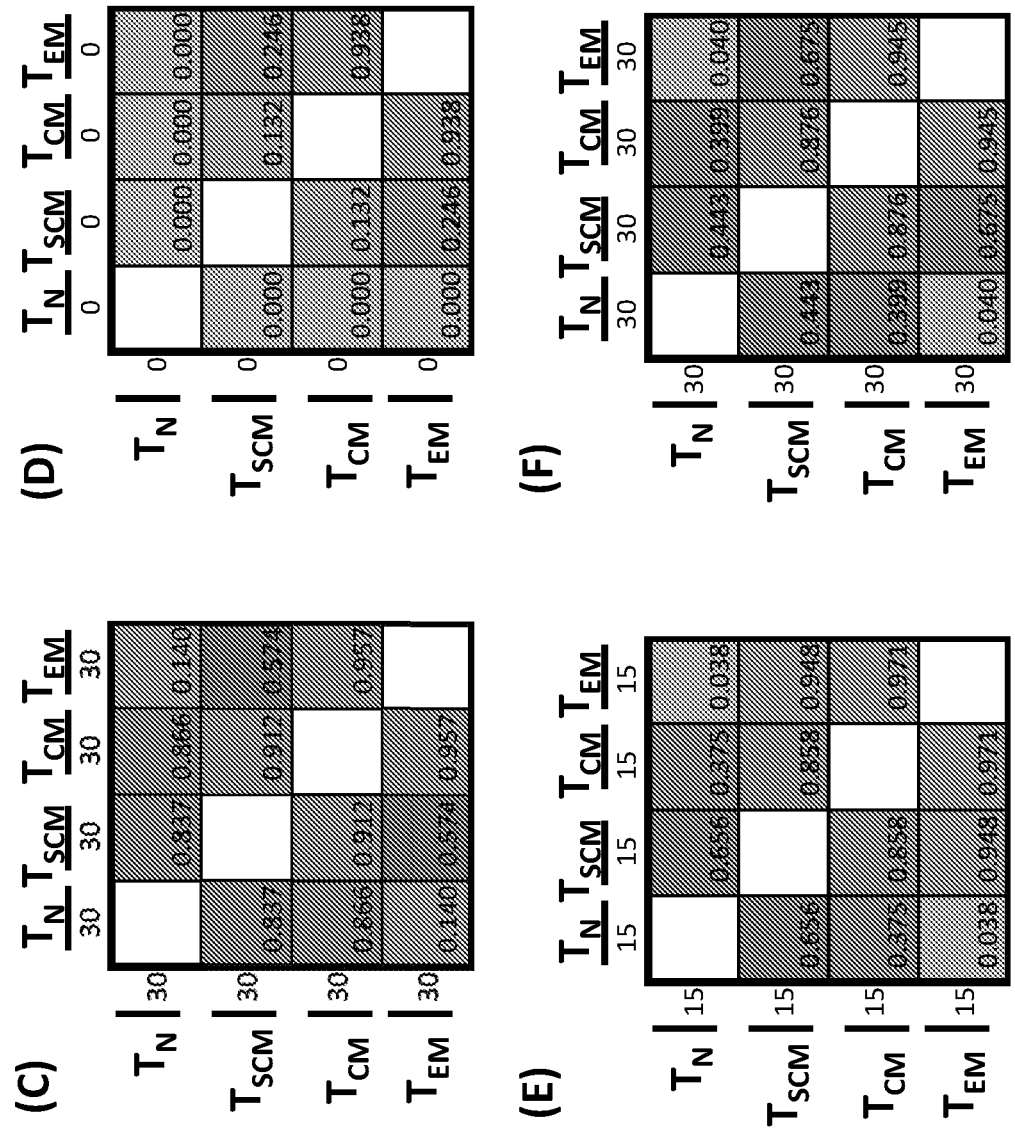
Figure 6G:
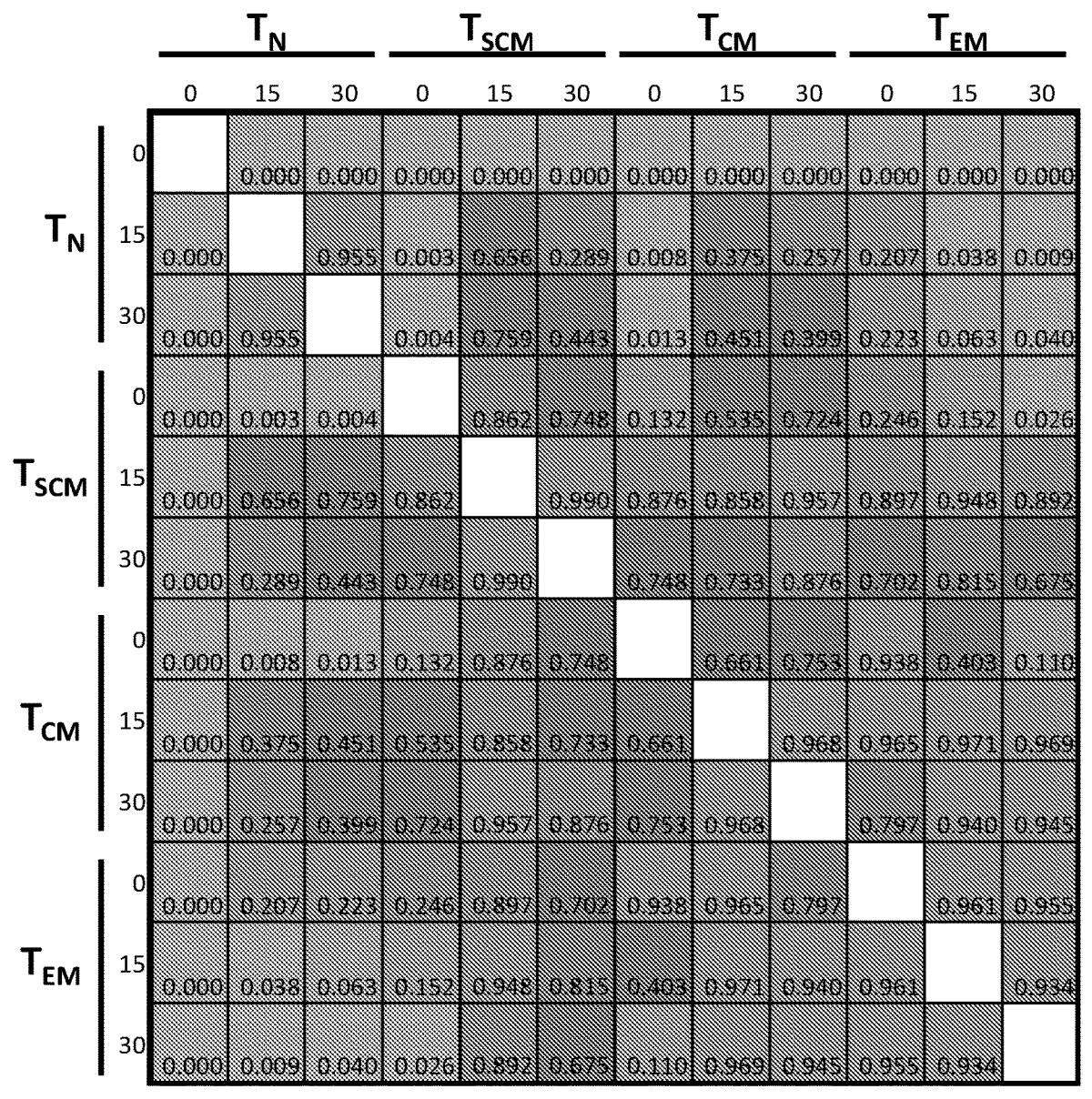

It was then examined if the same trend of TCR overlap would be present prior to antigen stimulation in peripheral blood. Therefore, $T_N$-, $T_{SCM}$-, $T_{CM}$- and $T_{EM}$-derived NLV-Tet+ T cells were sorted from another donor prior to stimulation and the TCR sequence was evaluated for clonality and overlap. TCR clonality describes the degree to which one or a few clones dominate the repertoire, with 0 being a flat distribution and 1 being an entirely oligoclonal sample. Prior to antigenic stimulation, $T_{EM}$ NLV-Tet+ T cells demonstrated a high degree of clonality, with a clonality index of 0.66 (FIG. 6A). In comparison, the $T_{CM}$ NLV-Tet+ T cells demonstrated a clonality index of 0.06, suggesting higher TCR clonal diversity, while the circulating $T_{SCM}$ and $T_N$ NLV-Tet+ T cells were highly diverse with a clonal index of 0.01 (FIG. 6A). In overlap analysis comparing the Tet+ T cells in the different subsets, however, NLV-Tet+ T cells detected in the $T_{EM}$ fraction were also differentially represented in the $T_{CM}$ repertoire (94% in FIG. 6D). On the other hand, $T_{SCM}$ cells, which had a highly diverse TCR repertoire, demonstrate very little overlap with $T_{CM}$ and $T_{EM}$ TCR sequences (13.2% and 24.6% respectively) (FIG. 6D). Strikingly, no TCR overlap between $T_N$ NLV-Tet+ T cells and $T_{SCM}$, $T_{CM}$ or $T_{EM}$ NLV-Tet+ T cells was identified in peripheral blood (FIG. 6D).

After 15 days of antigenic stimulation in vitro, the expanded NLV-Tet+ T cells adopted a restricted clonal diversity, with the clonality index ranging from 0.35 to 0.83 for all subsets (FIG. 6B). The overlap analysis data correlated with the previous observation that $T_{CM}$- and $T_{EM}$-derived NLV-Tet+ T cells bear highly overlapping TCR sequences (97% and 95% at Day 15 and Day 30 as shown in FIGS. 6E and 6F). Interestingly, $T_{SCM}$-derived Tet+ T cells developed a restricted TCR repertoire within 15 days post-stimulation, which is highly similar to $T_{CM}$- and $T_{EM}$-derived Tet+ T cells ($T_{SCM}/T_{CM}$: 86% and $T_{SCM}/T_{EM}$: 95% in FIG. 6E). Unlike the $T_{SCM}$-derived Tet+ T cells early after re-stimulation, $T_N$-derived Tet+ T cells demonstrated very different TCR sequences compared to $T_{CM}$- and $T_{EM}$-derived Tet+ T cells with an overlap of 38% and 3.8% respectively (FIG. 6E). While a significant fraction of $T_N$-derived Tet+ T cells expressing TCRs shared by $T_{CM}$-derived Tet+ T cells can be detected by day 30, the fraction shared by $T_{EM}$-derived Tet+ T cells remained small throughout 30 days of expansion. Thus, these data suggest that upon antigen stimulation, $T_{SCM}$ constitute the principal and immediate source for replenishing immunodominant NLV-specific $T_{CM}$ and $T_{EM}$ populations in the circulation.

An additional striking feature of the day 0 $T_{CM}$ and $T_{EM}$ Tet+ T cell population and the day 15 $T_{SCM}$-derived Tet+ T cell population is that these Tet+ T cells expressed CDR3 sequences CASSPQTGASYGYTF (SEQ ID NO:3) and CASSPKTGAVYGYTF (SEQ ID NO:4) that have previously been reported in public T cell receptors specific for the NLV-peptide (Yang et al., 2015, J Biol Chem 290:29106-29119). While these sequences were also detected in $T_N$-derived Tet+ T cells, their frequency was much lower than in $T_{SCM}$-, $T_{CM}$- or $T_{EM}$-derived Tet+ T cells (Table 2). In the dataset of the example herein, the $T_N$-derived Tet+ T cells also contained unique sequences that that were not shared with Tet+ T cells derived from other subsets. For example, the sequence CASSYVTGTGNYGYTF (SEQ ID NO:5) was only detected in $T_N$-derived Tet+ T cells post-stimulation in high frequencies (89% and 87% at day 15 and 30 respectively, Table 2). This suggests that $T_N$-derived Tet+ T cells can ultimately potentially expand upon antigen exposure to populate the immunodominant memory T cell pool, and also expand unique clones recognizing the antigen.

TABLE 2

Predominant clonotypes represented within naive and memory A2-NLV-specific CD8⁺ T cells in CMV seropositive donors

| Source | Amino Acid | TCRBV | TCRBJ | Frequency on different days (%) | | | | | | | | | | | |
|---|---|---|---|---|---|---|---|---|---|---|---|---|---|---|---|
| | | | | $T_{EM}$ | | | $T_{CM}$ | | | $T_{SCM}$ | | | $T_N$ | | |
| | | | | 0 | 15 | 30 | 0 | 15 | 30 | 0 | 15 | 30 | 0 | 15 | 30 |
| CK-42202 NLV pos | CASSPQTGASYGYTF (SEQ ID NO: 3) | TCRBV06-05 | TCRBJ01-02 | 21.29 | 10.53 | 8.13 | 8.06 | 46.30 | 62.72 | 2.56 | 83.57 | 67.66 | 0.00 | 0.22 | 0.11 |
| | CASSYVTGTGNYGYTF (SEQ ID NO: 5) | TCRBV06-05 | TCRBJ01-02 | 0.00 | 0.00 | 0.00 | 0.00 | 0.00 | 0.00 | 0.00 | 0.00 | 0.00 | 0.00 | 88.93 | 87.14 |
| | CSVAGTVNEQFF (SEQ ID NO: 6) | TCRBV29-01 | TCRBJ02-01 | 0.81 | 22.99 | 18.87 | 0.00 | 5.79 | 2.94 | 0.00 | 9.72 | 14.59 | 0.00 | 0.00 | 0.00 |
| | CAAGIFGTDTQYF (SEQ ID NO: 7) | TCRBV27-01 | TCRBJ02-03 | 0.00 | 4.29 | 5.79 | 0.00 | 6.57 | 5.38 | 0.00 | 0.00 | 0.00 | 0.00 | 0.00 | 0.00 |
| | CAWSISDIMNTEAFF (SEQ ID NO: 8) | TCRBV30-01 | TCRBJ01-01 | 0.00 | 1.80 | 0.83 | 0.00 | 12.31 | 6.95 | 0.00 | 0.00 | 0.00 | 0.00 | 0.00 | 0.00 |
| | CASSLEGYTEAFF (SEQ ID NO: 9) | TCRBV27-01 | TCRBJ01-01 | 6.20 | 4.99 | 3.31 | 2.42 | 2.99 | 1.47 | 0.00 | 0.00 | 0.00 | 0.00 | 0.00 | 0.00 |
| | CAWSVSDPLNTEAFF (SEQ ID NO: 10) | TCRBV30-01 | TCRBJ01-01 | 1.66 | 1.52 | 2.20 | 2.42 | 1.18 | 0.29 | 0.00 | 0.00 | 0.00 | 0.00 | 0.00 | 0.00 |
| CK-200D NLV pos | CASSPKTGAVYGYTF (SEQ ID NO: 4) | TCRBV06-05 | TCRBJ01-02 | | | 10.79 | | | 73.07 | | | 79.73 | | | 46.41 |
| | CASSHQTSGNTIYF (SEQ ID NO: 11) | TCRBV19-01 | TCRBJ01-03 | | | 17.04 | | | 0.09 | | | 0.00 | | | 0.00 |
| | CASSLKTGASYGYTF (SEQ ID NO: 12) | TCRBV06-05 | TCRBJ01-02 | | | 1.17 | | | 4.64 | | | 0.02 | | | 1.10 |
| | CASSVLAPTVGSTEAFF (SEQ ID NO: 13) | TCRBV10-02 | TCRBJ01-01 | | | 4.37 | | | 3.03 | | | 0.00 | | | 0.00 |
| | CASSYQTGASYGYTF (SEQ ID NO: 14) | TCRBV06-05 | TCRBJ01-02 | | | 4.22 | | | 1.81 | | | 0.00 | | | 0.00 |
| | CASSEIGATNYGYTF (SEQ ID NO: 15) | TCRBV06-01 | TCRBJ01-02 | | | 2.94 | | | 0.16 | | | 0.00 | | | 0.00 |

Figures 1, 7A:
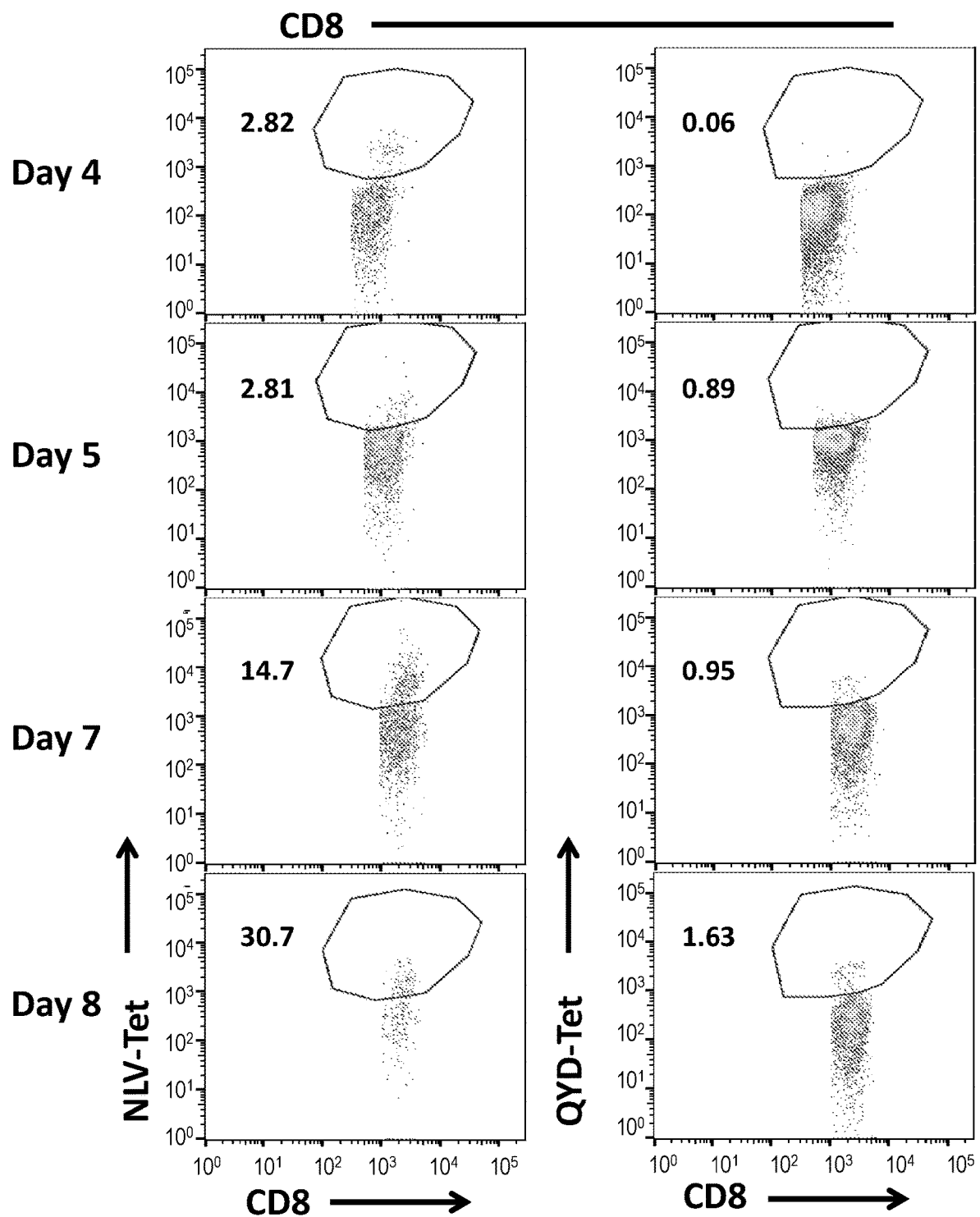
Figures 2, 7A:
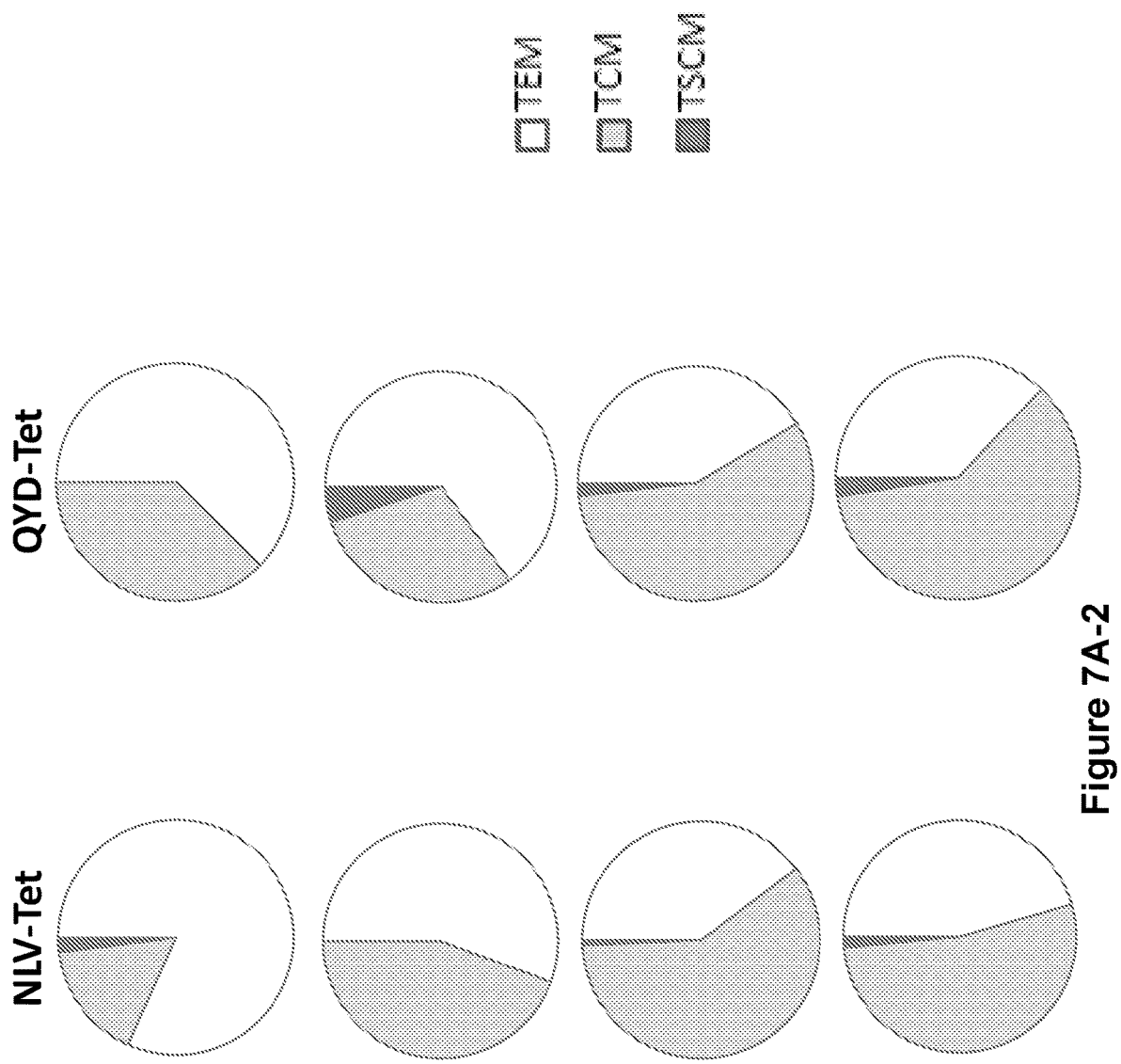
Figures 1, 7B:
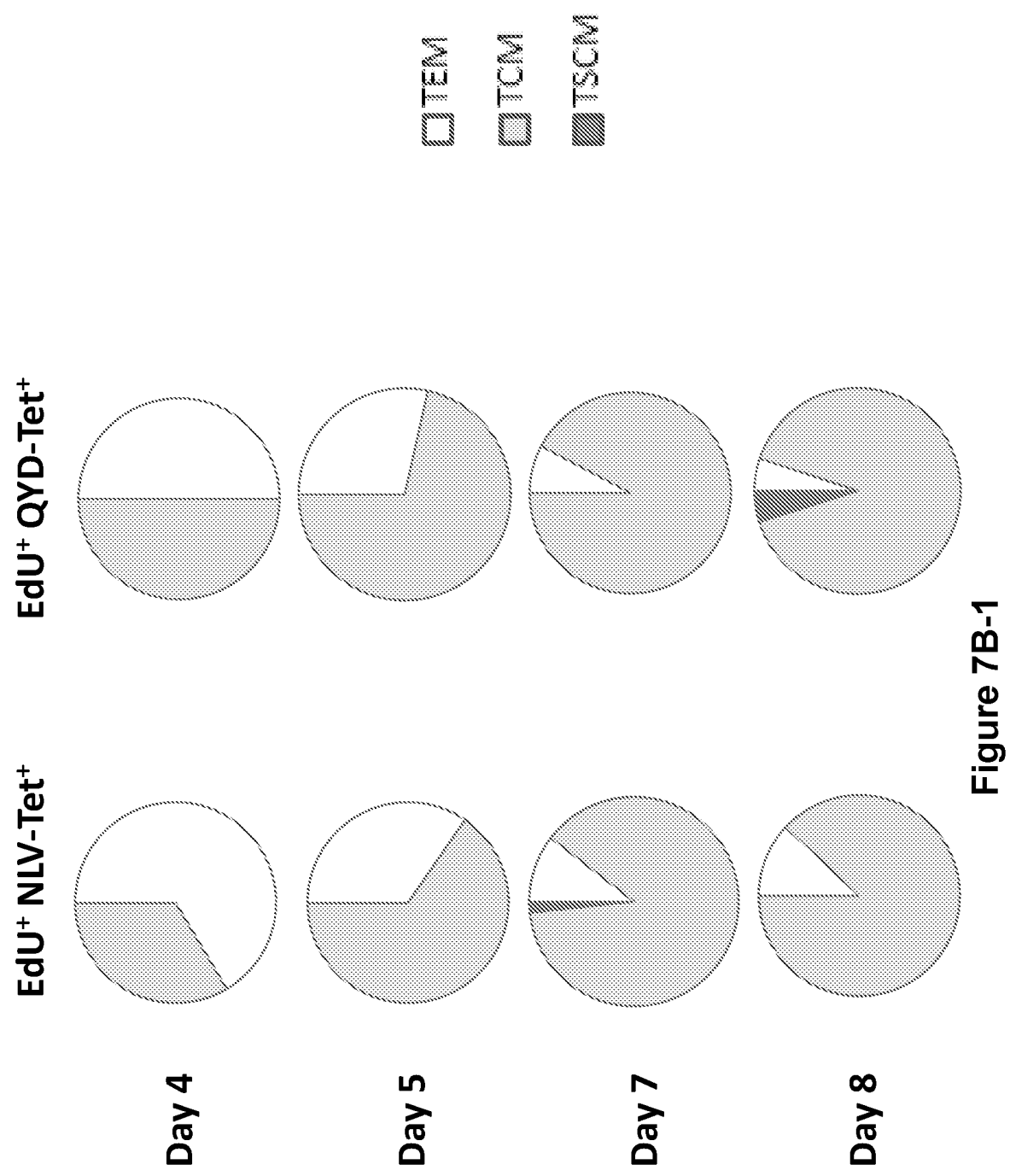
Figures 2, 7B:
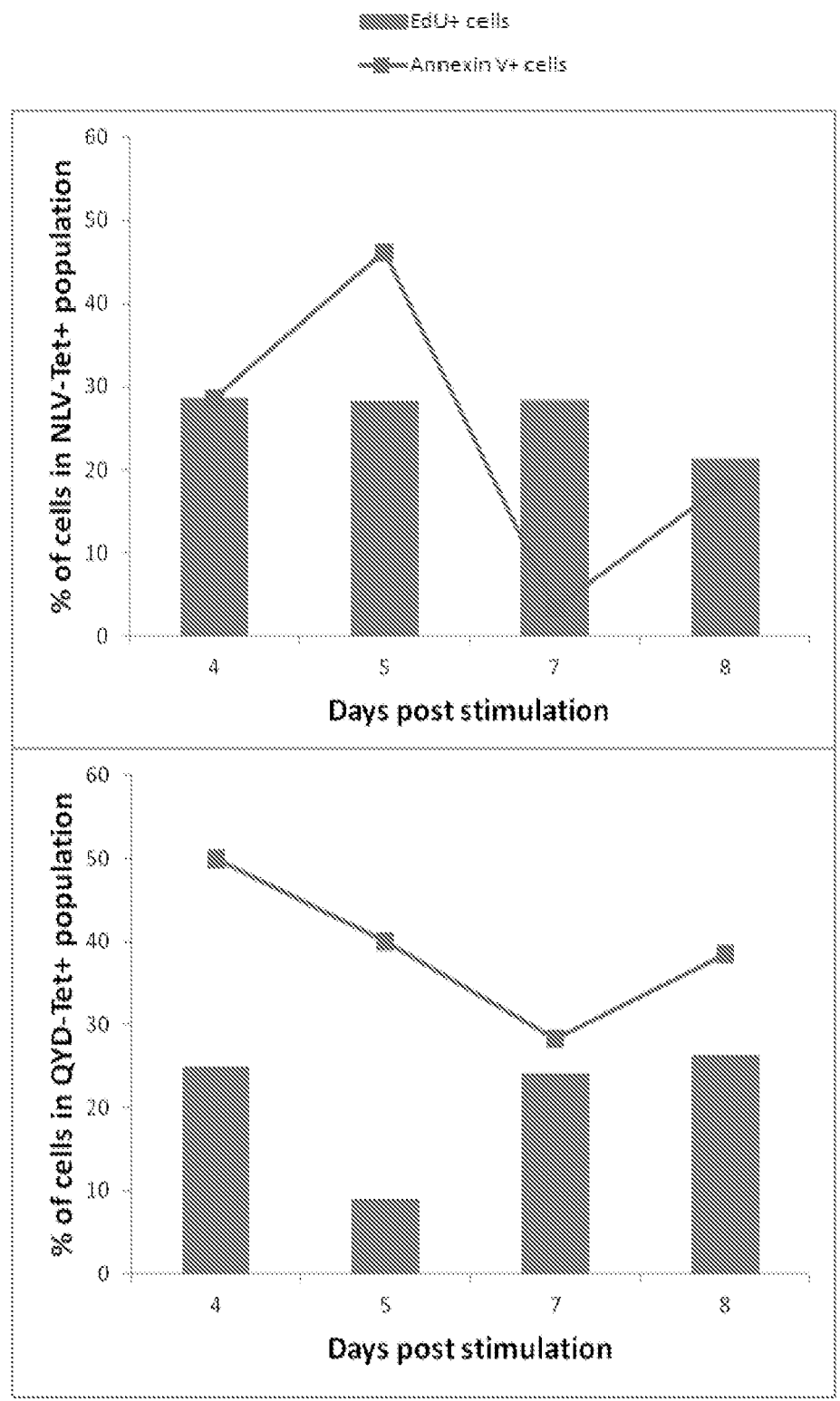

6.3.7. Immunodominance is not Caused by the Skewed Proliferation of $T_{SCM}$ Cells in Circulation The data above show that $T_{SCM}$-derived T cells demonstrate higher proliferative capacity generating superior expansion of antigen-specific T cells. Next it was tested whether the phenomenon of epitope-specific T cell immunodominance could be a consequence of either over-representation of or preferential proliferation of $T_{SCM}$ cells within T cells responding to immunodominant compared to subdominant epitopes. To address this question, the in vitro T cell proliferative capacity of $T_{SCM}$, $T_{CM}$, and $T_{EM}$ subsets, respectively, from a CMV seropositive donor co-inheriting HLA-A*0201 and A*2402, upon antigen specific stimulation, was measured. The immunodominant anti-CMV T cell response in donors co-inheriting these alleles has been shown to be directed against the NLV epitope presented by HLA-A*0201 (Lidehall et al., 2005, J Clin Immunol 25:473-481). T cells from the same donor were stimulated with NLV- and QYD-loaded autologous dendritic cells. Within 8 days post-stimulation, NLV-Tet$^+$ T cells were enriched to 31.7% and QYD-Tet$^+$ T cells to 1.6%, representing the immunodominant and subdominant response respectively (FIG. 7A). Strikingly, a similar memory phenotype was found for both A2-NLV- and A24-QYD-Tet$^+$ T cells, with no overrepresentation of $T_{SCM}$-derived T cells within the immunodominant A2-NLV-Tet$^+$ T cells in culture (FIG. 7B). To further evaluate the relative proliferative potential of immunodominant and subdominant epitope-specific T cells, they were examined for EdU incorporation as proliferation marker and Annexin V expression as apoptosis marker. Similar levels of proliferating cells were found within A2-NLV- and A24-QYD-Tet$^+$ T cells, with no preferential proliferation within the immunodominant A2-NLV-Tet$^+$ T cells (FIG. 7B). However, the A24-QYD-Tet$^+$ T cells contained a higher percentage of Annexin V$^+$ cells compared to A2-NLV-Tet$^+$ T cells (FIG. 7B). These data suggest that a higher level of T cell apoptosis within subdominant epitope-specific T cells might promote the preferential enrichment of immunodominant T cells.

6.4. Discussion

This example described herein characterized HLA-A0201-restricted $T_N$, $T_{SCM}$, $T_{CM}$ and $T_{EM}$ cells specific for the immunodominant NLV peptide of CMVpp65 that were isolated by immunoadsorption to tetramers from the blood of healthy seropositive donors, and T cells derived from these subsets after sequential intervals of in vitro sensitization. The Tet$^+$ and Tet$^-$ T cells from the same T cell subset population were also compared. The results suggest a major role for $T_{SCM}$ cells as a durable reservoir of T cell memory in the recall immune response.

This analysis of antigen-specific T cells in these different T cell subsets has demonstrated that Tet$^+$ $T_{SCM}$ in the blood exhibit a CD45RA$^+$CCR7$^+$ and CD62L$^+$ phenotype similar to $T_N$ cells, but also express CD95. Upon sensitization with antigen, both Tet$^+$CD95$^-$ $T_N$ and Tet$^+$CD95$^+$ $T_{SCM}$ cells were regularly detected. Both the Tet$^+$ $T_N$ and Tet$^+$T$_{SCM}$ cells expressed significantly higher levels of the co-stimulatory marker CD27 than detected on Tet$^+$ $T_{CM}$ and Tet$^+$T$_{EM}$ cells; Tet$^+$ $T_{SCM}$ cells demonstrated somewhat higher expression of the activation marker CD127. Conversely, the Tet$^+$ $T_N$ and Tet$^+$ $T_{SCM}$ cells expressed lower levels of the senescence marker CD57; Tet$^+$ $T_N$ cells expressed a significantly lower level of CD28. Strikingly, after in vitro sensitization, Tet$^+$ T cells derived from all subsets generated a similarly high proportion of cells expressing PD-1, which differed significantly from the low proportion of PD-1$^+$ cells in the Ter T cells derived from these subsets. In addition, the killer-cell lectin like receptor G1 (KLRG1), which is usually considered to be a marker of late differentiation, was expressed to a similar degree in the NLV-peptide responding $T_N$-, $T_{SCM}$-, $T_{CM}$- and $T_{EM}$-derived T cells. In contrast, this marker was expressed at a minimal level in the Tet$^-$ $T_N$-derived T cells. Thus, in latently infected healthy seropositive individuals, secondary stimulation with the viral antigen induces expression of both PD-1 and KLRG-1 in all stages of T cell memory. However, the Tet$^+$ $T_N$- and $T_{SCM}$-derived T cells still differentially express the CD45RA, CCR7 and CD62L markers associated with earlier stages of maturation and the capacity for targeted migration and longer survival.

At a functional level, Tet$^+$ $T_N$-, $T_{SCM}$-, $T_{CM}$- and $T_{EM}$-derived T cells all contained cells capable of secreting TNF-α and IFN-γ, and degranulating in response to antigen stimulation, although the proportion of Tet$^+$ $T_{EM}$- and $T_{CM}$-derived T cells exhibiting these functions were higher than in Tet$^+$ $T_{SCM}$- or $T_N$-derived T cells. Thus, in contrast to a previous report where CD95$^-$ T cells were unable to secrete cytokines after HCMV-specific stimulation (Schmueck-Henneresse et al., 2015, J Immunol 194:5559-5567), the example described herein provides evidence that antigen-responsive $T_N$-derived T cells do exhibit these effector functions and cannot, thereby, be qualitatively distinguished from antigen-responsive $T_{SCM}$-derived T cells. A study by Pulko et al. (2016, Nat Immunol 17:966-975) has also shown that human memory T cells with a naive phenotype secrete multiple cytokines in response to secondary stimulation with viral antigens but differ transcriptionally from memory and effector T cells. However, the example described herein did not find that Tet$^+$ CD95$^+$ $T_{SCM}$ cells are functionally distinguishable from Tet$^+$ CD95$^-$ $T_N$ cells on the basis of their proliferative response to antigen stimulation. Indeed, their proliferative response also significantly exceeded that of Tet$^+$ $T_{CM}$ and Tet$^+$ $T_{EM}$ cells.

A diverse TCR repertoire has been postulated to mediate optimal control of pathogens by increasing the probability that microbial escape mutations would be recognized by one of the TCRαβ pairs represented within the repertoire (Cornberg et al., 2006, J Clin Invest 116:1443-1456; Meyer-Olson et al., 2004, J Exp Med 200:307-319). The TCR sequencing analysis in the example described herein has shown that in the peripheral circulation, the $T_N$ and $T_{SCM}$ cells recognizing the same epitope NLV are more diverse than $T_{CM}$ and $T_{EM}$ cells. This broad TCR repertoire of $T_N$ and $T_{SCM}$ cells recognizing the same pathogen could be hypothesized to provide better control of virus infection. However, upon antigen stimulation, the example herein found that $T_{SCM}$ cells generate T cells that are oligoclonal within 15 days after antigen encounter, and further that these T cells express a repertoire closely related to that of Tet$^+$ $T_{EM}$ and Tet$^+$ $T_{CM}$ cells that are dominant in the circulation. The fact that $T_{SCM}$-derived CMV-specific T cells share high overlap of TCR usage with $T_{CM}$ and $T_{EM}$-derived CMV-specific T cells early post-stimulation, provides evidence that $T_{SCM}$-derived T cells are particularly effective in reconstituting populations of immunodominant memory T cells in the blood. Moreover, the heterogeneous spectrum of clones generated from $T_N$ cells after antigen stimulation, which differs from that of the other memory T cell subsets, suggests that $T_N$ cells serve as a pool of precursor cells capable of selecting peptide-specific T cells with a broader spectrum of binding characteristics, from which memory T cells of optimal avidity can be selected for expansion if required to control viral variants.

T cell responses to latent viruses often focus on a small number of the available antigenic epitopes and use a narrow TCR repertoire, a phenomenon termed "immunodominance." A number of factors have been reported to influence immunodominance, including antigen presentation, peptide-MHC binding affinity and stability or TCR avidity and the frequency of precursors in the naive T cell pool (Khan et al., 2007, J Immunol 178:4455-4465). In the two donors tested in the example herein, an overrepresentation or a preferential proliferation of $T_{SCM}$-derived T cells responding to immunodominant epitopes was not found, compared to those responding to subdominant epitopes. Instead, a higher level of T cell apoptosis was observed within subdominant epitope-specific T cells, which might promote the preferential enrichment of immunodominant T cells. Previous studies have also indicated that the characteristics of TCR binding to pMHC complexes may also regulate clonal apoptosis (Tscharke et al., 2015, Nat Rev Immunol 15:705-716). Indeed, TCRs with a subthreshold affinity for pMHC-I preferentially undergo apoptosis early in the response via a process that is regulated by the BCL-2 family members BIM, NOXA and MCL1 (Wensveen et al., 2010, Immunity 32:754-765). Thus, the data of the example herein are in accord with that of others and suggest that apoptosis may also be crucial for shaping adaptive immune responses, thereby enhancing the selection of clones with greater persistence.

Another feature of the Tet$^+$ T cells specific for the NLV HLA-A0201 epitope generated from $T_{SCM}$ cells was their expression of T cell receptor with amino acid sequences identical to sequences previously reported for public T cell receptors specific for the NLV epitope (Yang et al., 2015, J Biol Chem 290:29106-29119). Public T cell receptors are peptide-specific TCRs with highly homologous sequences detected in multiple individuals (Li et al., 2012, Cell Res 22:33-42). Public TCRs have been described in T cells responding to a variety of human viruses (Argaet et al., 1994, J Exp Med 180:2335-2340). NLV peptide-specific T cell repertoires have been shown to exhibit a high prevalence of public TCRs (Wang et al., 2012, Sci Transl Med 4:128ra142; Nguyen et al., 2014, J Immunol 192:5039-5049; Trautmann et al., 2005, J Immunol 175:6123-6132). Indeed, seven public CDR3α and six CDR3β motifs account for ~70% of the total NLV-specific TCR response (Wang et al., 2012, Sci Transl Med 4:128ra142). The example herein also identified a common TCRβ CDR3 represented within $T_N$, $T_{SCM}$, $T_{CM}$ and $T_{EM}$-derived Tet$^+$ T cells post-stimulation that bears the S*$_n$TG*$_n$GY (SEQ ID NO:16; *n indicates any amino acid sequence of any length and any amino acid combination) motif which has the highest reported frequency among the other published motifs. Two other studies have also shown the same S*$_n$TG*$_n$GY (SEQ ID NO:16; *n indicates any amino acid sequence of any length and any amino acid combination) motif within HLA-A*0201 NLV-specific T cells from both CMV seropositive donors (Hanley et al., 2015, Sci Transl Med 7:285ra263; Neller et al., 2015, Immunol Cell Biol 93:625-633). The crystal structures of two public TCRs in complex with NLV-HLA-A2 have been reported (Yang et al., 2015, J Biol Chem 290:29106-29119). These and other studies (Yang et al., 2015, J Biol Chem 290:29106-29119; Welsh et al., 2010, Immunol Rev 235:244-266) have provided evidence that different pairings of public CDR3 α and β domains can mediate a multiplicity of high affinity TCRs recognizing the same peptide MHC ligand (Yang et al., 2015, J Biol Chem 290:29106-29119). Current evidence indicates that public TCRs are produced more frequently during random V(D)J gene rearrangements, a random process termed "convergent recombination" (Miles et al., 2011, Immunol Cell Biol 89:375-387). Thereafter, this may be further selected by combinatorial bias. Such public TCRs could potentially propagate more and establish better virus control over other clones in the TCR repertoire.

In conclusion, first, the example herein demonstrated that antigen-specific $T_{SCM}$-derived T cells exhibit and maintain a less differentiated phenotype than those derived from other memory T cell populations responding to a single epitope, displaying an expansion profile of tissue homing, co-stimulatory and senescence markers that is intermediate between $T_N$ and $T_{CM}$-derived cells. In addition, Tet$^+$ CMVpp65 NLV-specific T cells were regularly detected cells derived from the CD95$^-$ $T_N$ cell compartment. However, antigen-specific $T_{SCM}$ cells differ from Tet$^+$ $T_N$ cells as well as Tet$^+$ $T_{CM}$ and Tet$^+$ $T_{EM}$ cells in that they proliferate to a much higher degree in response to antigen stimulation. Second, antigen-specific Tet$^+$ $T_N$ and Tet$^+$ $T_{SCM}$-derived cells, unlike Tet$^-$ $T_N$ and Tet$^-$ $T_{SCM}$-derived cells, were found to express PD-1 and KLRG-1 at levels similar to those expressed by Tet$^+$ $T_{CM}$- and Tet$^+$ $T_{EM}$-derived cells. They also exhibit effector function, indicating the capacity to generate TNF-α, IFN-γ and granzyme B. Third, this example has demonstrated that, in response to antigen stimulation, $T_{SCM}$ cells not only undergo marked proliferation but also rapidly select T cell clones specific for the CMVpp65 NLV epitope presented by HLA-A*0201 that, by TCR sequencing, are public TCRs identical to those expressed by NLV/HLA-A*0201 specific $T_{EM}$ and $T_{CM}$ cells that are immunodominant in the blood of the HLA-A*0201 seropositive donors. Unlike the Tet$^+$ $T_{SCM}$ cells, Tet$^+$ $T_N$ cells do not rapidly select clones expressing the immunodominant TCRs detected in $T_{EM}$ and $T_{CM}$ population in the blood. Rather, the Tet$^+$ $T_N$ cells maintain a distinct repertoire that is markedly more varied than that detected in NLV-specific $T_{CM}$ and $T_{EM}$ cells in the blood, as that detected in $T_{SCM}$-derived cells upon 15 days of in vitro stimulation. Finally, the example herein suggests that while the expansion of $T_{SCM}$, $T_{CM}$ and $T_{EM}$ cells proliferating in response to the immunodominant epitope NLV presented by HLA-A*0201 is similar to those proliferating in response to the subdominant QYD epitope presented by HLA-A*2402 expressed by the same donor, the proportions of immunodominant NLV-specific $T_{SCM}$, $T_{CM}$, and $T_{EM}$-derived cells that undergo apoptosis are markedly smaller than that of the subdominant QYD-specific counterparts.

These findings have implications for the design of T cell-based immunotherapies. This example has provided evidence that the $T_{SCM}$ subset serves as the major durable reservoir for repopulating immunodominant $T_{EM}$ and $T_{CM}$ cells in the circulation upon secondary antigenic challenge. Adoptive transfer of virus-specific T cell lines enriched for $T_{SCM}$ could potentially provide better disease control by providing immunodominant virus-specific T cells capable of rapid and extensive proliferation and enhanced persistence.

7. INCORPORATION BY REFERENCE

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of generating a population of cells comprising antigen-specific T cells for therapeutic administration to a human patient having or suspected of having a pathogen or cancer, comprising: (a) ex vivo sensitizing a population of human blood cells to one or more antigens of the pathogen or cancer over a period of time in culture, wherein at the initiation of said period of time, the population of human blood cells contains at least 50% stem cell-like memory T cells ($T_{SCM}$ cells); and (b) cryopreserving (i) the ex vivo sensitized population of human blood cells, or (ii) cells derived therefrom that comprise antigen-specific T cells recognizing the one or more antigens of the pathogen or cancer; thereby producing said population of cells comprising antigen-specific T cells.

2. The method of claim 1, wherein the period of time in culture is in the range of 9-21 days.

3. The method of claim 2, wherein the period of time in culture is in the range of 9-14 days.

4. The method of claim 1, wherein the population of cells comprising antigen-specific T cells comprises antigen-specific T cells that endogenously express a public T cell receptor (TCR) recognizing the one or more antigens.

5. The method of claim 1, wherein the population of cells comprising antigen-specific T cells comprises antigen-specific T cells that recombinantly express a public TCR recognizing the one or more antigens.

6. The method of claim 5, which further comprises transducing the population of human blood cells with a nucleic acid encoding a public TCR at a time when the population of human blood cells has been cultured for 3-5 days.

7. A method of generating a population of cells comprising antigen-specific T cells for therapeutic administration to a human patient having or suspected of having a pathogen or cancer, comprising: (a) ex vivo sensitizing a population of human blood cells to one or more antigens of the pathogen or cancer over a period of time in culture, wherein at the initiation of said period of time, the population of human blood cells contains at least 50% stem cell-like memory T cells ($T_{SCM}$ cells); and (b) cryopreserving (i) the ex vivo sensitized population of human blood cells, or (ii) cells derived therefrom that comprise antigen-specific T cells recognizing the one or more antigens of the pathogen or cancer; thereby producing said population of cells comprising antigen-specific T cells, wherein the population of cells comprising antigen-specific T cells comprises antigen-specific T cells that endogenously or recombinantly express a public TCR recognizing the one or more antigens, wherein the one or more antigens is cytomegalovirus (CMV) pp65, and the public TCR comprises a β-chain comprising a variable domain, which comprises a complementarity determining region (CDR)3 of SEQ ID NO:3 or SEQ ID NO:4.

8. The method of claim 1, wherein the population of cells comprising antigen-specific T cells comprises antigen-specific T cells that recombinantly express a chimeric antigen receptor (CAR) recognizing the one or more antigens.

9. A method of generating a population of cells comprising antigen-specific T cells for therapeutic administration to a human patient having or suspected of having a CMV infection, comprising transducing a population of human blood cells with a nucleic acid encoding a public TCR recognizing CMV pp65, wherein the public TCR comprises a β-chain comprising a variable domain, which comprises a CDR3 of SEQ ID NO:3, or SEQ ID NO:4, and wherein the population of human blood cells contains at least 50% $T_{SCM}$ cells; thereby producing said population of cells comprising antigen-specific T cells.

10. The method of claim 1, wherein the population of human blood cells contains at least 90% $T_{SCM}$ cells.

11. The method of claim 1, wherein the population of human blood cells contains at least 99% $T_{SCM}$ cells.

12. The method of claim 1, wherein the population of human blood cells contains less than 10% naive T ($T_N$) cells.

13. The method of claim 1, wherein the population of human blood cells contains less than 1% $T_N$ cells.

14. The method of claim 1, which further comprises a step of deriving the population of human blood cells from a human cell sample, wherein the deriving step comprises enriching for $T_{SCM}$ cells from the human cell sample, and wherein the enriching step comprises selecting for cells that are $CD3^+CD62L^+CD45RO^-CD95^+$.

15. The method of claim 1, wherein the ex vivo sensitizing step comprises ex vivo sensitizing the population of human blood cells to one or more antigens of the pathogen.

16. The method of claim 1, wherein the ex vivo sensitizing step comprises ex vivo sensitizing the population of human blood cells to one or more antigens of the cancer.

17. A method of treating a human patient having a pathogen or cancer, comprising: (i) generating a population of cells comprising antigen-specific T cells according to the method of claim 1; and (ii) administering the population of cells comprising antigen-specific T cells to the human patient.

18. A method of treating a human patient having a pathogen or cancer, comprising administering a population of cells comprising antigen-specific T cells to the human patient, wherein the population of cells comprising antigen-specific T cells is the product of a method comprising generating the population of cells comprising antigen-specific T cells according to the method of claim 1.

19. The method of claim 1, wherein the antigen-specific T cells contained in the population of cells comprising antigen-specific T cells are restricted by an HLA allele shared with the diseased cells in the human patient.

20. The method of claim 1, wherein the antigen-specific T cells contained in the population of cells comprising antigen-specific T cells share at least 2 out of 8 HLA alleles with the diseased cells in the human patient.

21. The method of claim 1, wherein the population of human blood cells is derived from a human donor that is allogeneic to the human patient.

22. The method of claim 17, wherein the step of administering comprises administering the population of cells comprising antigen-specific T cells to the human patient, at a dose that is less than or equal to about $1\times10^5$ cells of the population of cells comprising antigen-specific T cells per kg of the human patient.

23. The method of claim 17, wherein the step of administering comprises administering the population of cells comprising antigen-specific T cells to the human patient, at a dose that is less than or equal to about $5\times10^3$ cells of the population of cells comprising antigen-specific T cells per kg of the human patient.

24. The method of claim 17, wherein the step of administering comprises administering the population of cells comprising antigen-specific T cells to the human patient, at a dose that is less than or equal to about $1\times10^3$ cells of the population of cells comprising antigen-specific T cells per kg of the human patient.

25. The method of claim 22, wherein the step of administering comprises administering the population of cells comprising antigen-specific T cells to the human patient at the dose weekly.

26. The method of claim 17, wherein the step of administering is by bolus intravenous infusion.

27. The method of claim 17, wherein the step of administering comprises administering at least 2 doses of the population of cells comprising antigen-specific T cells to the human patient.

28. The method of claim 17, wherein the step of administering comprises administering a first cycle of one dose per week of the population of cells comprising antigen-specific T cells for 3 consecutive weeks followed by a washout period during which no dose of the population of cells comprising antigen-specific T cells is administered, followed by a second cycle of said one dose per week of the population of cells comprising antigen-specific T cells for 3 consecutive weeks.

29. A population of cells comprising antigen-specific T cells for therapeutic administration to a human patient having or suspected of having a pathogen or cancer, wherein the population of cells comprising antigen-specific T cells is the product of a method comprising generating the population of cells comprising antigen-specific T cells according to the method of claim 1.

30. The population of cells of claim 29, wherein the population of cells is cryopreserved.

31. A cell bank comprising a plurality of populations of cells of claim 29.

32. The method of claim 8, wherein the period of time in culture is in the range of 9-21 days.

33. The method of claim 10, wherein the period of time in culture is in the range of 9-21 days.

34. The method of claim 12 wherein the period of time in culture is in the range of 9-21 days.

35. The method of claim 14, wherein the period of time in culture is in the range of 9-21 days.

* * * * *

SEQUENCE LISTING

<160> NUMBER OF SEQ ID NOS: 16

<210> SEQ ID NO 1
<211> LENGTH: 9
<212> TYPE: PRT
<213> ORGANISM: Artificial Sequence
<220> FEATURE:
<223> OTHER INFORMATION: peptide tetrameric complexe

<400> SEQUENCE: 1

Asn Leu Val Pro Met Val Ala Thr Val
1               5

<210> SEQ ID NO 2
<211> LENGTH: 9
<212> TYPE: PRT
<213> ORGANISM: Artificial Sequence
<220> FEATURE:
<223> OTHER INFORMATION: peptide tetrameric complexe

<400> SEQUENCE: 2

Gln Tyr Asp Pro Val Ala Ala Leu Phe
1               5

<210> SEQ ID NO 3
<211> LENGTH: 15
<212> TYPE: PRT
<213> ORGANISM: Artificial Sequence
<220> FEATURE:
<223> OTHER INFORMATION: CDR3 sequence of T cell receptor specific for
      NLV-peptide

<400> SEQUENCE: 3

Cys Ala Ser Ser Pro Gln Thr Gly Ala Ser Tyr Gly Tyr Thr Phe
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: CDR3 sequence of T cell receptor specific for
      NLV-peptide

<400> SEQUENCE: 4

Cys Ala Ser Ser Pro Lys Thr Gly Ala Val Tyr Gly Tyr Thr Phe
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: CDR3 sequence of T cell receptor specific for
      NLV-peptide

<400> SEQUENCE: 5

Cys Ala Ser Ser Tyr Val Thr Gly Thr Gly Asn Tyr Gly Tyr Thr Phe
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: CDR3 sequence of T cell receptor specific for
      NLV-peptide

```
<400> SEQUENCE: 6

Cys Ser Val Ala Gly Thr Val Asn Glu Gln Phe Phe
1               5                   10

<210> SEQ ID NO 7
<211> LENGTH: 14
<212> TYPE: PRT
<213> ORGANISM: Artificial Sequence
<220> FEATURE:
<223> OTHER INFORMATION: CDR3 sequence of T cell receptor specific for
      NLV-peptide

<400> SEQUENCE: 7

Cys Ala Ala Gly Gly Ile Phe Gly Thr Asp Thr Gln Tyr Phe
1               5                   10

<210> SEQ ID NO 8
<211> LENGTH: 15
<212> TYPE: PRT
<213> ORGANISM: Artificial Sequence
<220> FEATURE:
<223> OTHER INFORMATION: CDR3 sequence of T cell receptor specific for
      NLV-peptide

<400> SEQUENCE: 8

Cys Ala Trp Ser Ile Ser Asp Ile Met Asn Thr Glu Ala Phe Phe
1               5                   10                  15

<210> SEQ ID NO 9
<211> LENGTH: 13
<212> TYPE: PRT
<213> ORGANISM: Artificial Sequence
<220> FEATURE:
<223> OTHER INFORMATION: CDR3 sequence of T cell receptor specific for
      NLV-peptide

<400> SEQUENCE: 9

Cys Ala Ser Ser Leu Glu Gly Tyr Thr Glu Ala Phe Phe
1               5                   10

<210> SEQ ID NO 10
<211> LENGTH: 15
<212> TYPE: PRT
<213> ORGANISM: Artificial Sequence
<220> FEATURE:
<223> OTHER INFORMATION: CDR3 sequence of T cell receptor specific for
      NLV-peptide

<400> SEQUENCE: 10

Cys Ala Trp Ser Val Ser Asp Pro Leu Asn Thr Glu Ala Phe Phe
1               5                   10                  15

<210> SEQ ID NO 11
<211> LENGTH: 14
<212> TYPE: PRT
<213> ORGANISM: Artificial Sequence
<220> FEATURE:
<223> OTHER INFORMATION: CDR3 sequence of T cell receptor specific for
      NLV-peptide

<400> SEQUENCE: 11

Cys Ala Ser Ser His Gln Thr Ser Gly Asn Thr Ile Tyr Phe
1               5                   10

<210> SEQ ID NO 12
<211> LENGTH: 15
<212> TYPE: PRT
```

```
<213> ORGANISM: Artificial Sequence
<220> FEATURE:
<223> OTHER INFORMATION: CDR3 sequence of T cell receptor specific for
      NLV-peptide

<400> SEQUENCE: 12

Cys Ala Ser Ser Leu Lys Thr Gly Ala Ser Tyr Gly Tyr Thr Phe
1               5                   10                  15

<210> SEQ ID NO 13
<211> LENGTH: 17
<212> TYPE: PRT
<213> ORGANISM: Artificial Sequence
<220> FEATURE:
<223> OTHER INFORMATION: CDR3 sequence of T cell receptor specific for
      NLV-peptide

<400> SEQUENCE: 13

Cys Ala Ser Ser Val Leu Ala Pro Thr Val Gly Ser Thr Glu Ala Phe
1               5                   10                  15

Phe

<210> SEQ ID NO 14
<211> LENGTH: 15
<212> TYPE: PRT
<213> ORGANISM: Artificial Sequence
<220> FEATURE:
<223> OTHER INFORMATION: CDR3 sequence of T cell receptor specific for
      NLV-peptide

<400> SEQUENCE: 14

Cys Ala Ser Ser Tyr Gln Thr Gly Ala Ser Tyr Gly Tyr Thr Phe
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: CDR3 sequence of T cell receptor specific for
      NLV-peptide

<400> SEQUENCE: 15

Cys Ala Ser Ser Glu Ile Gly Ala Thr Asn Tyr Gly Tyr Thr Phe
1               5                   10                  15

<210> SEQ ID NO 16
<211> LENGTH: 5
<212> TYPE: PRT
<213> ORGANISM: Artificial Sequence
<220> FEATURE:
<223> OTHER INFORMATION: CDR3 sequence motif of T cell receptor specific
      for NLV-peptide
<220> FEATURE:
<221> NAME/KEY: NON_CONS
<222> LOCATION: (1)..(2)
<223> OTHER INFORMATION: non-consecutive amino acid
<220> FEATURE:
<221> NAME/KEY: NON_CONS
<222> LOCATION: (3)..(4)
<223> OTHER INFORMATION: non-consecutive amino acid

<400> SEQUENCE: 16

Ser Thr Gly Gly Tyr
1               5
```